(12) United States Patent
Pedersen et al.

(10) Patent No.: US 6,642,014 B1
(45) Date of Patent: Nov. 4, 2003

(54) ENZYME ACTIVITY SCREEN WITH DIRECT SUBSTRATE REPLACEMENT

(75) Inventors: Henrik Pedersen, Bagsværd (DK); Swen Hölder, Frankfurt/M (DE); Jørgen Kjems, Risskov (DK); Mette Lund, Århus (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/395,017

(22) Filed: Sep. 13, 1999

Related U.S. Application Data

(63) Continuation of application No. PCT/DK99/00441, filed on Aug. 19, 1999.

(30) Foreign Application Priority Data

Aug. 19, 1998 (DK) .......................................... 1998 01044
Sep. 2, 1998 (DK) .......................................... 1998 01106

(51) Int. Cl.[7] ..................... G01N 33/573; G01N 33/53; C12Q 1/70; C12Q 1/68
(52) U.S. Cl. ................. 435/7.4; 435/5; 435/6; 435/7.1; 435/7.6; 435/DIG. 3; 435/DIG. 4; 435/DIG. 5; 435/DIG. 6
(58) Field of Search .......................... 435/6, 7.1, 5, 7.4, 435/7.6, DIG. 3, DIG. 4, DIG. 5, DIG. 6

(56) References Cited

U.S. PATENT DOCUMENTS 5,571,681 A    11/1996    Janda

FOREIGN PATENT DOCUMENTS

WO    WO 97/40141    * 10/1997
WO    WO 97/47314      12/1997

OTHER PUBLICATIONS

Evans et al., (1996) Nature Biotechnology 14:504–507.
Eichler et al., (1993) Biochemistry 32:11035–11041.
Avalle et al., (1997) Bioorganic & Medicinal Chemistry Letters 7(4):479–484.
Dialog Information Services, Dialog Accession No. 94032215.
STN International, Caplus Accession No. 165868.
Jestin et al., (1999) Angew Chem, Int. Ed. 38(8):1124–1127.
Pedersen et al., (1998) Proc. Natl. Acad. Sci. 95:10523–10528.
Demartis et al., (1999) J. Mol. Biol. 286:617–633.

* cited by examiner

*Primary Examiner*—Andrew Wang
*Assistant Examiner*—Tomas Friend
(74) *Attorney, Agent, or Firm*—Elias Lambiris; Jason Garbell

(57) ABSTRACT

A method for in vitro selection, from a library of catalyst molecules, of a catalyst molecule of interest having a relatively more efficient specific catalytic activity of interest, as compared to the rest of the catalyst molecules within said library, and wherein said in vitro selection method is characterised by that it allows multiple catalytic activity turnovers (i.e. substrate to product catalytic activity turn-overs), by the catalyst molecule of interest, before it is finally collected.

9 Claims, 21 Drawing Sheets

Figure 1:
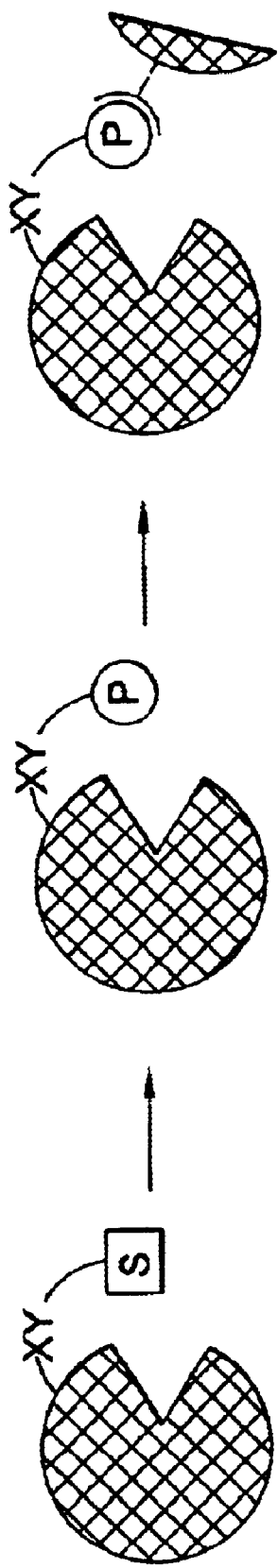

A.

B.

SEQUENCE LISTING

<160> NUMBER OF SEQ ID NOS: 49

<210> SEQ ID NO 1
<211> LENGTH: 378
<212> TYPE: PRT
<213> ORGANISM: Artificial Sequence
<220> FEATURE:
<223> OTHER INFORMATION: Synthetic

<400> SEQUENCE: 1

Met Lys Tyr Leu Leu Pro Thr Ala Ala Ala Gly Leu Leu Leu Leu Ala

```
  1               5              10              15
Ala Gln Pro Ala Met Ala Glu Val Ser Gln Asp Leu Phe Asn Gln Phe
             20              25              30
Asn Leu Phe Ala Gln Tyr Ser Ala Ala Tyr Cys Gly Lys Asn Asn
         35              40              45
Asp Ala Pro Ala Gly Thr Asn Ile Thr Cys Thr Gly Asn Ala Cys Pro
 50              55              60
Glu Val Glu Lys Ala Asp Ala Thr Phe Leu Tyr Ser Phe Glu Asp Ser
 65              70              75              80
Gly Val Gly Asp Val Thr Gly Phe Leu Ala Leu Asp Asn Thr Asn Lys
             85              90              95
Leu Ile Val Leu Ser Phe Arg Gly Ser Arg Ser Ile Glu Asn Trp Ile
             100             105             110
Gly Asn Leu Asn Phe Asp Leu Lys Glu Ile Asn Asp Ile Cys Ser Gly
             115             120             125
Cys Arg Gly His Asp Gly Phe Thr Ser Ser Trp Arg Ser Val Ala Asp
 130             135             140
Thr Leu Arg Gln Lys Val Glu Asp Ala Val Arg Glu His Pro Asp Tyr
 145             150             155             160
Arg Val Val Phe Thr Gly His Ser Leu Gly Gly Ala Leu Ala Thr Val
             165             170             175
Ala Gly Ala Asp Leu Arg Gly Asn Gly Tyr Asp Ile Asp Val Phe Ser
             180             185             190
Tyr Gly Ala Pro Arg Val Gly Asn Arg Ala Phe Ala Glu Phe Leu Thr
             195             200             205
Val Gln Thr Gly Gly Thr Leu Tyr Arg Ile Thr His Thr Asn Asp Ile
 210             215             220
Val Pro Arg Leu Pro Pro Arg Glu Phe Gly Tyr Ser His Ser Ser Pro
 225             230             235             240
Glu Tyr Trp Ile Lys Ser Gly Thr Leu Val Pro Val Thr Arg Asn Asp
             245             250             255
Ile Val Lys Ile Glu Gly Ile Asp Ala Thr Gly Gly Asn Asn Gln Pro
             260             265             270
Asn Ile Pro Asp Ile Pro Ala His Leu Trp Tyr Phe Gly Leu Ile Gly
             275             280             285
Thr Cys Leu Ala Ala Gly Ser Lys Asp Ile Arg Pro Phe Val Cys
 290             295             300
Glu Tyr Gln Gly Gln Ser Ser Asp Leu Pro Gln Pro Pro Val Asn Ala
 305             310             315             320
Gly Gly Gly Ser Gly Gly Ser Gly Gly Ser Glu Gly Gly
             325             330             335
Ser Glu Gly Gly Ser Glu Gly Gly Ser Glu Gly Gly Ser
         340             345             350
Gly Gly Gly Ser Gly Ser Gly Asp Phe Asp Tyr Glu Lys Met Ala Asn
             355             360             365
Ala Asn Lys Gly Ala Met Thr Glu Asn Ala
         370             375

<210> SEQ ID NO 2
<211> LENGTH: 391
<212> TYPE: PRT
<213> ORGANISM: Artificial Sequence
<220> FEATURE:
<223> OTHER INFORMATION: Synthetic
```

<400> SEQUENCE: 2

```
Met Lys Tyr Leu Leu Pro Thr Ala Ala Ala Gly Leu Leu Leu Leu Ala
 1               5                  10                  15
Ala Gln Pro Ala Met Ala Glu Val Ser Gln Asp Leu Phe Asn Gln Phe
             20                  25                  30
Asn Leu Phe Ala Gln Tyr Ser Ala Ala Tyr Cys Gly Lys Asn Asn
         35                  40                  45
Asp Ala Pro Ala Gly Thr Asn Ile Thr Cys Thr Gly Asn Ala Cys Pro
     50                  55                  60
Glu Val Glu Lys Ala Asp Ala Thr Phe Leu Tyr Ser Phe Glu Asp Ser
 65                  70                  75                  80
Gly Val Gly Asp Val Thr Gly Phe Leu Ala Leu Asp Asn Thr Asn Lys
                 85                  90                  95
Leu Ile Val Leu Ser Phe Arg Gly Ser Arg Ser Ile Glu Asn Trp Ile
             100                 105                 110
Gly Asn Leu Asn Phe Asp Leu Lys Glu Ile Asn Asp Ile Cys Ser Gly
         115                 120                 125
Cys Arg Gly His Asp Gly Phe Thr Ser Ser Trp Arg Ser Val Ala Asp
130                 135                 140
Thr Leu Arg Gln Lys Val Glu Asp Ala Val Arg Glu His Pro Asp Tyr
145                 150                 155                 160
Arg Val Val Phe Thr Gly His Ser Leu Gly Gly Ala Leu Ala Thr Val
                165                 170                 175
Ala Gly Ala Asp Leu Arg Gly Asn Gly Tyr Asp Ile Asp Val Phe Ser
            180                 185                 190
Tyr Gly Ala Pro Arg Val Gly Asn Arg Ala Phe Ala Glu Phe Leu Thr
        195                 200                 205
Val Gln Thr Gly Gly Thr Leu Tyr Arg Ile Thr His Thr Asn Asp Ile
210                 215                 220
Val Pro Arg Leu Pro Pro Arg Glu Phe Gly Tyr Ser His Ser Ser Pro
225                 230                 235                 240
Glu Tyr Trp Ile Lys Ser Gly Thr Leu Val Pro Val Thr Arg Asn Asp
                245                 250                 255
Ile Val Lys Ile Glu Gly Ile Asp Ala Thr Gly Gly Asn Asn Gln Pro
            260                 265                 270
Asn Ile Pro Asp Ile Pro Ala His Leu Trp Tyr Phe Gly Leu Ile Gly
        275                 280                 285
Thr Cys Leu Ala Ala Ala Pro Gly Gly Ser His His His His His His
290                 295                 300
Ser Ala Ala Gly Ser Lys Asp Ile Arg Pro Phe Val Cys Glu Tyr Gln
305                 310                 315                 320
Gly Gln Ser Ser Asp Leu Pro Gln Pro Pro Val Asn Ala Gly Gly Gly
                325                 330                 335
Ser Gly Gly Gly Ser Gly Gly Ser Glu Gly Gly Ser Glu Gly
            340                 345                 350
Gly Gly Ser Glu Gly Gly Gly Ser Glu Gly Gly Gly Ser Gly Gly Gly
        355                 360                 365
Ser Gly Ser Gly Asp Phe Asp Tyr Glu Lys Met Ala Asn Ala Asn Lys
370                 375                 380
Gly Ala Met Thr Glu Asn Ala
385                 390
```

<210> SEQ ID NO 3

<211> LENGTH: 2031
<212> TYPE: DNA
<213> ORGANISM: Artificial Sequence
<220> FEATURE:
<223> OTHER INFORMATION: Primer

<400> SEQUENCE: 3

| | | | | | |
|---|---|---|---|---|---|
| atgaaatacc | tattgcctac | ggcagccgct | ggattgttat | tactcgcggc | ccagccggcc | 60 |
| atggcgcagt | ccggcaatcc | gttctctgga | cgtaccttgc | tcgttaacag | cgactacagt | 120 |
| tccaagttgg | accagactcg | acaggctttc | ctgagccgag | gtgatcagac | caacgctgcc | 180 |
| aaggtgaagt | acgttcagga | aaggtcggt | accttctact | ggattagcaa | catcttcctc | 240 |
| ttgcgtgata | tcgacgttgc | tatccagaac | gcacgtgctg | ccaaggcccg | tggagagaat | 300 |
| cccattgttg | gtttggtcct | gtacaacttg | cctgatcgag | attgcagcgc | tggtgagagc | 360 |
| agtggcgagc | tgaagctgag | ccagaacggt | ctcaaccggt | acaagaacga | gtacgtgaat | 420 |
| cccttcgctc | agaagcttaa | ggctgcatcc | gacgtgcagt | cgctgtgat | tctggaaccc | 480 |
| gatgccatcg | gcaacatggt | gaccggcacc | agtgctttct | gccgaaatgc | acggggccct | 540 |
| cagcaagagg | ctatcggcta | cgcgatcagc | cagttgcagg | cctcccacat | tcacctgtac | 600 |
| ctggacgtgg | ccaacggcgg | ttggctcggt | tgggctgaca | agctcgagcc | cactgctcag | 660 |
| gaggtggcta | ctatcctgca | gaaggctggt | aacaatgcga | gatccgcgg | cttcagttcg | 720 |
| aacgtgagca | actacaatcc | ctacagcacc | tccaaccctc | cgccctacac | tagcggttct | 780 |
| ccgtctcctg | acgagtcccg | ctacgctacc | aatatcgcta | cgccatgcg | ccagcgaggc | 840 |
| ttgcccactc | agttcattat | cgatcagagc | cgcgtcgctc | tgtccggagc | ccgtagcgaa | 900 |
| tggggacagt | ggtgcaacgt | gaacccggct | ggtttcggtc | agccgttcac | taccaacacg | 960 |
| aacaatccta | acgtggacgc | gatcgtctgg | gtcaagcctg | aggcgaatc | tgacggtcaa | 1020 |
| tgcggtatgg | gcggtgctcc | cgctgccggc | atgtggttcg | acgcgtatgc | ccaaatgctc | 1080 |
| actcagaatg | ctcacgacga | gatcgcgaga | ggcgctgccg | gttccggtgg | aggcaacaat | 1140 |
| ggcggaggta | caaatccgaa | tcctactccc | accaatccca | cgaatcccgg | tcctacttct | 1200 |
| aaccctggag | gcggtaactg | cgcatccaag | tggggtcagt | gcggaggcca | aggatgggca | 1260 |
| ggacccacct | gttgcgaagc | tggaagcact | tgcacccgtc | agaacgagtg | gtacagccag | 1320 |
| tgcctcccag | gaggcgcggc | cgcaccagga | ggatcacatc | accatcacca | tcactcggcc | 1380 |
| gcaggctcta | agatatcag | accattcgtt | tgtgaatatc | aaggccaatc | gtctgacctg | 1440 |
| cctcaacctc | ctgttaatgc | tggcggcggc | tctggtggtg | gttctggtgg | cggctctgag | 1500 |
| ggtggtggct | ctgagggtgg | cggttctgag | ggtggcggct | ctgagggtgg | cggttccggt | 1560 |
| ggtggctctg | gttccggtga | ttttgattat | gaaaagatgg | caaacgctaa | taaggggggct | 1620 |
| atgaccgaaa | atgccgatga | aaacgcgcta | cagtctgacg | ctaaaggcaa | acttgattct | 1680 |
| gtcgctactg | attacggtgc | tgctatcgac | ggtttcattg | gtgacgtttc | cggccttgct | 1740 |
| aatggtaatg | gtgctactgg | tgattttgct | ggctctaatt | cccaaatggc | tcaagtcggt | 1800 |
| gacggtgata | attcaccttt | aatgaataat | ttccgtcaat | atttaccttc | cctccctcaa | 1860 |
| tcggttgaat | gtcgcccttt | tgtctttggc | gctggtaaac | catatgaatt | ttctattgat | 1920 |
| tgtgacaaaa | taaacttatt | ccgtggtgtc | tttgcgtttc | ttttatatgt | tgccaccttt | 1980 |
| atgtatgtat | tttcgacgtt | tgctaacata | ctgcgtaata | aggagtctta | a | 2031 |

<210> SEQ ID NO 4
<211> LENGTH: 993

<212> TYPE: DNA
<213> ORGANISM: Artificial Sequence
<220> FEATURE:
<223> OTHER INFORMATION: Primer

<400> SEQUENCE: 4

```
atgaaatacc tattgcctac ggcagccgct ggattgttat tactcgcggc ccagccggcc    60
atggcggcga gaggcgctgc cggttccggt ggaggcaaca atggcggagg taacaatccg   120
aatcctactc ccaccaatcc cacgaatccc ggtcctactt ctaaccctgg aggcggtaac   180
tgcgcatcca agtggggtca gtgcggaggc caaggatggg caggacccac ctgttgcgaa   240
gctggaagca cttgcacccg tcagaacgag tggtacagcc agtgcctccc aggaggcgcg   300
gccgcaccag gaggatcaca tcaccatcac catcactcgg ccgcaggctc taaagatatc   360
agaccattcg tttgtgaata tcaaggccaa tcgtctgacc tgcctcaacc tcctgttaat   420
gctggcggcg gctctggtgg tggttctggt ggcggctctg agggtggtgg ctctgagggt   480
ggcggttctg agggtggcgg ctctgagggt ggcggttccg gtggtggctc tggttccggt   540
gattttgatt atgaaaagat ggcaaacgct aataaggggg ctatgaccga aaatgccgat   600
gaaaacgcgc tacagtctga cgctaaaggc aaacttgatt ctgtcgctac tgattacggt   660
gctgctatcg acggtttcat tggtgacgtt tccggccttg ctaatggtaa tggtgctact   720
ggtgattttg ctggctctaa ttcccaaatg gctcaagtcg gtgacggtga taattcacct   780
ttaatgaata atttccgtca atatttacct tccctcccte aatcggttga atgtcgccct   840
tttgtctttg cgctggtaa accatatgaa ttttctattg attgtgacaa aataaactta   900
ttccgtggtg tcttttgcgtt tcttttatat gttgccacct ttatgtatgt attttcgacg   960
tttgctaaca tactgcgtaa taaggagtct taa                                993
```

<210> SEQ ID NO 5
<211> LENGTH: 13
<212> TYPE: DNA
<213> ORGANISM: Artificial Sequence
<220> FEATURE:
<223> OTHER INFORMATION: Primer

<400> SEQUENCE: 5

```
ggggttgttc ccc                                                       13
```

<210> SEQ ID NO 6
<211> LENGTH: 15
<212> TYPE: DNA
<213> ORGANISM: Artificial Sequence
<220> FEATURE:
<223> OTHER INFORMATION: Primer

<400> SEQUENCE: 6

```
ggaagggatg gtcac                                                     15
```

<210> SEQ ID NO 7
<211> LENGTH: 10
<212> TYPE: DNA
<213> ORGANISM: Artificial Sequence
<220> FEATURE:
<223> OTHER INFORMATION: Primer

<400> SEQUENCE: 7

```
accatcatcc                                                           10
```

<210> SEQ ID NO 8

```
<211> LENGTH: 10
<212> TYPE: DNA
<213> ORGANISM: Artificial Sequence
<220> FEATURE:
<223> OTHER INFORMATION: Primer

<400> SEQUENCE: 8
gtgaatccct                                                                  10

<210> SEQ ID NO 9
<211> LENGTH: 46
<212> TYPE: PRT
<213> ORGANISM: Artificial Sequence
<220> FEATURE:
<223> OTHER INFORMATION: Synthetic

<400> SEQUENCE: 9
```

Cys Gly Gly Ser Gly Gly Ser Gly Gly Ser Gly Gly Ser Ala Gln Leu
 1               5                  10                  15

Lys Lys Lys Leu Gln Ala Leu Lys Lys Lys Asn Ala Gln Leu Lys Trp
            20                  25                  30

Lys Leu Gln Ala Leu Lys Lys Lys Leu Ala Gln Gly Gly Cys
        35                  40                  45

```
<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
acaactttca acggcgccag tttcagcgg                                             29

<210> SEQ ID NO 11
<211> LENGTH: 39
<212> TYPE: PRT
<213> ORGANISM: Artificial Sequence
<220> FEATURE:
<223> OTHER INFORMATION: Synthetic

<400> SEQUENCE: 11
```

Gly Ala Ala Gln Leu Glu Lys Glu Leu Gln Ala Leu Glu Lys Glu Asn
 1               5                  10                  15

Ala Gln Leu Glu Trp Glu Leu Gln Ala Leu Glu Lys Glu Leu Ala Gln
            20                  25                  30

Gly Gly Cys Pro Ala Gly Ala
        35

```
<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
actacaaatt ggcgccgctc agctcgaaaa agagc                                      35

<210> SEQ ID NO 13
<211> LENGTH: 47
<212> TYPE: DNA
<213> ORGANISM: Artificial Sequence
<220> FEATURE:
<223> OTHER INFORMATION: Primer
```

<400> SEQUENCE: 13
aattataggc gccagccggg caaccgccct gagccagttc cttttcc     47

<210> SEQ ID NO 14
<211> LENGTH: 42
<212> TYPE: DNA
<213> ORGANISM: Artificial Sequence
<220> FEATURE:
<223> OTHER INFORMATION: Primer

<400> SEQUENCE: 14
cgcgaattgg cccagccggc catggccgca acttcaacta aa     42

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
gcgaattggt gcggccgctt gacctgaatc agcgttg     37

<210> SEQ ID NO 16
<211> LENGTH: 69
<212> TYPE: DNA
<213> ORGANISM: Artificial Sequence
<220> FEATURE:
<223> OTHER INFORMATION: Primer

<400> SEQUENCE: 16
gtcacagatc ctcgcgaatt ggcccagccg gccatggccg aggtctcgca ggatctgttt     60
aaccagttc     69

<210> SEQ ID NO 17
<211> LENGTH: 62
<212> TYPE: DNA
<213> ORGANISM: Artificial Sequence
<220> FEATURE:
<223> OTHER INFORMATION: Primer

<400> SEQUENCE: 17
cagtcacaga tcctcgcgaa ttggtgcggc cgcaagacat gtcccaatta acccgaagta     60
cc     62

<210> SEQ ID NO 18
<211> LENGTH: 11
<212> TYPE: DNA
<213> ORGANISM: Artificial Sequence
<220> FEATURE:
<223> OTHER INFORMATION: Primer

<400> SEQUENCE: 18
gggaagaacc c     11

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ggaagggatg gtcacatgca                                                20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gtcagttgcc aagcttaccg                                                20

<210> SEQ ID NO 21
<211> LENGTH: 69
<212> TYPE: DNA
<213> ORGANISM: Artificial Sequence
<220> FEATURE:
<223> OTHER INFORMATION: Primer

<400> SEQUENCE: 21
ggaagggatg gtcacatgca ctagttaggc tagctacaac gatttttccc ggtaagcttg    60
gcaactgac                                                            69

<210> SEQ ID NO 22
<211> LENGTH: 15
<212> TYPE: RNA
<213> ORGANISM: Artificial Sequence
<220> FEATURE:
<223> OTHER INFORMATION: Primer

<400> SEQUENCE: 22
ggaaaaagua acuag                                                     15

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ttagtgtctc accatcatcc                                                20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ttagtgtctc gtgaatccct                                                20

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25
gccgaagcgc aatgaagggc aacccg                                         26

<210> SEQ ID NO 26
<211> LENGTH: 16

```
<212> TYPE: DNA
<213> ORGANISM: Artificial Sequence
<220> FEATURE:
<223> OTHER INFORMATION: Primer

<400> SEQUENCE: 26
cgggttgccc ttcatt                                                    16

<210> SEQ ID NO 27
<211> LENGTH: 16
<212> TYPE: DNA
<213> ORGANISM: Artificial Sequence
<220> FEATURE:
<223> OTHER INFORMATION: Primer

<400> SEQUENCE: 27
ttcattgcgc ttcggc                                                    16

<210> SEQ ID NO 28
<211> LENGTH: 18
<212> TYPE: PRT
<213> ORGANISM: Artificial Sequence
<220> FEATURE:
<223> OTHER INFORMATION: Synthetic

<400> SEQUENCE: 28

Ile Glu Leu Ser Glu Pro Ile Gly Asn Thr Val Cys His His His His
 1               5                  10                  15
His His

<210> SEQ ID NO 29
<211> LENGTH: 12
<212> TYPE: RNA
<213> ORGANISM: Artificial Sequence
<220> FEATURE:
<223> OTHER INFORMATION: Primer

<400> SEQUENCE: 29
agcugucacu cc                                                        12

<210> SEQ ID NO 30
<211> LENGTH: 12
<212> TYPE: DNA
<213> ORGANISM: Artificial Sequence
<220> FEATURE:
<223> OTHER INFORMATION: Primer

<400> SEQUENCE: 30
agctgtcact cc                                                        12

<210> SEQ ID NO 31
<211> LENGTH: 42
<212> TYPE: DNA
<213> ORGANISM: Artificial Sequence
<220> FEATURE:
<223> OTHER INFORMATION: Primer

<400> SEQUENCE: 31
ggccgcacca ggaggaggat cacatcacca tcaccatcac tc                       42

<210> SEQ ID NO 32
<211> LENGTH: 39
<212> TYPE: DNA
<213> ORGANISM: Artificial Sequence
<220> FEATURE:
<223> OTHER INFORMATION: Primer
```

<400> SEQUENCE: 32
ggccgagtga tggtgatggt gatgtgatcc tcctggtgc                                    39

<210> SEQ ID NO 33
<211> LENGTH: 26
<212> TYPE: DNA
<213> ORGANISM: Artificial Sequence
<220> FEATURE:
<223> OTHER INFORMATION: Primer

<400> SEQUENCE: 33
attaaattag cgcaatgaag ggcaac                                                  26

<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34
aataaataaa cgggttgccc ttcatt                                                  26

<210> SEQ ID NO 35
<211> LENGTH: 26
<212> TYPE: DNA
<213> ORGANISM: Artificial Sequence
<220> FEATURE:
<223> OTHER INFORMATION: Primer

<400> SEQUENCE: 35
ttcattgcgc ttcggcaaat aaataa                                                  26

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Ala Pro Gly Gly Ser His His His His His His Ser
 1               5                  10

<210> SEQ ID NO 37
<211> LENGTH: 35
<212> TYPE: DNA
<213> ORGANISM: Artificial Sequence
<220> FEATURE:
<223> OTHER INFORMATION: Primer

<400> SEQUENCE: 37
cgacatgcca tggcgcagtc cggcaatccg ttctc                                        35

<210> SEQ ID NO 38
<211> LENGTH: 48
<212> TYPE: DNA
<213> ORGANISM: Artificial Sequence
<220> FEATURE:
<223> OTHER INFORMATION: Primer

<400> SEQUENCE: 38
cctttagagc ctgcggccgc gcctcctggg aggcactggc tgtaccac                          48

<210> SEQ ID NO 39
<211> LENGTH: 41
<212> TYPE: DNA
<213> ORGANISM: Artificial Sequence
<220> FEATURE:
<223> OTHER INFORMATION: Primer

<400> SEQUENCE: 39
gctgtgattc tggaacccgc ggccatcggc aacatggtga c          41

<210> SEQ ID NO 40
<211> LENGTH: 48
<212> TYPE: DNA
<213> ORGANISM: Artificial Sequence
<220> FEATURE:
<223> OTHER INFORMATION: Primer

<400> SEQUENCE: 40
cctttagagc ctgcggccgc gcctcctggg aggcactggc tgtaccac    48

<210> SEQ ID NO 41
<211> LENGTH: 41
<212> TYPE: DNA
<213> ORGANISM: Artificial Sequence
<220> FEATURE:
<223> OTHER INFORMATION: Primer

<400> SEQUENCE: 41
gtcaccatgt tgccgatggc cgcgggttcc agaatcacag c           41

<210> SEQ ID NO 42
<211> LENGTH: 35
<212> TYPE: DNA
<213> ORGANISM: Artificial Sequence
<220> FEATURE:
<223> OTHER INFORMATION: Primer

<400> SEQUENCE: 42
cgacatgcca tggcggcgag aggcgctgcc ggttc                 35

<210> SEQ ID NO 43
<211> LENGTH: 48
<212> TYPE: DNA
<213> ORGANISM: Artificial Sequence
<220> FEATURE:
<223> OTHER INFORMATION: agcgcaatga agggca
      16

<400> SEQUENCE: 43
cgtacgatcg tagccgaagc gcaatgaagg gcaacccggt acgatcgt    48

<210> SEQ ID NO 44
<211> LENGTH: 16
<212> TYPE: DNA
<213> ORGANISM: Artificial Sequence
<220> FEATURE:
<223> OTHER INFORMATION: ttcattgcgc ttcggc
      16

<400> SEQUENCE: 44
cgggttgccc ttcatt                                      16

<210> SEQ ID NO 45
<211> LENGTH: 16
<212> TYPE: DNA
<213> ORGANISM: Artificial Sequence
<220> FEATURE:

```
<223> OTHER INFORMATION: Primer

<400> SEQUENCE: 45
cgggttgccc ttcatt                                                      16

<210> SEQ ID NO 46
<211> LENGTH: 16
<212> TYPE: DNA
<213> ORGANISM: Artificial Sequence
<220> FEATURE:
<223> OTHER INFORMATION: Primer

<400> SEQUENCE: 46
ttcattgcgc ttcggc                                                      16

<210> SEQ ID NO 47
<211> LENGTH: 16
<212> TYPE: DNA
<213> ORGANISM: Artificial Sequence
<220> FEATURE:
<223> OTHER INFORMATION: Primer

<400> SEQUENCE: 47
agcgcaatga agggca                                                      16

<210> SEQ ID NO 48
<211> LENGTH: 11
<212> TYPE: DNA
<213> ORGANISM: Artificial Sequence
<220> FEATURE:
<223> OTHER INFORMATION: Primer

<400> SEQUENCE: 48
tgcccttcat t                                                           11

<210> SEQ ID NO 49
<211> LENGTH: 11
<212> TYPE: DNA
<213> ORGANISM: Artificial Sequence
<220> FEATURE:
<223> OTHER INFORMATION: Primer

<400> SEQUENCE: 49
ttcattgcgc t                                                           11
```

ENZYME ACTIVITY SCREEN WITH DIRECT SUBSTRATE REPLACEMENT

CROSS-REFERENCE TO RELATED APPLICATIONS

This application is a continuation of PCT/DK99/00441 filed Aug. 19, 1999 and claims priority under 35 U.S.C. 119 of Danish applications PA 1998 01044 filed Aug. 19, 1998 and PA 1998 01106 filed Sep. 2, 1998, the contents of which are fully incorporated herein by reference.

TECHNICAL FIELD

The present invention relates to a library of catalysts of interest coupled to a substrate by an exchangeable linker pair, X and Y, and a selection method that uses multiple catalytic turnover events to isolate the more active of the catalysts in said library.

BACKGROUND OF THE INVENTION

In the past, novel biopolymer (i.e. DNA, RNA or polypeptide) based catalysts have been created in several different ways. The following paragraphs describe some of these selection schemes.

(1). Binding to Transition State Analogs

Catalytic RNA, DNA and protein (particularly antibodies) have been isolated by this approach. It has mostly been applied to the isolation of catalytic antibodies by immunization of mice with transition state analogs (TSA), also antibodies displayed on phage as well as RNA and DNA libraries have been challenged with TSA. The idea is that a molecule (protein, RNA or DNA) that binds a given TSA is likely to bind the substrate and stabilize the geometry and/or energetics of the transition state. This may result in catalysis.

The method does not select for catalytic activity per se, but rather for binding to a transition state analog (TSA). However, it has been included here as it is currently one of the most used methods to isolate novel catalysts. Problems encountered with this approach include: i) Detailed mechanistic knowledge of the target reaction is required (in order to design an appropriate TSA); ii) In many cases a TSA that adequately resembles the transition state is unobtainable or unstable; iii) It is not possible to mimic the structural and electronic dynamics of the reaction coordinate.

Consequently, a rather limited set of reaction types have been successfully targeted by this approach. In most cases the isolated catalysts have poor turn-over numbers.

(2). Functional Tagging of Active Catalysts

This selection scheme has been applied to protein and nucleic acids. The substrate is designed so that a reactive product is formed during the reaction (the substrate is called "suicide substrate" or "inhibitor analog"). The reactive product is likely to react with the catalyst that produced it, to form a covalent bond. As a result, active catalysts can be separated from inactive ones by way of the attached label. Catalytic antibodies displayed on phage have been isolated by this method, and it was shown in a model system that catalytically active and inactive proteins could be separated using this approach. The method should allow the isolation of rare catalysts.

Important limitations with this approach include: i) For many reactions it is not possible to design an appropriate suicide substrate. ii) Successful catalysts need only perform one turn-over during the selective process/round, which is typically on the order of minutes. Hence, there is no selective advantage for efficient catalysts.

(3). Continuous Evolution (RNA)

RNA libraries have been designed that contain both the substrate and the potentially catalytic domain in the same molecule. RNAs capable of performing the desired reaction (typically ligation) will "activate" themselves for amplification (reverse transcription followed by RNA polymerase transcription). By adequate dilutions and additions of nucleotide precursors this continuous selection can be maintained over several hours, and then analyzed.

The method has two important limitations: i) Both the substrate and the catalyst must be a nucleic acid; ii) As the catalyzed reaction and the amplification of successful enzymes is not separated, the time of the selective step is the sum of the turn-over time of the target reaction and the time of amplification of the "activated" molecules. Thus, as the amplification is on the order of seconds, there is no selective advantage for an efficient catalyst.

(4). Substrate-Enzyme-Linked Selection (SELS)

Recently, methods have been described, involving the attachment of the substrate of the target reaction to a protein with potential catalytic activity towards the attached substrate (Pedersen et al., Proc. Natl. Acad. Sci., US, 1998, vol. 95, pp. 10523–10528; Jestin et al., 1999, Angew. Chem. Int. Ed., vol. 38, pp. 1124–1127; Demartis et al., 1999, JMB, vol. 286, pp. 617–633; Neri et al., 1997, WO 97/40141). Upon intramolecular conversion of the substrate, the active catalyst can be isolated by means of the attached product.

This scheme is very general. However, since successful catalysts need only perform one turn-over during the selective process/round, which is typically in the order of minutes, there is no selective advantage for efficient catalysts. For the same reason, it presumably is not possible to distinguish enzymes with slightly different specific activity with this selection scheme.

SUMMARY OF THE INVENTION

The problem to be solved by the present invention is to provide a method for in vitro selection, from a library of catalyst molecules, of a catalyst molecule of interest having a relatively more efficient specific catalytic activity of interest, as compared to the rest of the catalyst molecules within said library, and wherein said in vitro selection method is characterised by that it allows multiple catalytic activity turn-overs (i.e. substrate to product catalytic activity turn-overs), by the catalyst molecule of interest, before it is finally collected.

The solution is based on using a novel sample comprising a number of individual units in said in vitro selection method.

A summary of the characteristics of said novel sample is given immediately below.

Said novel sample comprises a library of catalyst molecules provided in the form of individual units, wherein the individual units comprise a first type individual unit having the following general structure:

C—XY—S, wherein C denotes a catalyst molecule, XY an XY exchange pair, and S a substrate which is capable of being catalysed into a product by at least one catalyst comprised within said library of catalyst molecules and thereby providing the possibility of obtaining a second type individual unit comprising the general structure:

C—XY—P, wherein C and XY has the meaning defined above and P is the product molecule resulting from the catalytic conversion of the substrate S of the first type individual unit. See FIG. 1 for a graphic illustration of a suitable example of such an individual unit.

Said novel sample, is then characterised by that it comprises following functionally defined features:

Feature 1:

The substrate S is attached to the catalyst in a configuration that allows catalytic reaction between the catalyst and the substrate within said individual unit; and the nature of said attachment of the substrate and the catalyst provides the possibility, by means of a characteristic of the product, of isolating an entity comprising information allowing the unambiguous identification of the catalyst molecule which has been capable of catalysing the reaction substrate molecule to product molecule.

For illustration reference is made to FIG. 1, where is shown a suitable example of such an individual unit comprising feature 1 above.

Feature 2:

Said sample comprising a number of individual units and comprising feature 1 above is further characterised by that said XY exchange pair allows an asymmetric exchange of the Y-moiety with another Y-moiety (i.e. Y exchanges with Y, not with X); whereby said XY exchange pair then allows an exchange reaction between the unit structure:

a catalyst—an XY exchange pair—a product and a "Y—substrate" component and thereby generating the unit structure a catalyst—an XY exchange pair—a substrate.

Figure 2:
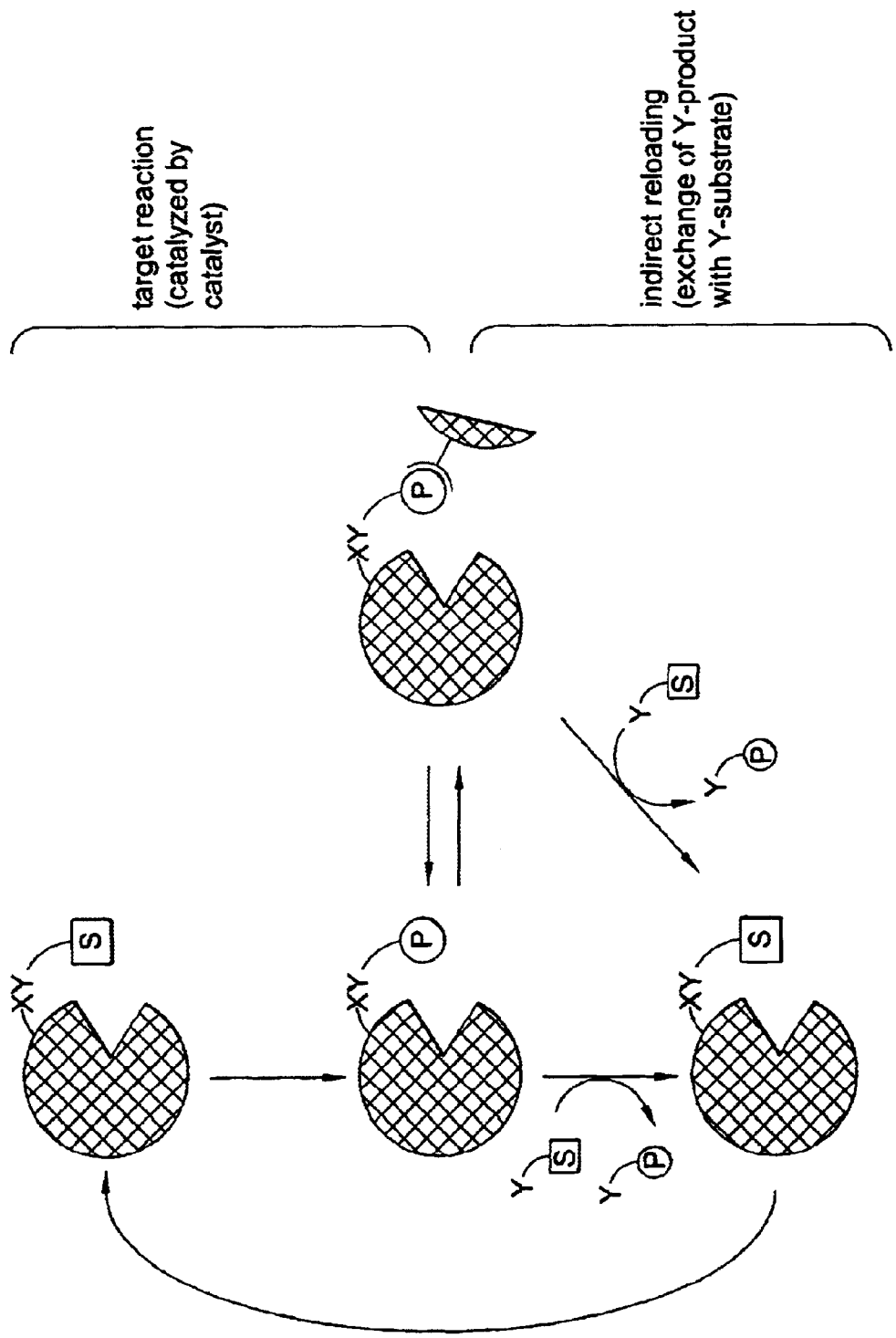

For illustration reference is made to FIG. 2, where is shown a suitable example of such an individual unit comprising feature 2 above.

Using such a novel sample in a in vitro selection method as described herein (vide infra), provides then the possibility of selecting a catalyst molecule of interest essentially only based on a characteristic of the product molecule which has been generated by the catalyst molecule of interest (Feature 1 allows this; see FIG. 1 for an illustration);

and it further provides the possibility of selecting a catalyst molecule of interest having a relatively more efficient specific catalytic activity of interest, as compared to the rest of the catalyst molecules within said library, and wherein said selection is characterised by that said catalyst molecule of interest is first finally collected after it has been allowed to perform multiple catalytic activity turn-overs (i.e. substrate to product catalytic activity turn-overs) (Feature 2 allows this; see FIG. 2 for an illustration).

Accordingly, a first aspect of the invention relates to a sample comprising a number of individual units suitable for use in an in vitro selection system, wherein the purpose of said in vitro selection system is, from a library of catalyst molecules, to select a catalyst molecule of interest having a relatively more efficient specific catalytic activity of interest as compared to the rest of the catalyst molecules within said library, and wherein said in vitro selection system is characterised by that it allows multiple catalytic activity turn-overs (i.e. substrate to product catalytic activity turn-overs), by the catalyst molecule of interest, before it is finally collected and wherein said sample comprises, (i) a library of catalyst molecules provided in the form of individual units, wherein the individual units comprise a first type individual unit having the following general structure:

C—XY—S, wherein C denotes a catalyst molecule, XY an XY exchange pair, and S a substrate which is capable of being catalysed into a product by at least one catalyst comprised within said library of catalyst molecules and thereby providing the possibility of obtaining a second type individual unit comprising the general structure:

C—XY—P, wherein C and XY has the meaning defined above and P is the product molecule resulting from the catalytic conversion of the substrate S of the first type individual unit; and (a) the substrate S is attached to the catalyst in a configuration that allows catalytic reaction between the catalyst and the substrate within said individual unit; and (b) the nature of said attachment of the substrate and the catalyst provides the possibility, by means of a characteristic of the product, of isolating an entity comprising information allowing the unambiguous identification of the catalyst molecule which has been capable of catalysing the reaction substrate molecule to product molecule; and (c) said sample comprising a number of individual units is characterised by that said XY exchange pair allows an asymmetric exchange of the Y-moiety with another Y-moiety (i.e. Y exchanges with Y, not with X); whereby said XY exchange pair then allows an exchange reaction between the unit structure:

a catalyst—an XY exchange pair—a product and a "Y—substrate" component and thereby generating the unit structure a catalyst—an XY exchange pair—a substrate.

The term "an individual unit", comprised within a sample according to the first aspect as described above, denotes an individual unit comprising the general structure as specified under point (i) in the first aspect of the invention; a substrate molecule attached to a catalyst molecule as specified under point (a) and (b) in the first aspect of the invention; and an XY exchange pair as specified under point (c) in the first aspect of the invention. See FIGS. 1 and 2 for a suitable example of such an individual unit.

The term "an individual unit comprising the general structure: a catalyst—an XY exchange pair—a substrate; or a catalyst—an XY exchange pair—a product" denotes that said individual unit comprises at least one molecule of each of said entities, i.e. at least one catalyst molecule, at least one XY exchange pair molecule, and at least one substrate molecule or at least one product molecule. Accordingly, said individual unit may for instance comprise more than one copy of an identical catalyst molecule or may comprise several different catalyst molecules.

Further the term "—" placed between the individual entities within said individual unit denotes that there is a physical connection between said individual entities within said individual unit, i.e. that there is a physical connection between a catalyst—an XY exchange pair—a substrate or a catalyst—an XY exchange pair—a product.

Further, "an individual unit" as described herein denotes an individual unit wherein it is possible to physically separate said individual unit from the other different individual units, within said sample, in order to be able to isolate the separate individual unit.

The term "different individual units" denotes different individual units each independently comprising different catalyst molecules, i.e. an example of two different individual units may be (1) catalyst molecule$^1$—XY exchange pair—substrate; and (2) catalyst molecule$^2$—XY exchange pair—substrate; wherein catalyst molecule$^1$ and catalyst molecule$^2$ denotes two different catalyst molecules.

The term "a sample comprising a number of different individual units" denotes a sample comprising at least two different individual units, preferably at least 100 different individual units, more preferably at least 10.000 different individual units, more preferably at least $10^6$ different individual units, more preferably at least $10^8$ different individual units, more preferably at least $10^{10}$ different individual units, even more preferably at least $10^{12}$ different individual units, and most preferably at least $10^{14}$ different individual units. Basically the actual number of different individual units corresponds to the actual size of the library of catalyst molecules.

The term "a sample comprising a number of individual units" and the term "a sample comprising a number of different individual units" may be used interchangeably herein.

The term "a library of catalyst molecules" denotes a library comprising at least two different catalyst molecules, preferably at least 100 different catalyst molecules, more preferably at least 10.000 different catalyst molecules, more preferably at least $10^6$ different catalyst molecules, more preferably at least $10^8$ different catalyst molecules, more preferably at least $10^{10}$ different catalyst molecules, even more preferably at least $10^{12}$ different catalyst molecules, and most preferably at least $10^{14}$ different catalyst molecules.

The term "a substrate capable of being catalysed into a product molecule by at least one catalyst molecule comprised within said library of catalyst molecules" basically denotes any suitable substrate molecule. Essentially said substrate molecule is chosen according to the specific catalytic activity which it is desired to select for. For instance, if the desired catalytic activity is a protease activity then a suitable substrate may be a peptide molecule and the product will then be a degraded peptide. The terms "substrate" and "substrate molecule" may be used interchangeably.

The term "product" denotes the product obtained by the catalytic reaction substrate to product by a catalyst of interest as specified herein. The terms "product" and "product molecule" may be used interchangeably.

The term "catalyst" denotes any catalyst molecule with a desired catalytic activity, such as organic and inorganic molecules, proteins, enzymes, peptides, nucleic acids, biopolymers and non-biological polymers, small organic or inorganic molecules. The terms "catalyst" and "catalyst molecule" may be used interchangeably.

The term "the substrate is attached to the catalyst in a configuration that allows catalytic reaction between the catalyst and the substrate within said individual unit" denotes a direct or indirect physical connection, within each of the individual units, between substrate and catalyst. This connection should preferably maximize productive interaction of the catalyst and the substrate, within the individual unit, while minimizing the interaction of catalysts and substrates on different individual units.

The term "the nature of said attachment of the substrate and the catalyst provides the possibility, by means of a characteristic of the product, of isolating an entity comprising information allowing the unambiguous identification of the catalyst molecule which has been capable of catalysing multiple times the reaction substrate molecule to product molecule" according to point (b) of the first aspect of the invention denotes that said entity is isolated by means of one or more characteristic of the product.

An example of a suitable characteristic of the product may be that said product does not bind to a matrix and the substrate does bind to a matrix. In this case a suitable selection protocol may be that the individual units are bound to the solid support on the form a catalyst—an XY exchange pair—a substrate—matrix, and released when it is on the form catalyst—an XY exchange pair—a product. For a detailed description of an example of such a system reference is made to a working example herein (vide infra).

Another example of a suitable characteristic of the product may be that said product binds to a receptor as illustrated in FIG. 1.

The term "an entity comprising information allowing the unambiguous identification of the catalyst molecule which has been capable of catalysing the reaction substrate molecule to product molecule" according to point (b) in the first aspect of the invention, denotes either an entity wherein said information is carried in the catalyst molecule as such or an entity comprising other kind of information providing the possibility of unambiguously identifying the catalyst. Such other kind off information may for instance be an entity comprising a DNA sequence encoding a peptide or a polypeptide when the catalyst molecule of interest is a peptide or a polypeptide. An illustration of this may be when the isolated entity is a filamentous phage comprising a DNA sequence encoding a polypeptide of interest attached on the surface of said phage. See e.g. FIG. 12 and below for further details.

The term "XY exchange pair", comprised within an individual unit, as specified above, denotes that the catalyst is attached to a substrate through an XY exchange moiety, i.e., the individual unit has the following general structure: a catalyst—an XY exchange pair—a substrate and said XY exchange pair fulfils the criteria according to point (c) in the first aspect of the invention.

Preferably, the XY moiety is stable in the absence of free Y, but allows fast and specific exchange of free Y with Y bound to X (but not exchange of free Y with X). This exchange reaction can replace product with substrate, if the individual unit: a catalyst—an XY exchange pair—a product is in contact with a Y-Substrate compound.

The XY exchange pair may for instance have following characteristics:

i) X and Y can be covalently or non-covalently bonded; and ii) the XY exchange pair may consist of any kind of molecules, including small organic (eg., EDTA) and inorganic (eg. metals, phosphates) molecules as well as macromolecules (eg., nucleic acids, peptides).

See below for further details and FIGS. 2, 3 and 4 for graphic illustrations.

In a second aspect the invention relates to a method for in vitro selection, from a library of catalyst molecules, of a catalyst molecule of interest having a relatively more efficient specific catalytic activity of interest as compared to the rest of the catalyst molecules within said library and wherein said in vitro selection method is characterised by that it allows multiple catalytic activity turn-overs (i.e. substrate to product catalytic activity turn-overs), by the catalyst molecule of interest, before it is finally collected and wherein said method comprises following steps, (i) placing a sample comprising a number of individual units according to the invention under suitable conditions where a catalyst molecule of interest performs its catalytic activity of interest and further under conditions wherein said individual units are in contact with an Y—substrate compound;

(ii) selecting for a catalyst of interest by selecting for one or more individual unit(s) which comprise(s) the product molecule; and (iii) isolating an entity comprising information allowing the unambiguous identification of the catalyst molecule of interest which has been capable of catalysing multiple times the reaction substrate to product, by means of a characteristic of the product; and optionally (iv) repeating step (i) to (iii) one or more times by using the information comprised in said entity of step (iii) to generate the catalyst molecule of interest and construct an individual unit comprising said generated catalyst molecule of interest and then using this individual unit as a starting material in said repetition step.

The term "under suitable conditions where a catalyst molecule of interest performs its catalytic activity of interest" according to step (i) of the second aspect of the invention, denotes any suitable conditions where a catalyst molecule of interest performs its catalytic activity of interest.

Such suitable conditions may be alkaline pH if the purpose of the selection is to identify a catalyst of interest having activity at alkaline pH.

The term "said individual units are in contact with an Y—substrate compound" according to point (i) in second aspect of the invention denotes that the individual units and the Y—substrate compound are appropriately close that an exchange reaction, as specified under point (c) in the first aspect of the invention, is possible. Said contact may for instance be in a buffer solution wherein the individual units and the Y—substrate compound may diffuse together and thereby get in contact with each other. See FIG. 2 for graphic illustrations.

The term "the catalyst molecule of interest which has been capable of catalysing multiple times the reaction substrate to product" according to step (iii) of the second aspect of the invention denotes that said catalyst molecule of interest has performed the catalytic reaction substrate to product at least two times, more preferably at least 100 times, more preferably at least 10.000 times, even more preferably at least $10^6$ times, and most preferably at least $10^{10}$ times.

The term "an entity comprising information allowing the unambiguous identification of the catalyst molecule of interest" denotes either an entity wherein said information is carried in the catalyst molecule as such or an entity comprising other kind of information providing the possibility of unambiguously identifying the catalyst. Such other kind of information may for instance be an entity comprising a DNA sequence when the catalyst molecule of interest is a peptide or a polypeptide. This is the same definition as described above for the same term in relation to point (b) of the first aspect of the invention (vide supra).

The term "repeating step (i) to (iii) one or more times by using the information comprised in said entity of step (iii) to generate the catalyst molecule of interest and construct an individual unit comprising said generated catalyst molecule of interest and then using this individual unit as a starting material in said repetition step" according to point (iv) in the second aspect of the invention denotes that said repetition may be one time, more preferably 2 times, more preferably more than 5 times, even more preferably more than 10 times, and most preferably more than 25 times.

An advantage of the method for in vitro selection as described above is that it allows the catalyst molecules to perform multiple turn-overs of substrate to product during one selection round (i.e. before the catalyst molecule(s) of interest is finally collected).

This is fundamentally different from selection protocols previously described in the art, which either involved binding to a transition state analog of the target reaction, wherein there is no turn-over of substrate (see #1 in "Background" above) or a single turn-over of substrate (#2 and 3 in "Background" above).

This may provide two advantages, which may be illustrated by following a possible selection scheme using the method of the invention:

a) placing, according to point (i) of the method of second aspect of the invention, the sample comprising a number of individual units under suitable conditions where a catalyst molecule of interest exhibits its catalytic activity of interest and further under conditions wherein said individual units are in contact with an Y—substrate molecule at one end (starting end) of a product-binding column wherein a receptor specifically binding the product is coupled to the matrix of the product-binding column and with a suitable amount of the Y—substrate within the product-column buffer;

b) selecting, according to point (ii) of the method of second aspect of the invention, for a catalyst molecule of interest by selecting for one or more individual unit(s) which comprise(s) the product molecule, by collecting the individual unit(s) which arrive(s) latest to the opposite end (collecting end) of the column.

Within this selection scheme the following events, among others, take place within the product-column:

1) individual units comprising a potential catalyst molecule of interest converts the attached substrate to product;

2) said individual units, now comprising the product, are diffusing to and binding to a receptor placed close to the starting end of the product column;

3) the Y—substrate molecules, within the product-column buffer mediates the exchange reaction catalyst molecule—XY exchange pair—product and a Y—substrate molecule and thereby generating the unit structure catalyst molecule—XY exchange pair—substrate, and thereby mediates release of said bound individual units of step (2) above;

4) said released individual units of step (3) above are now comprising a substrate and a potential catalyst molecule of interests, which has made one catalytic conversion of the substrate to product, and is now regenerated in the original form of the individual units of point 1. Accordingly, said units can therefore once more perform reaction (1); binding to a receptor relatively closer to the collecting end of the product column etc.

The catalyst molecule of interest having most efficient specific catalytic activity of interest will perform most substrate to product conversions in a given time interval, and as a result, will spend more time immobilised on the product-binding receptor. Therefore, the individual unit(s) comprising said most efficient catalyst molecule will arrive latest to the collecting end of said column.

Using this example of a method of the second aspect of the invention, two advantages over the art may be:

i) that the possible "selectable" catalytic activity may be much higher than for the prior art selection protocols. A selective step involves performing the target reaction, diffusion to and binding of product to product-binding column, and finally exchange of product and substrate by the XY-exchange reaction. Since diffusion is generally a fast process, the selection stringency can be controlled simply by the amount of product binding receptor on the column or the type/amount of Y—S component in the product-column buffer; moreover, if for example electrophoresis is used as the means of isolating the more active catalysts, diffusion to the receptor may not be a limiting factor, wherefore the selection stringency may be even higher with this system;

ii) minor differences in activity can be distinguished; Since the selective step is reiterated many times as the catalysts flow through the column, even minor differences in catalyst activity will result in differential retention on the column, and thus differential enrichments.

In a final aspect the invention relates to a method for producing a catalyst molecule of interest comprising performing the method for in vitro selection according to the invention and the further following step, (a) producing said isolated catalyst molecule of interest in a suitable quantity of interest by a suitable production method.

DRAWINGS

FIG. 1: Graphic illustration of a suitable example of a first type individual unit having the following general structure:

C—XY—S, wherein C denotes a catalyst molecule, XY an XY exchange pair, and S a substrate. The substrate S is attached to the catalyst in a configuration that allows catalytic reaction between the catalyst and the substrate within said individual unit. The catalytic reaction results in a second type individual unit:

C—XY—P, wherein C denotes a catalyst molecule, XY an XY exchange pair, and P denotes a product molecule.

The nature of said attachment of the substrate and the catalyst provides the possibility, by means of a characteristic of the product (e.g. binding affinity to a matrix), of isolating an entity (e.g. the catalyst itself or a phage displaying it) comprising information allowing the unambiguous identification of the catalyst molecule which has been capable of catalysing the reaction from substrate molecule to product molecule.

FIG. 2: Graphic illustration of an individual first type unit wherein the XY exchange pair allows an asymmetric exchange of the Y-moiety with another Y-moiety (i.e. Y exchanges with Y, not with X). After the target reaction has taken place (FIG. 1) said XY exchange pair allows an exchange reaction between the second type unit structure:

C—XY—P and an unbound Y—S component, thereby generating anew a first type unit structure C—XY—S and an unbound Y—P component, whereafter the catalyst of this unit can perform yet another catalytic reaction on the freshly bound substrate.

A matrix binding the product, P, would effectively keep Y—P components bound as well as C—XY—P type individual units, until an exchange reaction such as described immediately above occured, effectively releasing the catalyst from the matrix in the form of a freshly generated first type unit C—XY—S leaving the Y—P component behind bound to the matrix.

Figure 3:
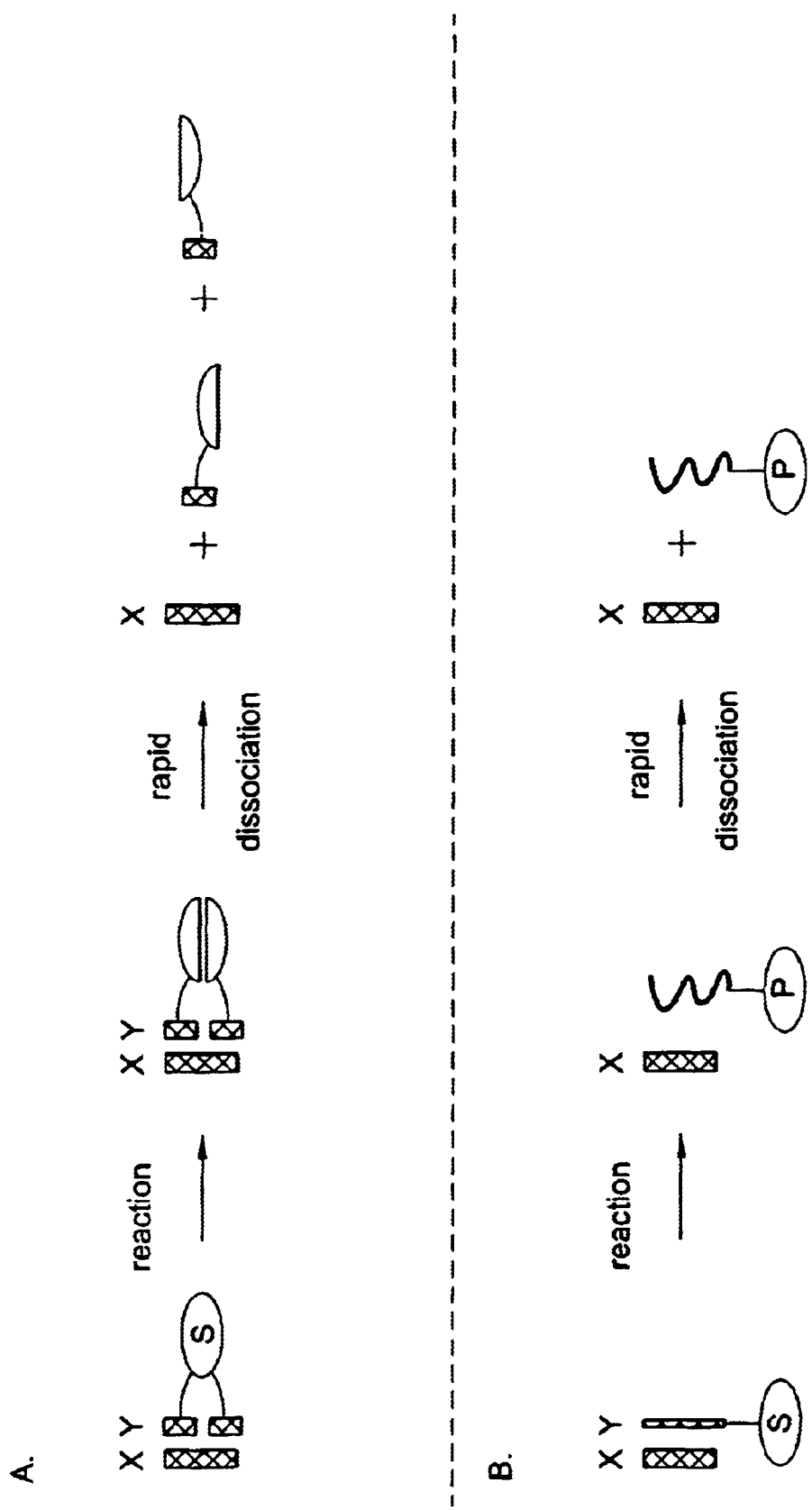
Figure 4:
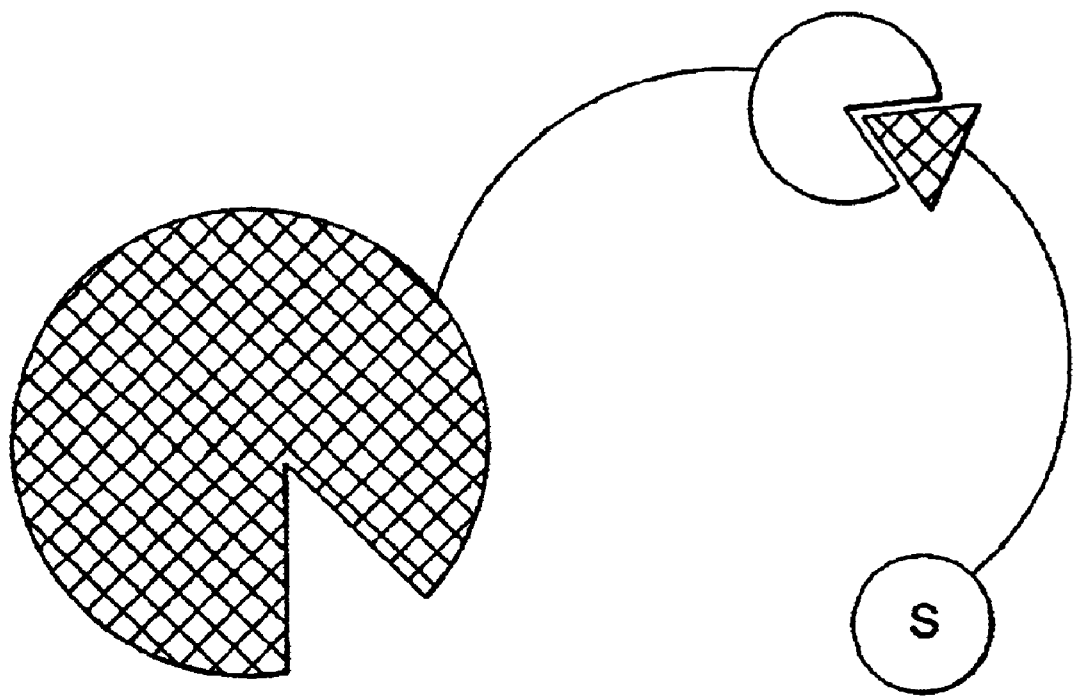

FIG. 3: Graphic illustrations of suitable XY exchange pairs of an individual unit according to the invention. The catalytic reaction facilitates dissociation of X and Y (e.g. X is a DNA strand, Y is a complementary DNA/RNA/DNA hybrid or a DNA/RNA/matrix hybrid, C is an RNase).

Other examples are: Non-covalent bonds between X and Y ($His_4$—Fe—IDA and NTA—Fe—IDA), and covalent bond between X and Y (disulfide). Note that symmetric exchange units (XX) like a disulfide bond can be used as exchange units FIG. 4: Graphic illustration of an individual unit, in which the XY exchange unit is another enzyme-substrate pair.

Figure 5:
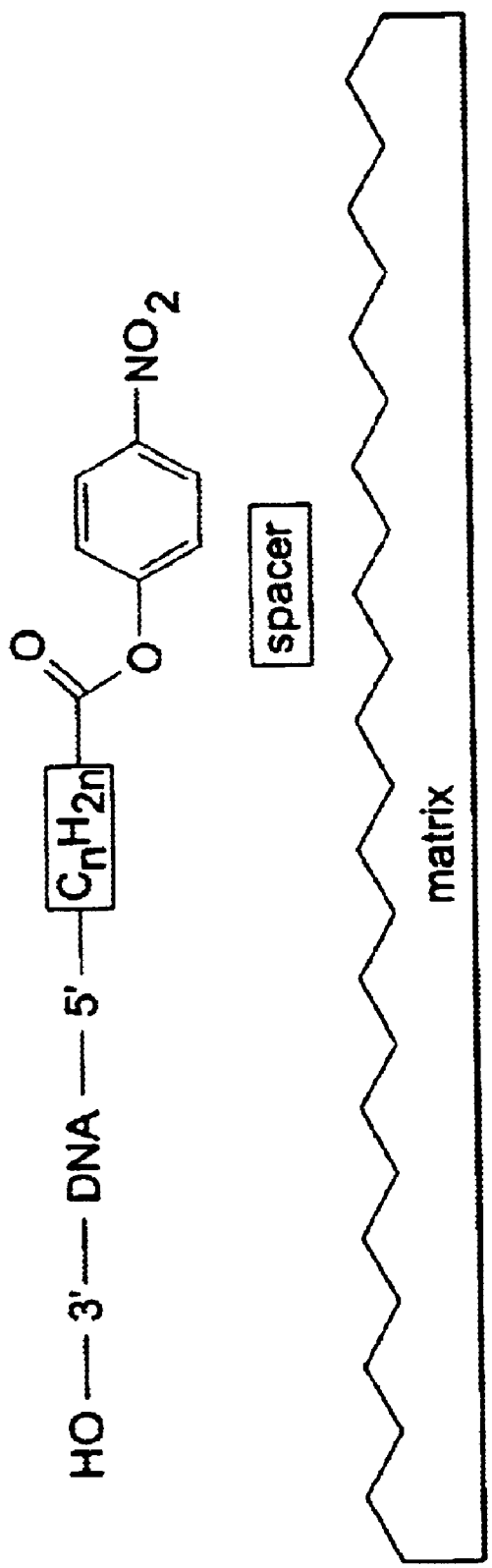

FIG. 5: Graphic illustration of the Y-substrate molecule described in example 2 below.

Figure 6:
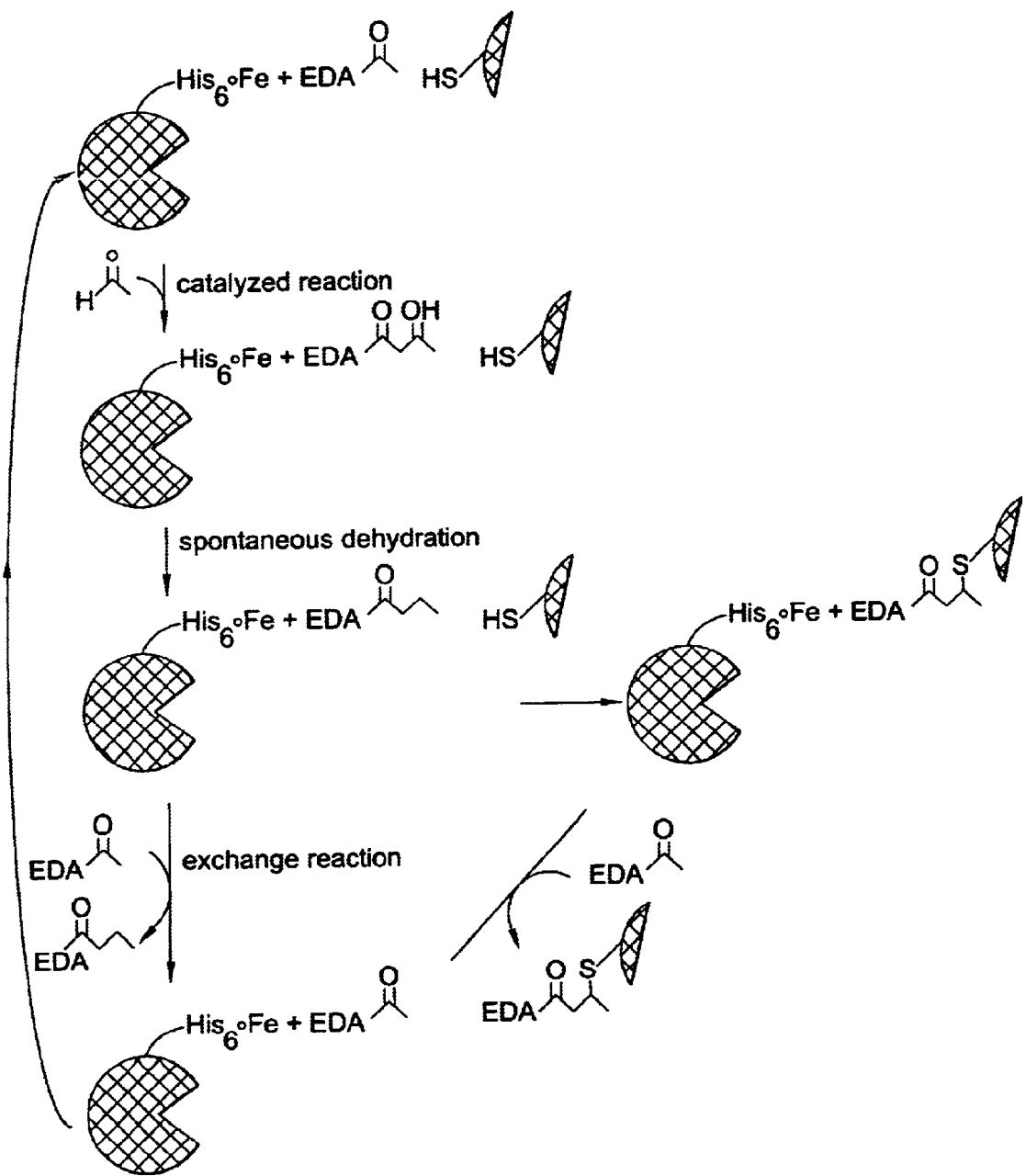

FIG. 6: Graphic illustration of the selection scheme described in example 4 below. Optimization of an enzyme that catalyzes aldol formation.

Figure 7:
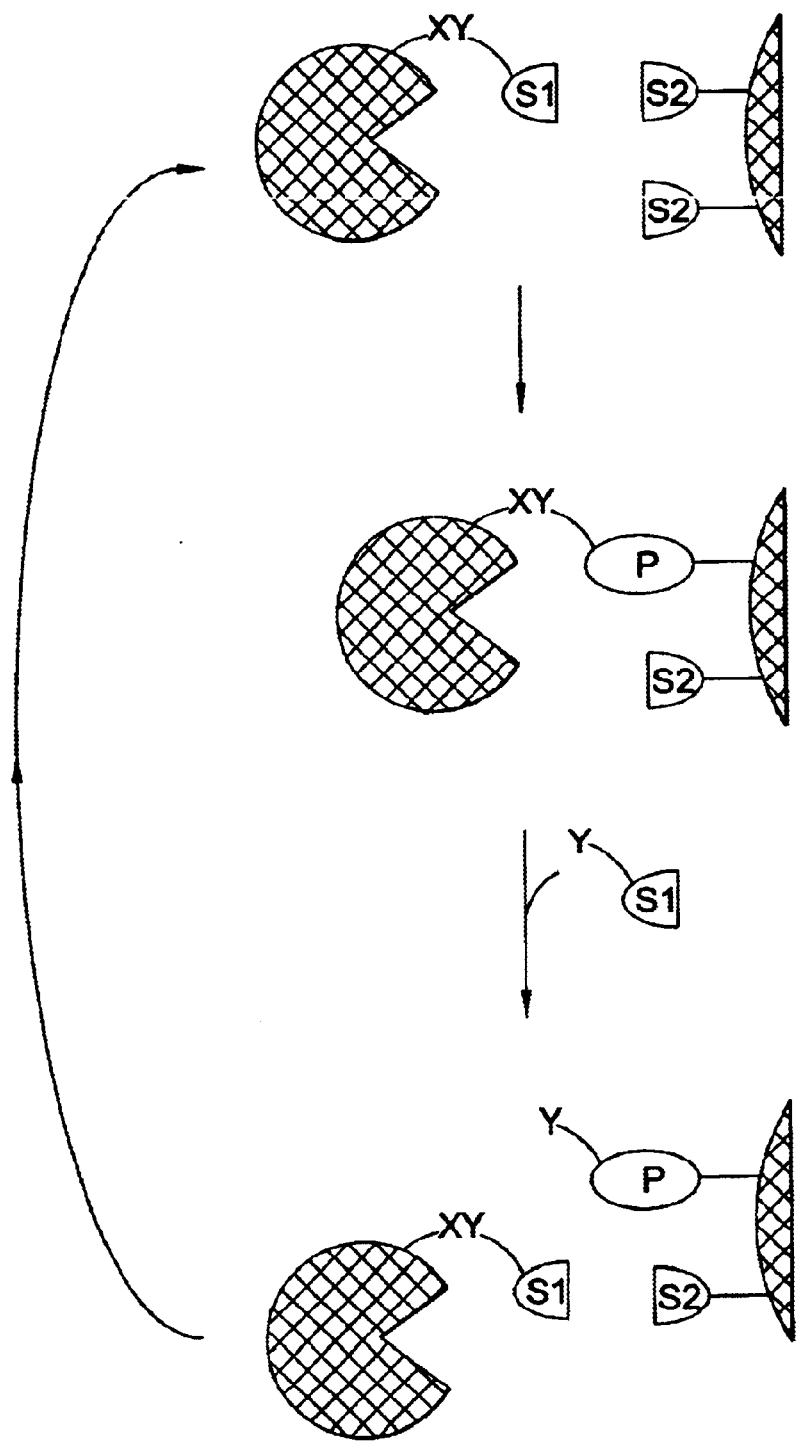
Figure 8:
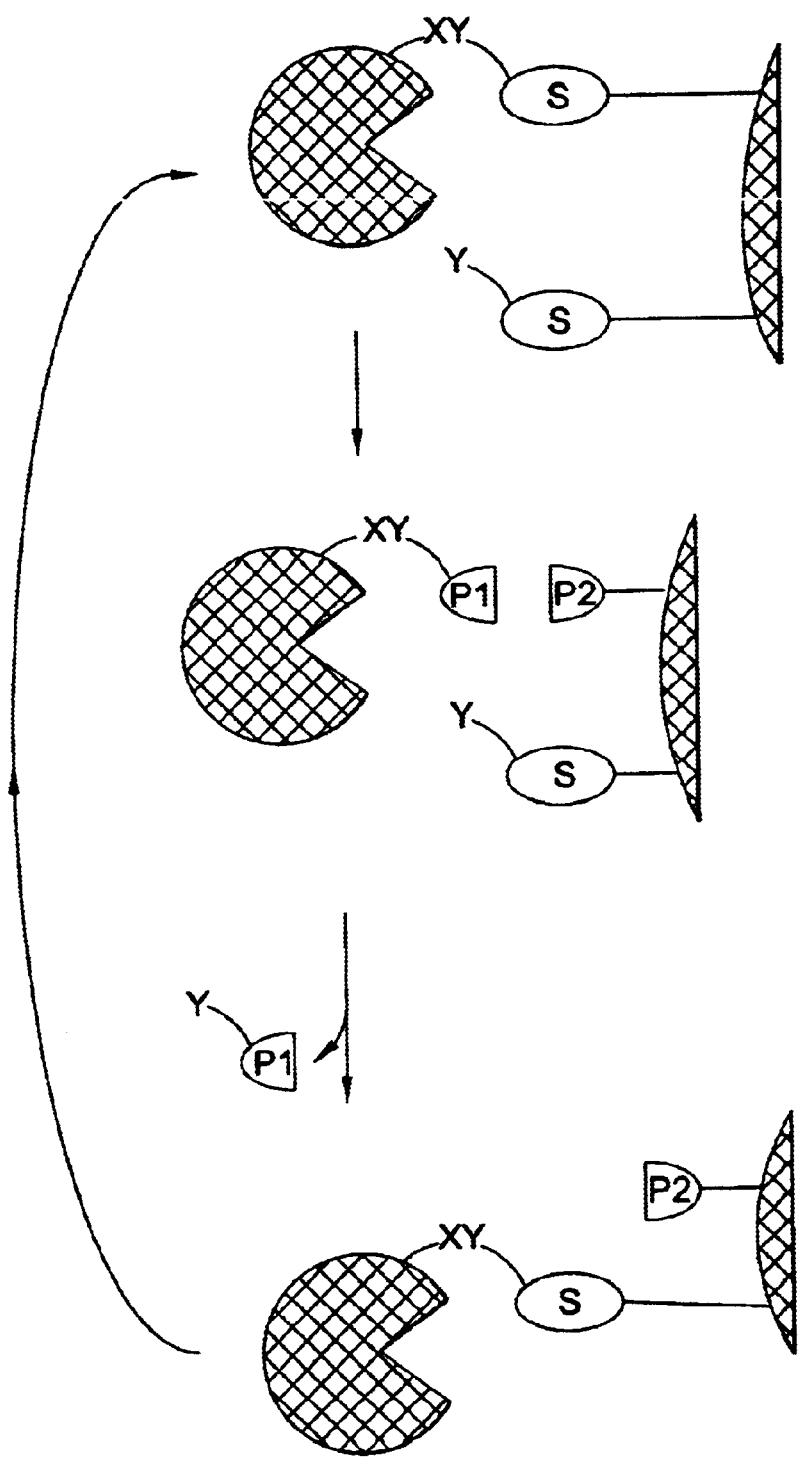

FIGS. 7–8: Graphic illustrations of suitable selection schemes according to a method for in vitro selection according to the second aspect of the invention.

Figure 9:
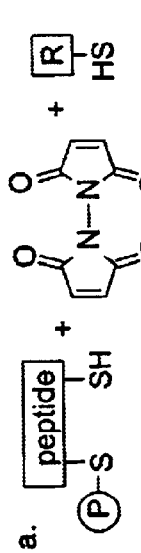
Figure 9:
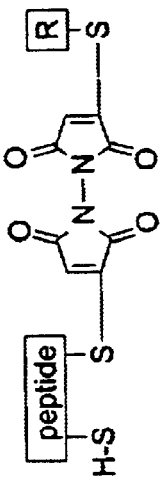
Figure 9:
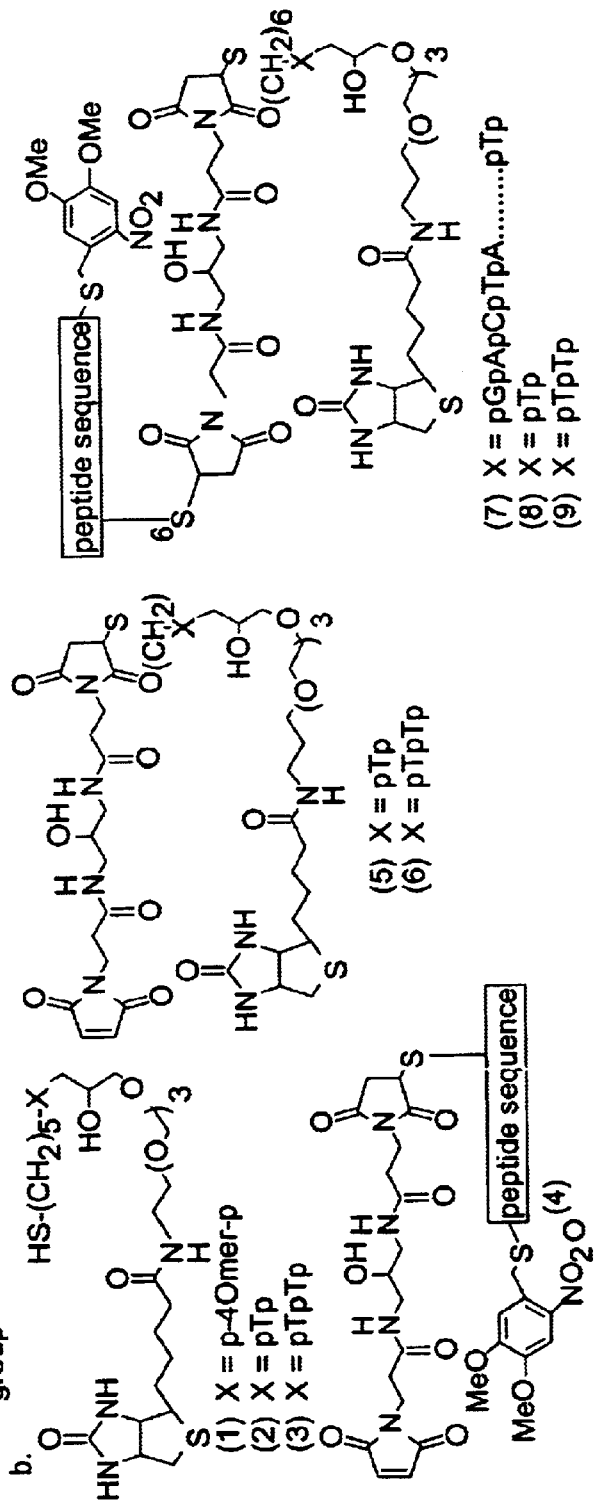
Figure 10:
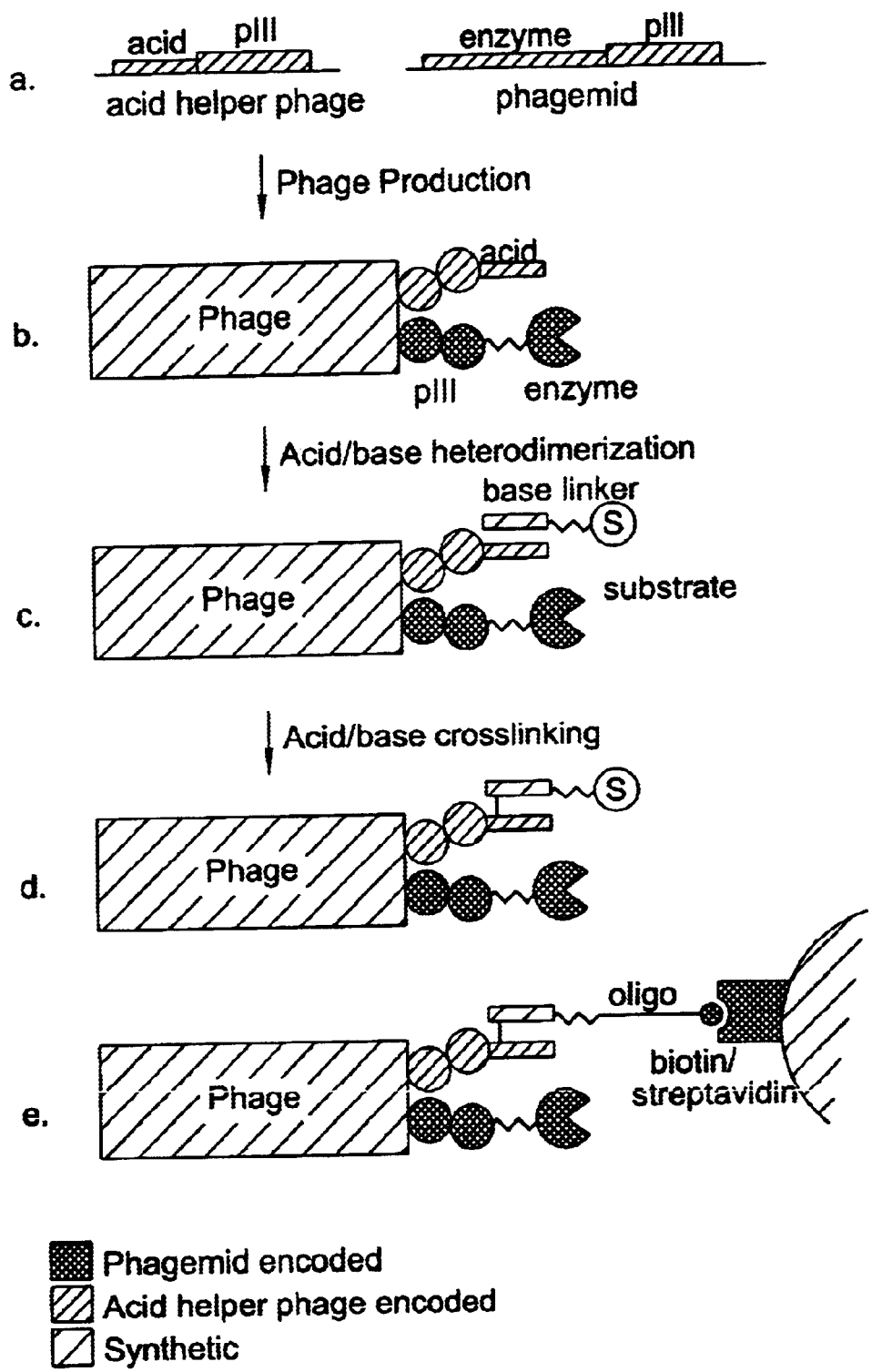
Figure 11:
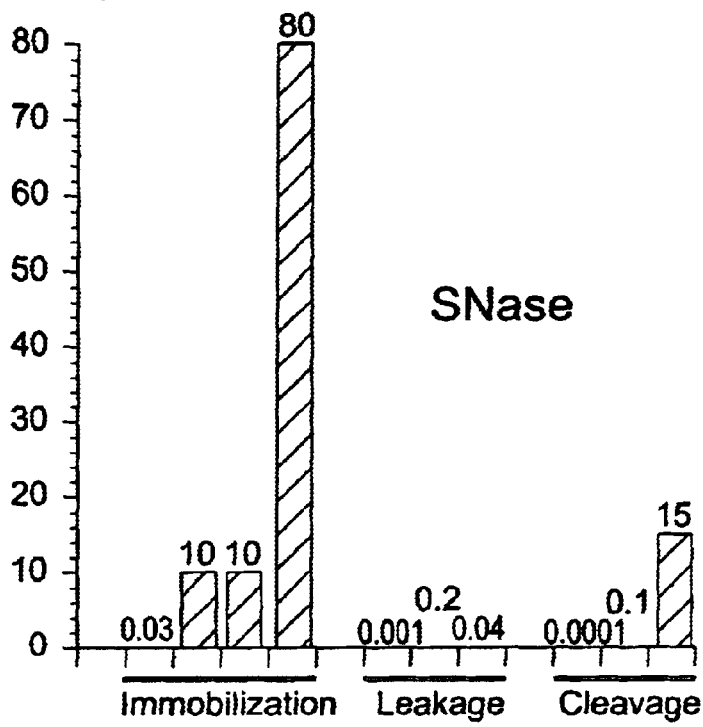
Figure 11:
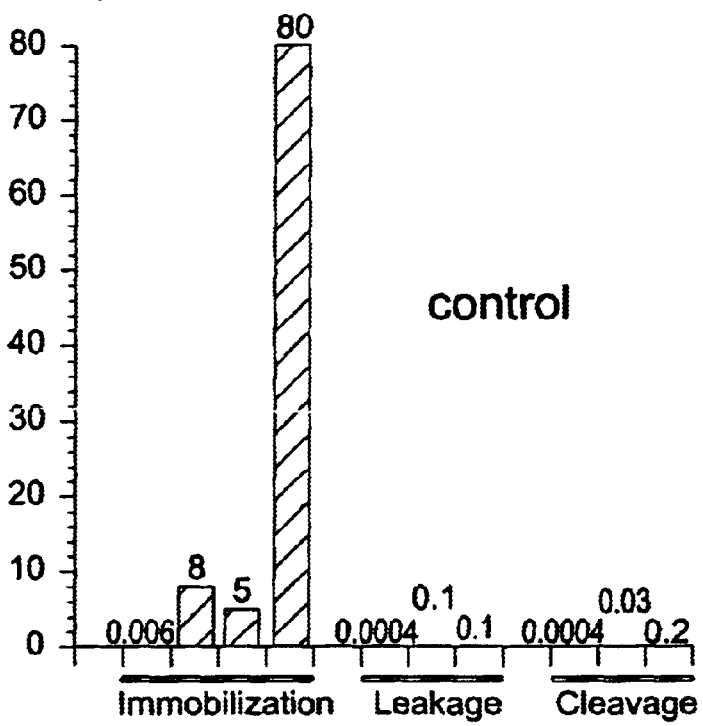

FIGS. 9–11: Figures supporting the description in working example 1 herein (vide infra).

FIG. 9. Structures and synthesis of base-linker-substrate conjugates.

FIG. 10. Covalent attachment of substrate to the pIII protein on phage. (a) DNA encoding the acid peptide sequence and a C-terminal cysteine was fused to the N-terminal end of gene gIII, to form the acid helper phage. A phagemid encodes the protein library in fusion with the pIII protein; (b) Phage production leads to phage particles displaying the phagemid encoded protein; the pIII proteins have acid peptide extensions; (c) Coiled-coil formation of the acid and base peptides noncovalently attaches the substrate to the phage pIII protein; (d) Removal of the reducing agent leads to crosslinking of acid and base peptides through their C-terminal cysteines; (e) In the present study phages displaying staphylococcal nuclease are attached to streptavidin beads through a 5'-biotinylated, single-stranded oligodeoxynucleotide. Phages displaying active enzyme are released by cleavage of the oligodeoxynucleotide in an intramolecular reaction.

FIG. 11: Immobilization and cleavage of phage from solid support. Either no base-linker, the base-linker-pTp or the base linker-oligodeoxynucleotide conjugate was crosslinked to (a) phage displaying SNase or (b) the control protein Fab 39-A11. Columns 1–4 show immobilization on streptavidin beads. Immobilization was either examined by phage titering of the beads directly (columns 1–3), or after DNase I treatment of the beads (column 4); columns 5–7 show leakage (release in absence of $Ca^{2+}$); columns 8–10 shows $Ca^{2+}$ induced release (cleavage). The per cent recovery is shown in parentheses above the columns.

Figure 12:
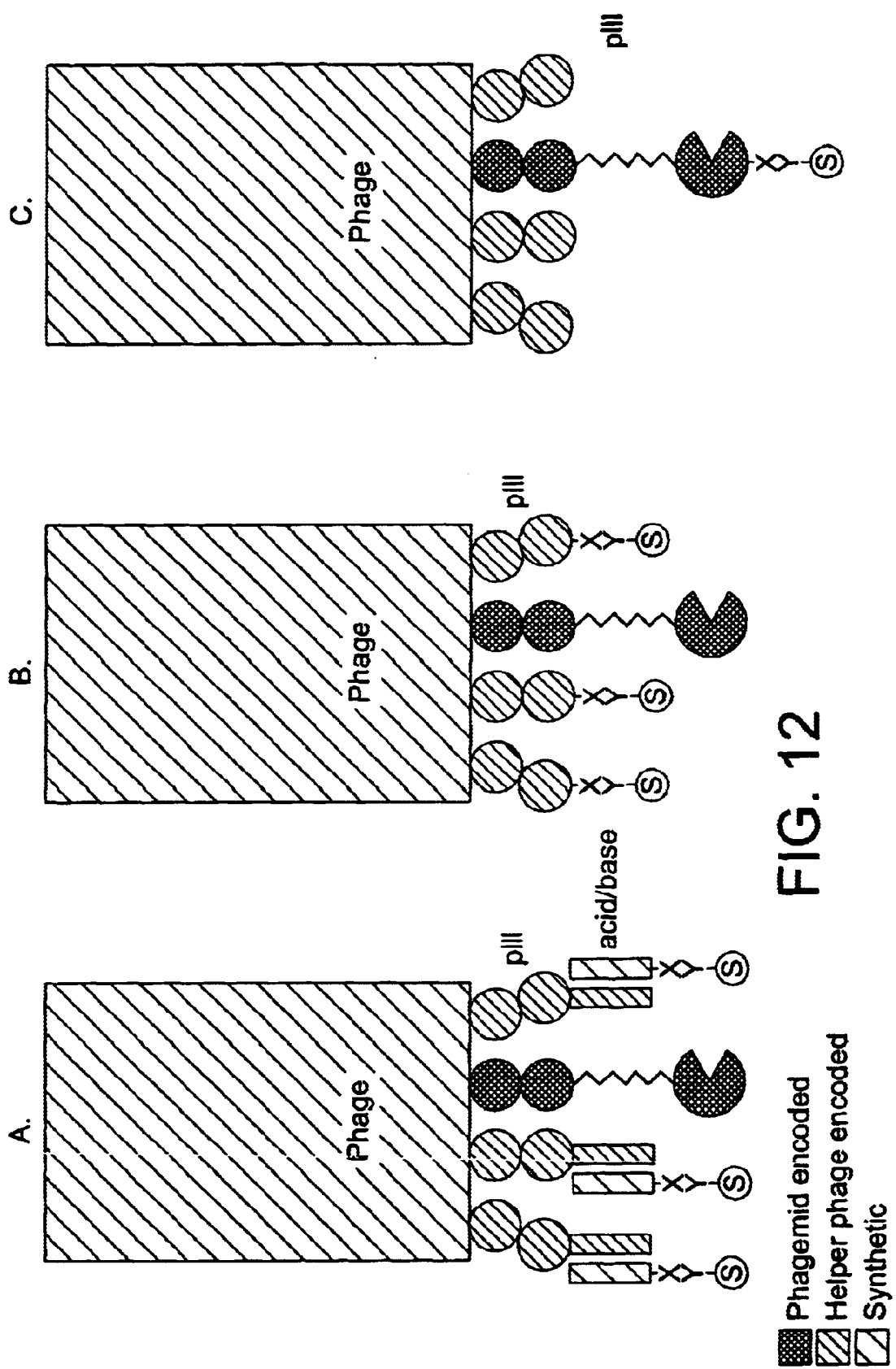

FIG. 12: Figure supporting the description in working example 5 herein (vide infra).

Figure 13:
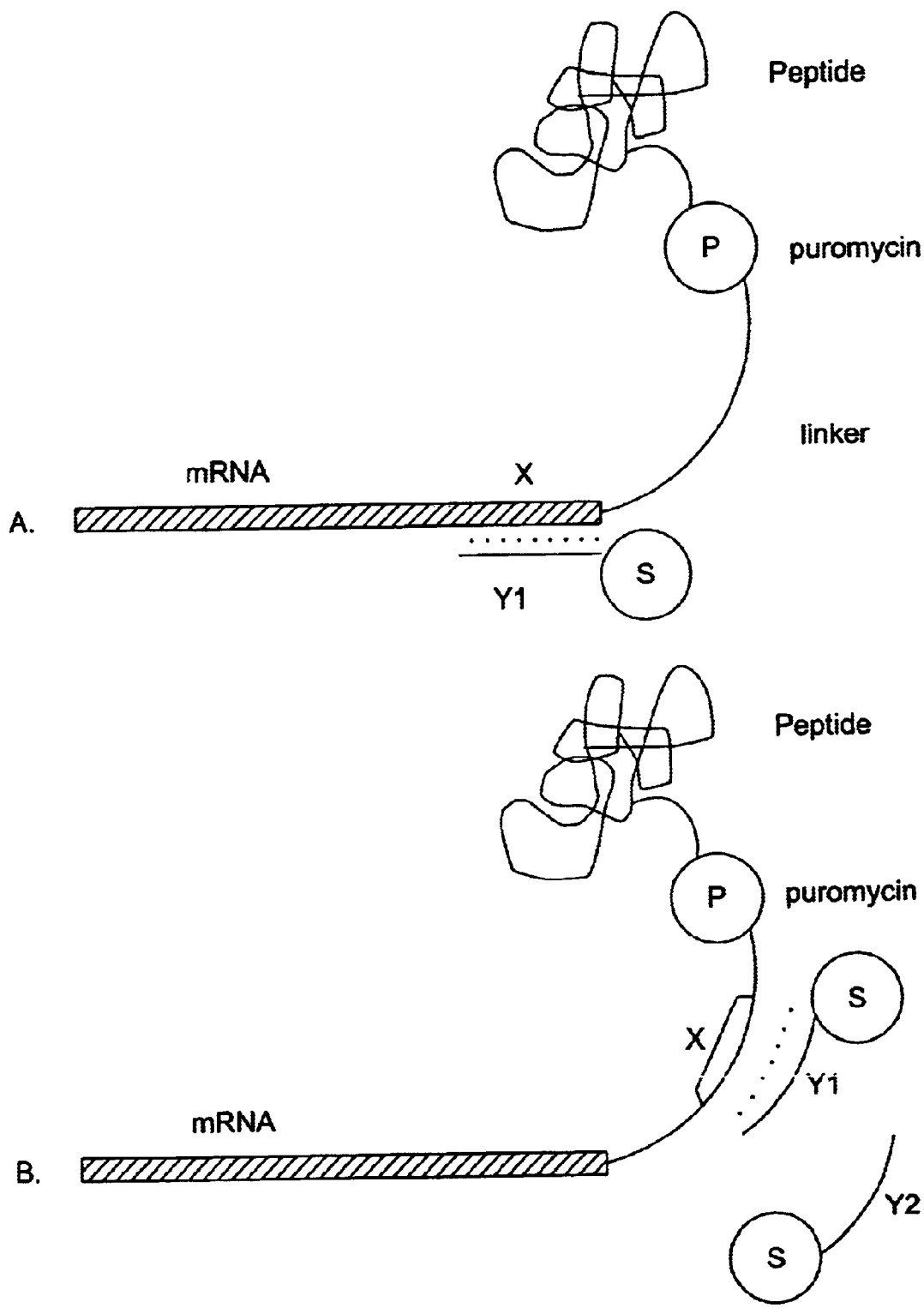

FIG. 13: Figure supporting the description in working example 6 herein (vide infra).

Figure 14:
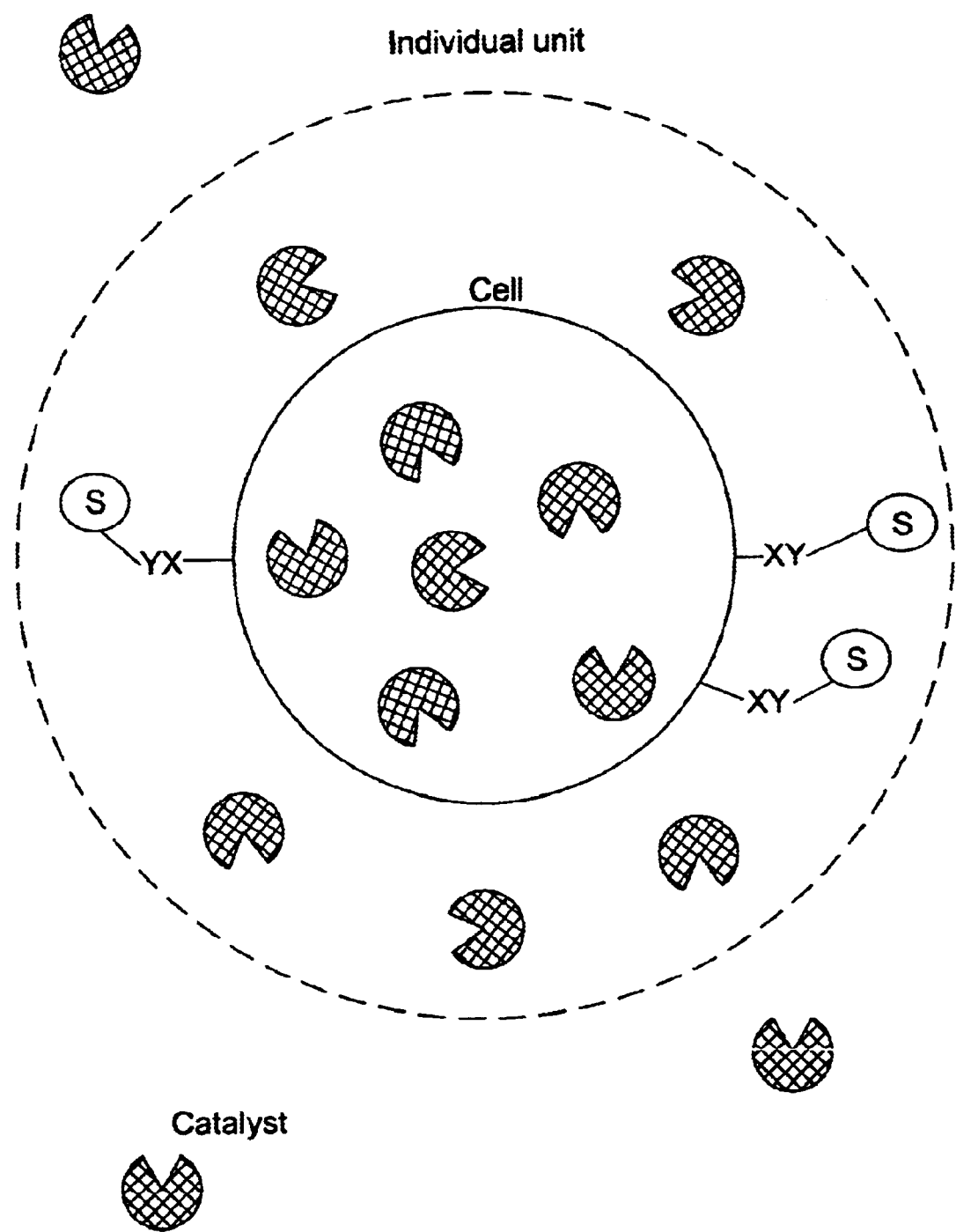

FIG. 14: Figure supporting the description in working example 7 herein (vide infra). Enrichment of cells producing the more active proteases.

Figure 15:
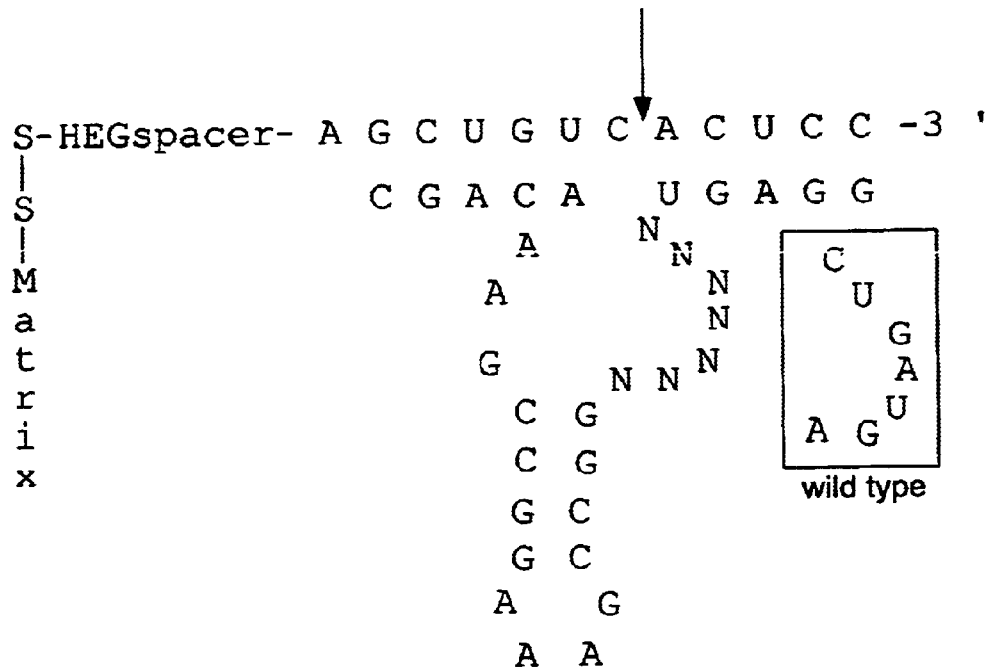
Figure 15:
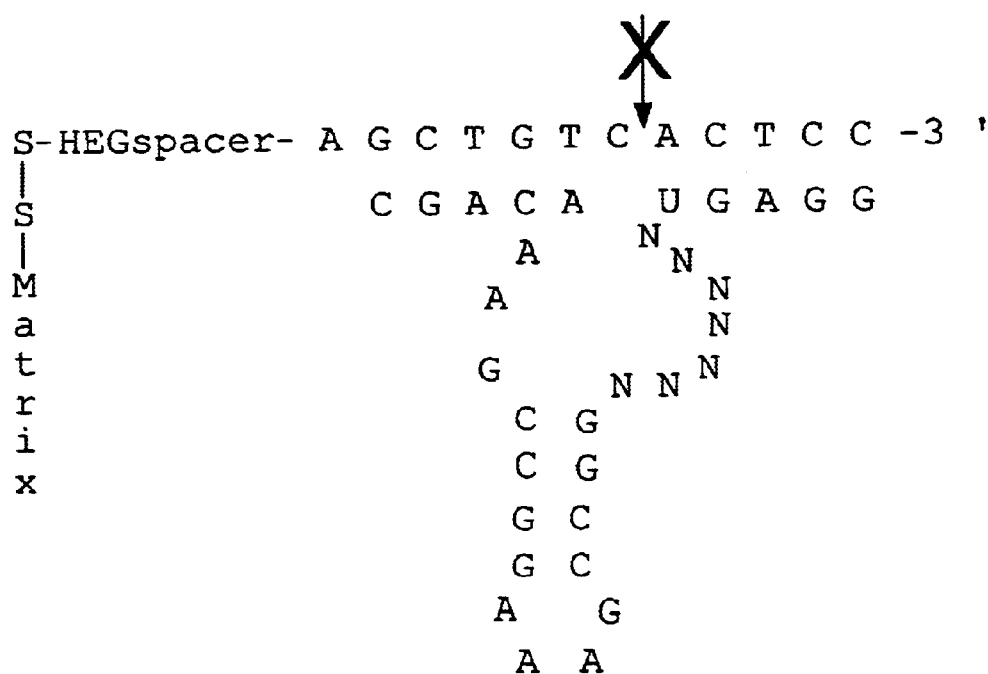

FIG. 15: Figure supporting the description in working example 8 herein (vide infra). Isolation of hammerhead ribozymes.

Figure 16:
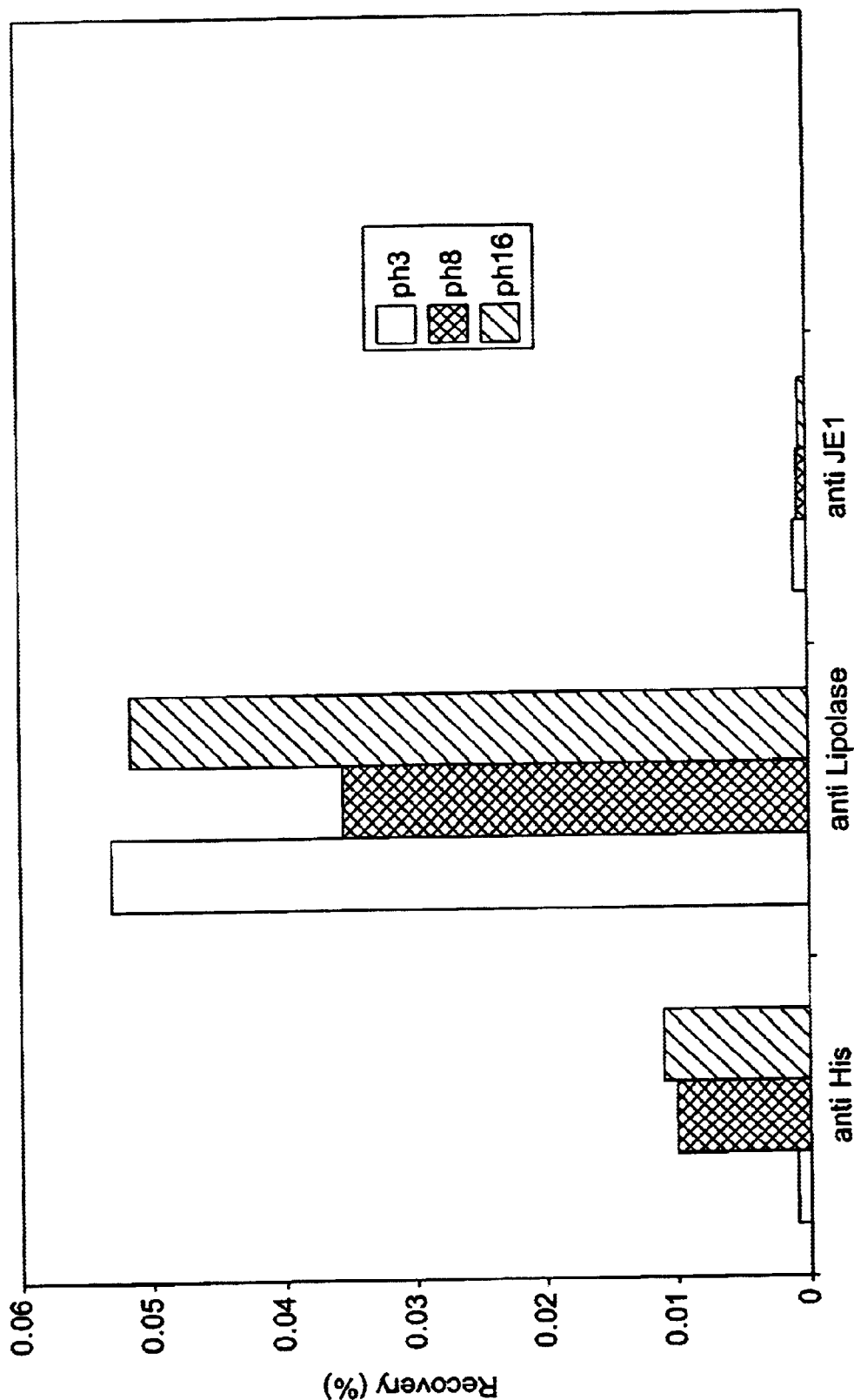

FIG. 16: Data supporting working example 10 herein (vide infra). Enrichment of wildtype lipase in a background of less active variants.

Figure 17:
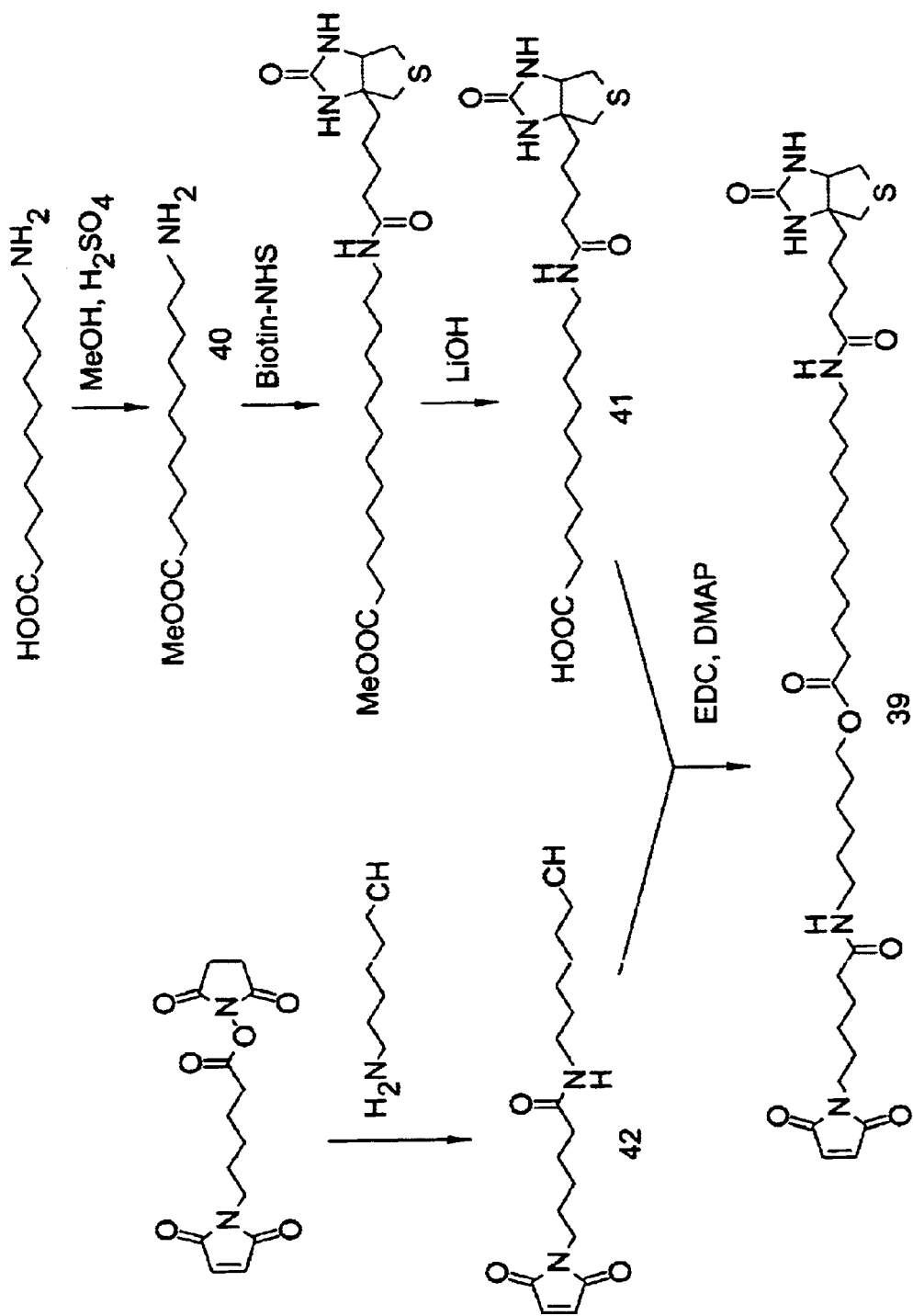

FIG. 17: Figure supporting the description in working example herein (vide infra). Synthesis of Y—substrate-biotin conjugates.

Figure 18:
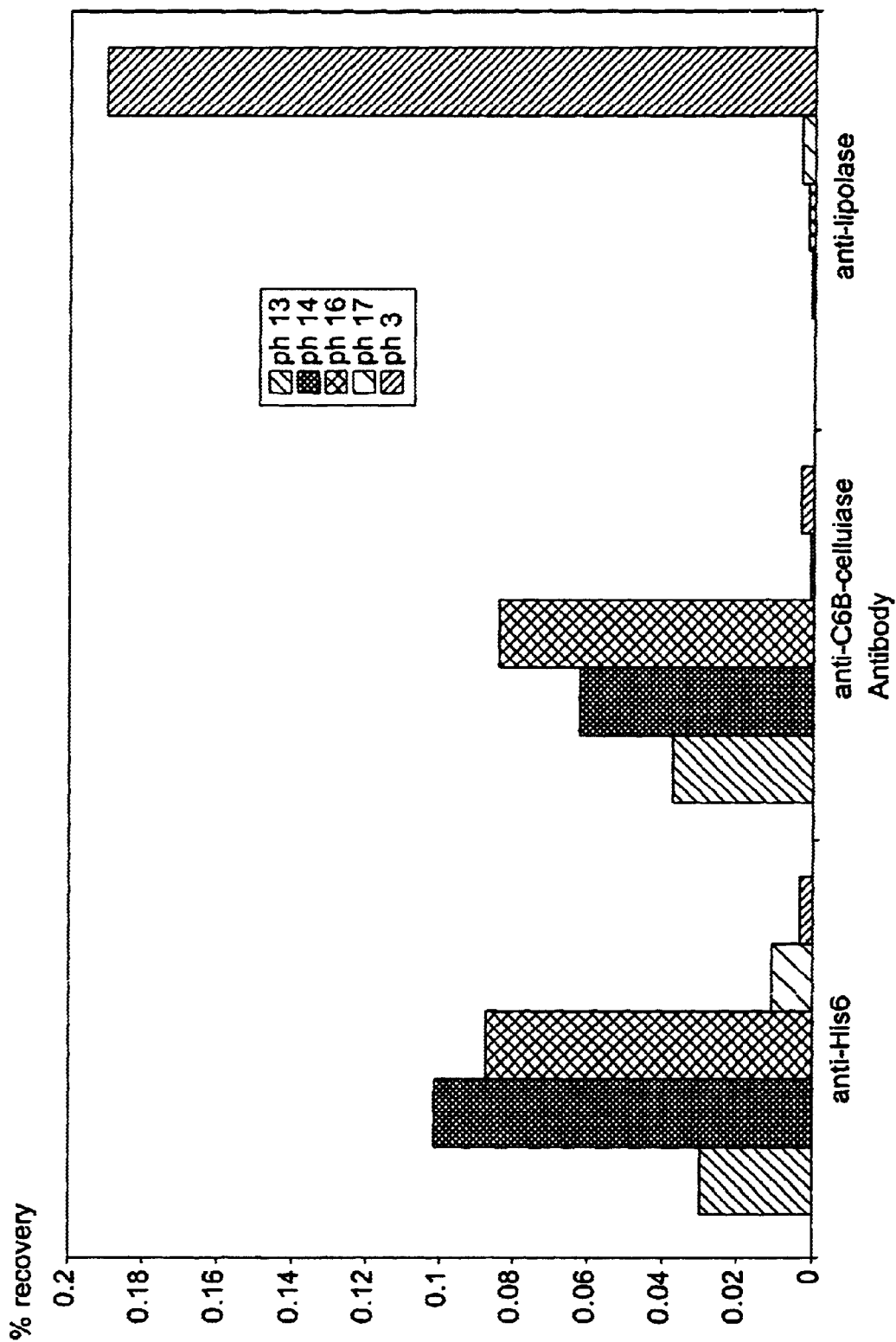

FIG. 18: Data supporting the description in working example 11 herein (vide infra). Enrichment of wildtype cellulase C6B, in a background of less active cellulase variants.

Figure 19:
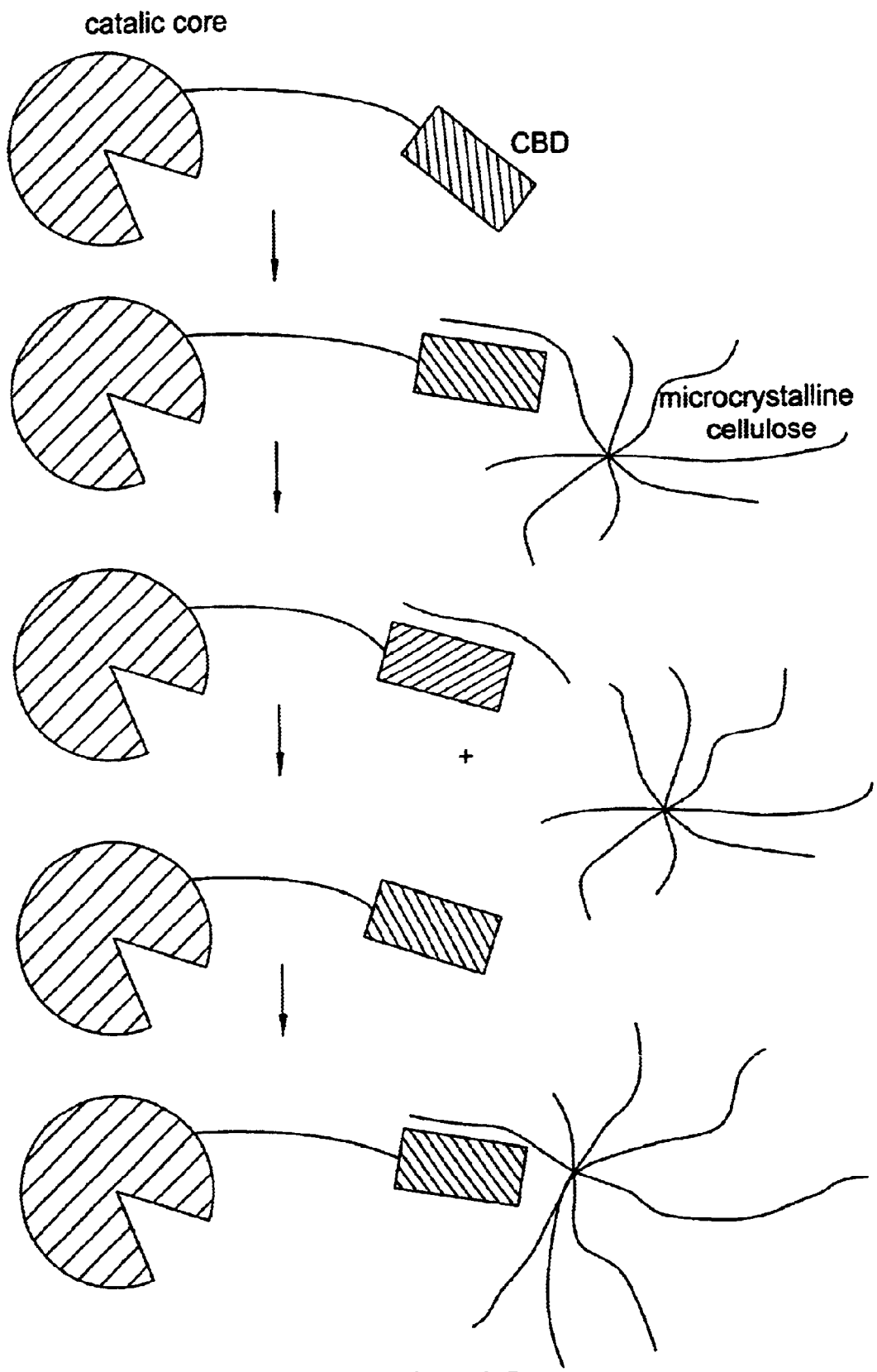

FIG. 19: Figure supporting the description in working example 11 herein (vide infra). The principle of substrate reloading in the context of the phage-displayed cellulase.

Figure 20:
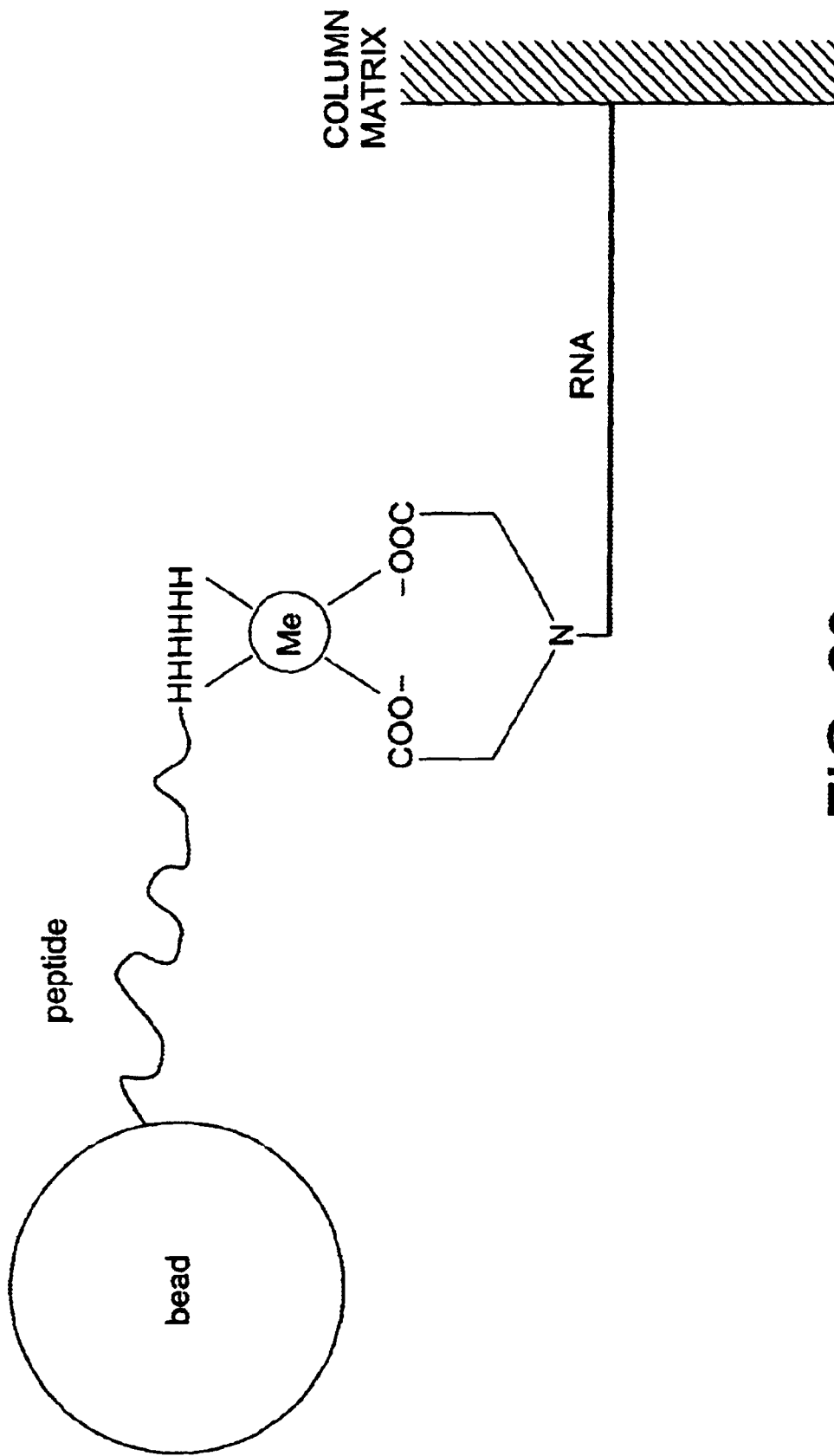

FIG. 20: Figure supporting the description in working example 12 herein (vide infra). Enrichment of wildtype RNase A in a background of less active RNase A variants.

Figure 21:
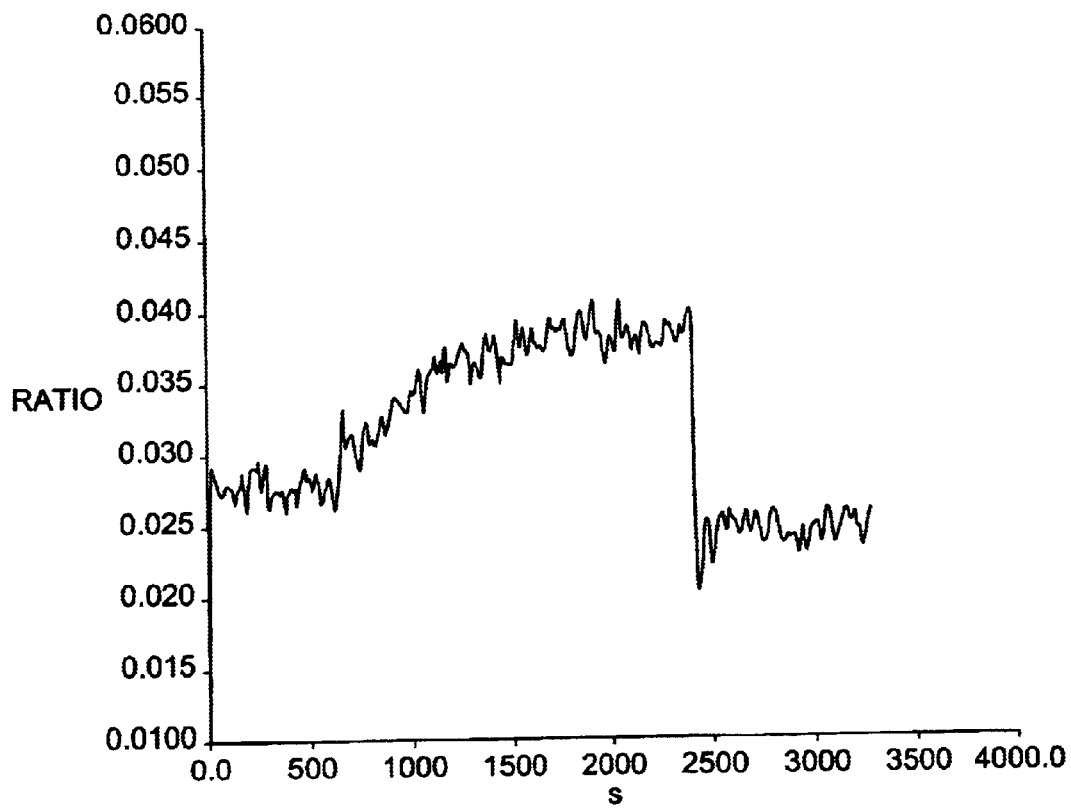
Figure 21:
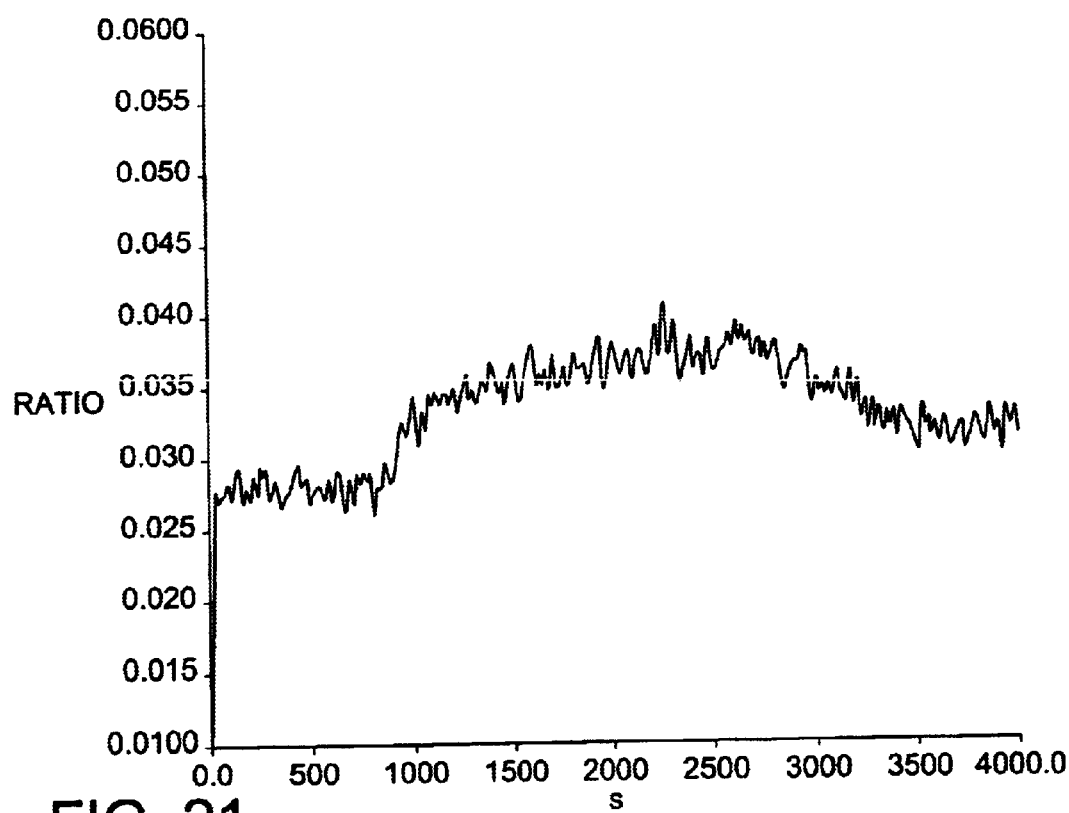

FIG. 21: Data supporting the description in working example 14 herein (vide infra). Measurement of exchange rates by fluorescence polarization spectroscopy.

Embodiment(s) of the present invention is described below, by way of examples only.

DETAILED DESCRIPTION OF THE INVENTION

A Sample Comprising a Number of Different Individual Units According to First Aspect of the Invention XY Exchange Pair:

As described above, within an individual unit, the catalyst is physically connected to substrate through an XY exchange pair. Thus, the individual unit has general structure a catalyst—an XY exchange pair—a substrate.

Further, as described above, the term "XY exchange pair", comprised within an individual unit as specified above, denotes that a catalyst is attached to a substrate through an XY exchange moiety, i.e., the individual unit has following general structure: a catalyst—an XY exchange pair—a substrate and said XY exchange pair fulfils the criteria according to point (c) in the first aspect of the invention.

Further, said exchange pair is preferably stable in the sense that the unit a catalyst—an XY exchange pair—a substrate will remain connected in the absence of another Y—substrate component, this means that under the conditions of the assay the X moiety should ideally at any given time be loaded with substrate. This may be the case if the Y—substrate concentration is significantly higher than the dissociation constant $K_d$ of the XY interaction under the conditions employed. In most cases, the maximum Y-substrate concentration will be of the order of 1 mM or less. Therefore, the dissociation constant $K_d$ should preferably be less than $10^{-4}$ M. The dissociation constant is given by $K_d=k_{off}/k_{on}$. The on-rate $k_{on}$ is generally limited by diffusion, with second-order rate constants for association of around $10^6$–$10^9$ M$^{-1}$ sec$^{-1}$. Therefore, in order to obtain good exchange rates (more than one exchange per second), the off-rate $k_{off}$ should preferably be at least 1 sec$^{-1}$, wherefore the $K_d$ in this case should not be less than $10^{-9}$ M. Therefore, in most cases where an exchange rate of more than 1 sec$^{-1}$ is desired, the dissociation constant should be in the range $10^{-4}$–$10^{-9}$ M.

This preferred embodiment provides a system wherein the XY exchange reaction may said to be an associative replacement reaction in the sense that the units C—XY—S or C—XY—P are stable if they are not placed in contact with a Y—S compound.

An XY exchange pair comprises at least one X-moiety and at least one Y-moiety. However it may also comprise more than one copy and/or type of both X- and Y-moieties.

Further the X and Y moiety may be identical molecules. Such an exchange pair may herein be termed an "XX exchange pair".

Preferably the X and Y moiety are different molecules.

For illustration as a non-limiting example the XY moiety is preferably stable in the absence of free Y, but allows fast and specific exchange of free Y with Y bound to X (but not exchange of free Y with X). This exchange reaction will replace product with substrate, if the individual units, as described above, are in contact with an Y—substrate compound.

The XY exchange pair may have the following characteristics:

i) X and Y can be covalently or non-covalently bonded.

The XY exchange pair can consist of any kind of molecules, including small organic (eg., EDTA) and inorganic (eg. metal, phosphate) molecules as well as macromolecules (eg., nucleic acids, peptides).

ii) The XY exchange reaction is preferably described as an active replacement reaction.

iii) The XY unit is preferably stable in the absence of another Y.

iv) The XY unit is preferably asymmetric, i.e. Y will only replace Y, not X.

v) The exchange of Y by Y is preferably very fast.

vi) The association of X and Y is preferably a very fast process.

vii) The exchange unit may be symmetric (ie., a XX exchange unit).

Suitable examples of XY exchange pairs are given below. Further, graphic illustrations of said examples are given in FIGS. 3 and 4.

i) Metal ligands. Preferably, the X moiety consists of a ligand and a metal ion, in a strong interaction described by a slow dissociation rate, basically making a very stable ligand-metal unit. The Y-moiety, on the other hand, is a ligand that coordinates to the same metal ion with high affinity, but with fast dissociation and association rates. Moreover, the exchange of one Y moiety with another Y-moiety is preferably a replacement reaction, for example because the Y-moiety is multi-dentate. Specific examples:

a) X: EDDA'—Ca$^{++}$ (EDDA, ethylendiaminediacetato, corresponds to EDTA in which the two acetic acids coupled to one of the nitrogens has been removed. EDDA thus makes four-fold coordination to Ca$^{++}$).

Y: R—N(CH$_2$COO$^-$)$_2$, a bidentate ligand, or

Y: R—N(CH$_2$COO$^-$)(CH$_2$)$_2$N(CH$_2$COO$^-$)$_2$, a tridentate ligand (Ca$^{++}$ can make up to nine-fold coordination to certain ligands).

b) X: His$_6$-Ni$^{++}$, presumably a four-fold coordination. The histidine tag is used for recombinant protein purification, and the six histidines may be inserted at the N- or C-terminus of proteins, or into exposed loops on the surface of proteins. Cu, Ni, Zn, Fe, Cd, Co, Mg and other metals, preferably with fast exchange kinetics, may be used with the peptide based chelate. Other peptides that coordinate metals, such as peptides containing 2 or more histidines (Schmidt et al., 1996, Current Biology, vol. 3, pp. 645–653; Kotrba et al., 1999, Applied and Environmental Microbiology, vol. 65, pp. 1092–1098), or the Cu-binding peptide Diglycyl-L-Histidine(Lau et al., 1974, *The Journal of Biological Chemistry*, vol. 249, pp. 5878–5884, may be used accordingly.

Y: R—N(CH$_2$COO$^-$)$_2$, a bidentate ligand.

c) X: His6-Ca$^{++}$ (Ca$^{++}$ has fast exchange characteristics with most ligands)

Y: Y: R—N(CH$_2$COO$^-$)$_2$, a bidentate ligand, or R—N(CH$_2$COO$^-$)(CH$_2$)$_2$N(CH$_2$COO$^-$)$_2$, a tridentate ligand.

ii) Macromolecular exchange moieties (nucleic acids). The Y moiety can consist of two polynucleotides, Y1 and Y2, that bind to overlapping sites on the X-moiety, which is also a polynucleotide. Preferably, the length and sequence of the oligos are adjusted so that the interactions of X with Y1 is stable in the absence of Y2, but Y2 can actively replace Y1—and vice versa.

The principle of overlapping regions of interaction should be generally applicable to exchange units of other chemical substances, such as proteins, polymers, organic or inorganic molecules. The principle is illustrated for polynucleotides:

a) X: DNA polynucleotide 5'-GGGGTTGTTCCCC-3' SEQ ID NO:5
   Y: equimolar mix of DNA polynucleotides Y1: 3'-CCCCAACAA-5' and Y2: 3'-AACAAGGGG-5'.

b) X: DNA polynucleotide 5'-GGAAGGGATGGTCAC-3 SEQ ID NO:6
   Y: Equimolar mix of polynucleotides Y1: 3'-CCTACTACCA-5' SEQ ID NO:7 and Y2: 3'-TCCCTAAGTG-3'. SEQ ID NO:8 iii) Covalent bonds. The formation and splitting of a covalent bond can be a rather fast process. In some cases this is an intrinsic characteristic of the bond in question. In other cases catalysts can speed up the rate at which the bond is formed and broken (eg., the enzymatic transesterification below). Specific examples follow below; "R" symbolises the site of attachment of the individual unit (catalyst), or substrate:

a) X: Boric acid, R—B(OH)$_2$
   Y: a sugar, or other vicinal diol
   The "bidentate" nature of the interaction (the concerted formation and splitting of two bonds) should result in the active replacement of one sugar molecule with another.

b) X: R$_1$—COOR$_2$ (an ester)
   Y: HO—R$_2$ (the corresponding alcohol)
   Thus, XY is in this case identical to X. To speed up the exchange rate, esterases may be added to the buffer. Likewise, transaminase-, transamylase- and other transferase-reactions can be exploited for the exchange of X and Y. For many of these reactions, it may be possible to employ the relevant transferase enzyme to speed up the exchange reaction.

c) X: R$_1$—SH
   Y: Comprises two types of molecules, Y1: R$_2$—SH (a free thiol) and Y2: R$_2$—SS—R$_2$ (a disulfide).
   In its substrate-attached form, the catalyst is coupled to the substrate through a disulfide bond. Protein-disulfide isomerase may be added to the buffer to speed up the rate of exchange.

d) X: vicinal dithiol, or paired thiols (for example, alpha-helical peptide with cysteine at position i and i+1)
   Y: trivalent arsenic containing compound
   This type of vicinal dithiol-trivalent arsenic interaction has been used for the chromatographic purification of thiol containing proteins (Gitler et al., 1997, Analytical Biochemistry, vol. 252, pp. 48–55), or for the strong affinity interaction of biarsenical ligands with alpha-helical peptides containing cysteine at position i, i+1, i+4, and i+5 (Griffin et al., 1998, Science, vol. 281, pp. 269–271). The exchange reaction may be accelerated by including reducing agents such as DTT or 2-mercaptoethanol.

iv) Catalyst—substrate pairs. The interaction between a catalyst (e.g. an enzyme) and a substrate is often described by two constants, the $k_{cat}$ (turn-over number) and the Km. The $k_{cat}$ can be said to broadly define the lifetime of the productive catalyst/substrate-complex. Therefore, one can obtain XY units with varying exchange rates (stabilities) by using for example different enzyme variants with different $k_{cat}$'s for a given substrate (where the enzyme represents X, and substrate represents Y) FIGS. 3 and 4. catalysts that interact with more than one substrate at a time may be particularly useful as XY exchange units.

v) XY interaction is modified by the reaction substrate to product. In certain cases the structure of the XY-Substrate moiety can be designed so that the reloading process is accelerated by the activity of the catalyst of the individual unit. For example, if X or Y is both exchange unit and substrate for a cleavage reaction, the cleavage is likely to result in the dissociation of XY, wherefore the reloading process is likely to happen faster. In example 8 below, X and Y are both nucleic acid structures. Y is both exchange unit and the substrate of the desired reaction (cleavage of a ribo-dinucleotide). Upon cleavage of Y the XY unit dissociates, which should speed up the association of X with another Y-substrate unit.

This principle can be applied more generally. For example, the central portion of Y in example 8 (the cleavage target) can be exchanged with the substrate of another desired reaction (see FIG. 3A). Again, the conditions can be chosen so that the association of X and Y$_{left}$-Substrate-Y$_{right}$ is strong, but the interaction of X and Y$_{left}$-Product1, or X and Product2-Y$_{right}$, is weak. Therefore, immediately following cleavage of the substrate, X and Y fall apart. Which speeds up the substrate reloading process.

The substrate does not have to be part of X or Y for this event to take place. For example, if a conformational change, induced by the reaction substrate to product, is transmitted from the product to Y, and this conformational change results in the dissociation of XY, this will also speed up the reloading process. An example is given in FIG. 3B.

vi) Enzymes and other substances in the column buffer may speed up the exchange reaction in other ways. For example, the reaction substrate to product may initiate another reaction (catalyzed by a substance in the column buffer) that dissociates X and Y. For example, if the catalyst of the individual unit cleaves a nucleic acid, this may expose free 3'- or 5'-ends, accessible to exonucleases. If the nucleic acid represents both the target substrate and the Y unit, the Y unit may be degraded by the nuclease, and therefore the XY complex dissociates. Alternatively, the XY complex (but not uncomplexed X or Y) may be the target for a substance in the column buffer; if the substance modifies X or Y in the XY complex so that it dissociates faster, the presence of the substance will speed up the exchange rate. For example, if X and Y are complementary DNA and RNA oligos, RNaseH can be included in the buffer. RNaseH cleaves RNA in duplex complexes; therefore, the RNA (Y) will not be cleaved, until it associates with the DNA (X) to form the duplex. RNaseH will cleave the RNA but leave the DNA intact. Therefore, RNaseH accelerates the dissociation of XY but the individual unit-linker-X unit is left intact, ready to interact with another Y.

Detailed examples of suitable XY exchange pairs are further described in working examples herein (vide infra).

A Sample Comprising a Number of Different Individual Units:

As specified above said sample may comprise at least two different individual units and up to numerous different individual units.

The actual number of different individual units generally corresponds to the actual size of the library of catalyst molecules.

Besides said specified different individual units said sample may in principle also comprise any other suitable material.

Further said different individual units comprised within said sample may be dissolved in any suitable buffer, such as water.

Even further said sample may also comprise the Y-substrate compound which is in contact with the different individual units according to step (i) of the method of the second aspect of the invention.

Different Individual Units:

As described above, an individual unit comprises the general structure:

a catalyst—an XY exchange pair—a substrate; or if the substrate has been converted into the product, the general structure:

a catalyst—an XY exchange pair—a product.

Further, the term "different individual units" denotes different individual units each independently comprising different catalyst molecules, i.e. an example of two different individual units may be (1) catalyst molecule[1]—XY exchange pair—substrate; and (2) catalyst molecule[2]—XY exchange pair—substrate; wherein catalyst molecule[1] and catalyst molecule[2] denotes two different catalyst molecules.

Further, "an individual unit" as described herein denotes an individual unit wherein it is possible to physically separate said individual unit from the other different individual units, within said sample, in order to be able to isolate the separate individual unit.

A Biologically Amplifiable Individual Unit:

An embodiment of the invention relates to a sample comprising a number of individual units according to the invention, wherein the individual unit of point (i) according to the first aspect of the invention is a biologically amplifiable individual unit.

Another embodiment of the invention relates to a sample comprising a number of individual units according to the invention, wherein the individual unit of point (i) according to the first aspect of the invention is a biologically amplifiable individual unit and both said substrate and said catalyst molecule are attached on the surface of said biologically amplifiable individual unit.

The term "a biologically amplifiable individual unit" denotes that within said individual unit either;

(i) the catalyst molecule of interest is a biologically amplifiable molecule; or (ii) the catalyst molecule of interest is biologically encoded by the information comprised within the entity allowing the unambiguous identification of the catalyst molecule;

providing the possibility of amplifying said catalyst molecule of interest in order to obtain multiple copies of said catalyst molecule.

The term "biologically encoded" in point (ii) above denotes that the information is comprised within a DNA or RNA molecule in the form of the genetic code.

An example of an biologically amplifiable individual unit in relation to point (i) above is an individual unit wherein the catalyst molecule of interest is a DNA or a RNA molecule, since it is well known in the art that DNA or RNA molecules may easily be amplified.

An example of an biologically amplifiable individual unit in relation to point (ii) above is an individual unit wherein the catalyst molecule of interest is a peptide or a polypeptide and wherein said entity comprising information allowing the unambiguous identification of the catalyst molecule is a DNA molecule encoding said peptide or polypeptide.

In relation to the second example above, a physical connection must exist between the peptide and the DNA that encodes it, in order to isolate the DNA with the peptide it encodes. The connection can be either direct, in which case the peptide is attached directly to the nucleic acid that encodes it, or indirect, where the peptide can be either attached to the surface of for example a cell, or alternatively secreted from a cell and therefore much more abundant in the immediate vicinity of the secreting cell than anywhere else. Such a cell is herein termed a "carrier system" as will be further discussed below.

Flexible Linker:

An embodiment of the invention relates to a sample comprising a number of different individual units according to the first aspect of the invention, wherein said individual unit of point (i) comprises following structure: catalyst molecule-flexible (XY exchange pair) linker—substrate.

Preferably the flexible linker is comprising the XY exchange pair.

The term "flexible linker" refers herein to the molecules as a whole connecting the catalyst with substrate. For example, if the substrate is attached to a bead through a flexible molecule, and the catalyst is also attached to the bead through a flexible molecule, "flexible linker" will refer to "flexible molecule-bead-flexible molecule", and the characteristics of the flexible linker will reflect the individual characteristics of the two flexible molecules and the portion of the bead that connects the two. Flexible linkers may for instance consist of flexible polypeptides, polyethylen glycol (PEG), and other polymers of reasonable flexibility.

Further, a flexible linker may also connect the catalyst molecule and a carrier system (see below).

Carrier Systems

An embodiment of the invention relates to a sample comprising a number of different individual units according to the invention, wherein said individual unit of point (i) in the first aspect of the invention comprises the following structure: catalyst molecule—carrier system—XY exchange pair—substrate, or more preferably the structure: catalyst molecule—carrier system—flexible (XY exchange pair) linker—substrate.

The term "carrier system" denotes a system/entity which physically connects the catalyst molecule and the substrate, or alternatively, carries the information allowing the unambiguous identification of the catalyst molecule, and wherein said carrier system does not directly participate in the catalytic reaction of the substrate to the product, catalysed by the catalyst molecule.

Such a carrier system is herein further divided into a biologically amplifiable carrier system and a biologically non-amplifiable carrier system.

Examples of biologically amplifiable carrier systems include (carrier system—catalyst molecule): phage—polypeptide (Boublik et al., 1995, Biotechnol (NY), vol. 13, pp. 1079–1084), filamentous phage—peptide (Kay, Winter and McCafferty, 1996, "Phage Display of Peptides and Proteins, A Laboratory Manual", Academic Press), retrovirus—polypeptide (Buchholz et al., 1998, Nature Biotechnology, vol. 16, pp. 951–954), plasmid—peptide (Schatz et al., 1996, Meth. Enzym., vol. 267, pp. 171–191), polysome—peptide (Mattheakis et al., 1994, Proc. Natl. Acad. Sci. USA, vol. 91, pp. 9022–9026; He and Taussig, 1997, Nucleic Acids Research, vol. 25, pp. 5132–5134), bacteria—peptide (Brown, 1997, Nature Biotechnology, vol. 15, pp. 269–272) and mRNA—peptide (Roberts and Szostak, 1997, Proc. Natl. Acad. Sci. USA, vol. 94, pp. 12297–12302), cDNA—peptide (analogous to the mRNA-protein fusion display, except that the protein has been attached to a cDNA of the MRNA that encodes it, rather than to the mRNA itself), peptide-secreting cell—peptide (Kinsella and Cantwell, 1991, Yeast, vol. 7, pp.445–454), peptide-secreting artificial microsphere—peptide (artificial microspheres containing proteins expressed from the genes contained within the microsphere, see Tawfik and Griffiths, 1998, Nature Biotechnology, vol. 16, pp. 652–656).

Examples of biologically non-amplifiable carrier systems include (carrier system—catalyst molecule): bead—organic molecule or bead—peptide (Brenner and Lerner, 1992, Proc. Natl. Acad. Sci. USA, vol. 89, pp. 5381–5383), pin—inorganic molecule and bead—DNA sequence (Geysen et al., 1996, Chemistry and Biology, vol. 3, pp. 679–688).

It should be noted that an individual unit comprising the beads—DNA sequence structure is herein a biologically amplifiable unit (se above), however the carrier system, as such (bead) is a biologically non-amplifiable carrier system.

Catalyst and Library of Catalyst Molecules:

As stated above the term "catalyst" denotes any catalyst molecule with a desired catalytic activity, such as organic and inorganic molecules, proteins, enzymes, peptides, nucleic acids, biopolymers and non-biological polymers, small organic or inorganic molecules. Further the terms "catalyst" and "catalyst molecule" may be used interchangeably.

Accordingly, a further embodiment of the invention relates to, (i) a sample comprising a number of different individual units according to the invention, wherein said library of catalyst molecules is a library of natural or unnatural peptides or polypeptides, preferably a library of enzymes;

(ii) a sample comprising a number of different individual units according to the embodiment (i) immediately above, wherein said library is a library comprising polypeptides having a number of different enzymatic activities; or (iii) a sample comprising a number of different individual units according to the embodiment (i) above, wherein said library is a library comprising polypeptides variants derived from one or more precursor polypeptide(s), wherein said precursor polypeptide(s) exhibit(s) closely related enzymatic activities.

The term "library comprising polypeptides having a number of different enzymatic activities" preferably denotes a library wherein said different enzymatic activities are substantially different activities, e.g. protease, amylase, xylanase, cellulase activities. An advantage of such an library may be that by changing the substrate according to the specific activity of interest, said library may be used to identify a number of polypeptides of interest. If for instance a protease of interest first is isolated by a method for in vitro selection as described herein by use of e.g. a peptide as substrate, then an amylase may be isolated thereafter by chancing the substrate to a e.g. a starch molecule.

The term "natural or unnatural peptides or polypeptides" denotes that the peptides or polypeptides may be build from any of the twenty natural amino acids building blocks, or any unnatural amino acids with other side chains, or any non-amino acid building block that is able to link two peptides together. Said libraries may be made according to any of the numerous standard processes known for making such libraries.

Accordingly, a further embodiment of the invention relates to a sample comprising a number of different individual units according to the embodiments of the invention mentioned immediately above, wherein said library is a library comprising shuffled/recombined/doped polypeptides.

Another embodiment of the invention relates to, (i) a sample comprising a number of different individual units according to the invention, wherein said library of catalyst molecules is a library of natural or unnatural nucleic acids;

(ii) a sample comprising a number of different individual units according to the embodiment (i) immediately above, wherein said library is a library comprising nucleic acids having a number of different catalytic activities; or (iii) a sample comprising a number of different individual units according to the embodiment (i) above, wherein said library is a library comprising nucleic acid variants derived from one or more precursor nucleic acid(s), wherein said precursor nucleic acid(s) exhibit(s) closely related catalytic activities.

The term "library comprising nucleic acids having a number of different catalytic activities" preferably denotes a library wherein said different catalytic activities are substantially different activities, e.g. nuclease, ligase, isomerase, phosphorylase. An advantage of such a library may be that by changing the substrate according to the specific activity of interest, said library may be used to identify a number of nucleic acids of interest. If for instance a DNA ligase of interest first is isolated by a method for in vitro selection as described herein by use of e.g. two DNA oligonucleotides as substrates, then a ribonuclease may be isolated thereafter by changing the substrate to a e.g. a RNA oligonucleotide.

Said libraries may be made according to any of the numerous standard known processes of making such libraries.

Accordingly, a further embodiment of the invention relates to a sample comprising a number of different individual units according to the embodiments of invention mentioned immediately above, wherein said library of nucleic acids is a library comprising shuffled/recombined/doped nucleic acids.

The term "natural or unnatural nucleic acids" denotes that the nucleic acids may contain any of the five natural bases (A, T, G, C, U), or any unnatural base or backbone structure.

Further embodiments of the invention relate to (i) a sample comprising a number of different individual units according to the invention, wherein said library of catalyst molecules is a library comprising natural polymer molecules, or unnatural polymer molecules, or small organic molecules, or small inorganic molecules or a mixture of said molecules; or (ii) a sample comprising a number of different individual units according to the embodiment mentioned immediately above, wherein said library is made by combinatorial chemistry.

Preferably, the sample may contain a virtual combinatorial library (Proc. Natl. Acad. Sci. USA, 1997, vol. 94, pp. 2106–2110), in the sense that each potential catalyst is made up of more than one subunit, held together by reversible covalent or non-covalent interactions, and the subunits associate and dissociate several times during the multiple turnover assay.

In the context of virtual combinatorial libraries, the term "unambiguous identification" which is used throughout this text, should be understood in terms of the unambiguous identification of the recovered entities, but not necessarily the composition of the individual catalysts. Such catalysts, isolated from virtual combinatorial libraries, could be catalysts made up of several polypeptide chains, held together by weak interactions (as for example protein subunit association, characterized by low subunit-subunit affinities), or held together by reversible covalent disulfide-bonds, whose exchange rates have been accelerated by the addition of redox-buffers (eg. oxidized and reduced glutathione) and therefore continuously are associating and dissociating.

The term "natural polymer molecules, or unnatural polymer molecules" denotes that the polymers may be of a kind found in Nature, or of a kind that is artificially produced by Man.

Alternatively, the library members could be assemblies of small organic molecules held together by disulfide bonds; again, the dynamics of the virtual combinatorial library may be speeded up by including a redox buffer.

In an even further embodiment the invention relates to a sample comprising a number of individual units according to the invention, wherein the catalyst molecules and the substrate capable of being catalysed into a product (point (i) in the first aspect) are of a different chemical substance.

The term "catalyst molecules and the substrate capable of being catalysed into a product (point (i) in the first aspect) are of a different chemical substance" denotes that said catalyst molecule and the substrate molecule are of a substantially different chemical substance.

Accordingly, in this preferred embodiment the situation wherein the catalyst molecules and the substrate molecule are both DNA or RNA molecules are herein said to be a situation wherein the catalyst molecules and substrate molecules are NOT of a different chemical substance.

A Method for Multiple Catalytic Activity Turn-over in Vitro Selection, According to the Second Aspect of the Invention The term "selection" preferably denotes that the selection according to step (ii) in the second aspect of the invention, is performed on more than one, preferably more than 100, or preferably more than 10.000, more preferably more than 1.000.000, even more preferably more than $10^8$, and most preferably more than $10^{10}$ individual units comprised within a sample, preferably without interference of the skilled person.

The term "column" denotes herein all kinds of solid support. Examples are: columns, surfaces including Biacor™ apparatus. In some cases there is no need for a solid support, as is the case if the separation is based on migration in an electric field.

Y-Substrate Compound and Isolation of a Catalyst of Interest According to the Method of the Second Aspect of the Invention:

As described above, the term "said individual units are in contact with a Y-substrate compound" according to point (i) in second aspect of the invention denotes that the individual units and the Y-substrate compound are appropriately close that an exchange reaction is possible. Said contact may for instance be in a buffer solution wherein the individual units and the Y—substrate compound may diffuse together and thereby get in contact with each other.

During selection rounds performed according to the method for multiple catalytic activity turn-over in vitro selection, according to the invention, it may be advantageous to perform the first selection rounds less stringently than later selection rounds. This can be done easily, e.g. by using a low concentration of Y-substrate, and/or a low concentration of a product binding receptor, in certain cases it may be desirable in the first round(s) to use no Y-substrate. Additionally, less efficient Y-substrate compounds can be used. In later selection rounds the concentrations are then increased. For certain experimental set-ups, this may not be feasible. For example, if a library consisting of very active enzymes is used, and the method of isolating the catalyst is based on immobilization on a product binding column, the high initial concentration of Y-substrate may result in high concentration of Y-product. Depending on the capacity of the product binding column, this may saturate the product binding receptors with product and hence, lead to lower selection stringency. However this problem can be solved, e.g. by (in the case of cleavage reactions) attaching the catalyst to the column via a linker that contains the substrate (see FIG. 8). To further increase the stringency of the selections, one may add excess substrate S (not connected to Y) to a column buffer (this will serve as "competitor substrate"). Other ways to modify selection stringency include variation of the length of the linker that connects enzyme and substrate, addition of factors to the column buffer which have affinity for the substrate or enzyme, or addition of factors that affects subtrate-enzyme interaction (eg. receptors/antibodies binding the enzyme's active site, enzyme inhibitors, receptors/antibodies with affinity for the substrate).

In order to limit the time available to the catalysts for substrate turn-over, pulses of for example voltage or light may be applied during the selection. Appropriately separated pulses could create for example transient pH- or ionic gradients that would initiate the reaction substrate to product, performed by the catalyst. The pulses should be separated enough in time that it allows plenty of time for a catalyst in solution to become immobilized on a receptor before the puls initiates the next reaction. In this way, the dead time of the selection performed in the column format (i.e. the time the catalyst spends diffusing from one receptor to the next) can be drastically reduced, and very high stringencies obtained.

Generally speaking, it is within the skilled persons general knowledge to optimize the specific experimental set-up.
Performing an Enrichment Step Prior to Step (i) of the Second Aspect of the Invention Certain proteins are difficult to display on filamentous phage. In particular large proteins or proteins which have a toxic or growth inhibiting effect on *E. coli* often have low display efficiency, i.e. the majority of phage particles produced carry no displayed proteins on the surface. Display efficiencies as low as one out of a thousand phages displaying the protein of interest have been reported (Jestin et al., 1999, Angew. Chemi. Int. Ed., vol. 38, pp. 1124–1127; Demartis et al., 1999, JMB, vol. 286, pp. 617–633). In such cases, a high non-specific background is expected, because of the large excess of phage particles carrying the DNA encoding the protein of interest, but not displaying said protein on the surface. To circumvent this potential problem, an affinity tag may be coupled to the C-terminal end of the protein of interest, allowing the purification of phages displaying full-length tagged protein column chromatography.

A non-limiting variety of affinity tags that may be used in this manner is: histidine tag (see Example 9), intein-chitin binding domain fusion (Chong et al., 1997, Gene, vol. 192, pp 271–281), FLAG peptide (Slootstra et al., 1997, Molecular Diversity, vol. 2, pp. 156–164), and the maltose binding protein (Pryor and Leiting, 1997, Protein Expression and Purification, vol. 10, pp. 309–319).

Accordingly, embodiments of the invention relate to
(i) a method for in vitro selection according to the second aspect of the invention, wherein the catalyst molecules of interest are enzymes or proteins that have been coupled to an affinity tag, and wherein an optional step is performed prior to step (i), the optional step comprising an enrichment for individual units displaying (full length) enzyme or protein through a purification in which the units displaying the enzyme or protein are isolated by means of the affinity tag.
(ii) a method for in vitro selection according to the second aspect of the invention, wherein the individual units displaying (full length) enzyme or protein are purified by the means of an anti-affinity-tag antibody column in which the units displaying the tagged enzyme or protein are isolated by means of the tag.

(iii) a method for in vitro selection according the second aspect of the invention, wherein the affinity tag comprises six histidine residues that are coupled to the C-terminal end of the enzyme or protein of interest, and the individual units displaying (full length) enzyme or protein are purified on a Ni-NTA column, or on a anti-histidine antibody column, in which the units displaying the tagged enzyme or protein are isolated by means of the tag.

Means of Isolating an Active Catalyst of Interest According to a Method of the Invention:

The separation of active and less active catalysts preferably involves a selective step during which the catalyzed reaction leads to either release or attachment of the catalyst through the linker-substrate attached to it.

When using the column set-up, there are at least four means to separate active from inactive catalysts. i) The active catalysts can be isolated by immobilization of the product on a product binding column (or more generally, by means of the attached product). ii) The inactive catalysts can be removed by immobilization on a substrate binding column. iii) Prior to the target reaction the catalyst may be attached to support; when a cleavage reaction occurs, the catalyst is released from support and can be collected. iv) The active catalysts may attach themselves to solid support upon reaction of substrate 1 (attached to the catalyst) and substrate 2 (attached to support). See FIGS. 7 and 8 for graphic illustrations.

The product and substrate specific columns may immobilize the product and substrate through binding to a receptor molecule with specificity for the product and substrate, respectively. Alternatively, immobilization may be mediated by a product- or substrate-specific reaction between functional groups on the column and the product or substrate attached to the catalyst.

Other means of isolating the product or substrate (and with these, the active or inactive catalysts, respectively) include partitioning between different phases, mass spectrometry, precipitation, electric or electromagnetic separation etc. In particular, electrophoresis of various kinds may be performed, especially in cases where product formation results in a significant change in the electric charge of the individual unit. A significant change in charge may result, for example, if the reaction is a ligation that ligates two substrates, one of which is charged and free in solution prior to the reaction.

Accordingly, embodiments of the invention relate to (i) a method for in vitro selection according to the second aspect of the invention, wherein the selecting for a catalyst molecule of interest, in step (ii), is done by specific immobilization resulting in said product molecule;

(ii) a method for in vitro selection according to the second aspect of the invention, wherein the selecting for a catalyst molecule of interest, in step (ii), is done by the following strategy,
 (a) constructing a system wherein substantially each of the individual units in step (i) of the second aspect comprising the substrate molecule and the catalytic molecule is bound to a matrix and wherein the unit is released from said matrix when the substrate is converted into the product; and
 (b) selecting for the unit(s) which are released from said matrix;

(iii) a method for in vitro selection according to the second aspect of the invention, wherein the selecting for a catalyst molecule of interest (step (ii)), is done by one of the following strategies,
 (a) constructing a product-column wherein a receptor specifically binding the product is placed along the matrix of the product-column; and
 (b) adding the sample of individual units at one end of the product-column and selecting for the catalyst molecules of interest by isolating the individual unit(s) which arrive(s) latest to the opposite end on the column;

(iv) a method for in vitro selection according to the second aspect of the invention, wherein the isolation of an entity comprising information which allows the unambiguous identification of the catalyst molecule of interest (step (iii)), is done by physical or chemical procedures; or (v) a method for in vitro selection according to the immediately above aspect, wherein the physical procedure is electrophoresis.

Repeating Step (i) to (iii) One or More Times, According to Point (iv) of the Second Aspect of the Invention:

As stated above, the term "repeating step (i) to (iii) one or more times by using the information comprised in said entity of step (iii) to generate the catalyst molecule of interest and construct an individual unit comprising said generated catalyst molecules of interest and then using this individual unit as a starting material in said repetition step" according to point (iv) in the second aspect of the invention denotes that said repetition may be one time, more preferably 2 times, more preferably more than 5 times, even more preferably more than 10 times, and most preferably more than 25 times.

A Method for Producing a Catalyst Molecule of Interest, According to the Final Aspect of the Invention As stated above, in a final aspect the invention relates to a method for producing a catalyst molecule of interest comprising performing the method for in vitro selection according to the invention and the further following steps, (a) producing said isolated catalyst molecule of interest in a suitable quantity of interest by a suitable production method.

As described above, in the method for in vitro selection, according to the second aspect the invention step (iii) reads:

"(iii) isolating an entity comprising information allowing the unambiguous identification of the catalyst molecule of interest which has been capable of catalysing multiple times the reaction substrate to product, by means of a characteristic of the product."

Accordingly, the information comprised within said entity provides the possibility of producing said catalyst molecule of interest by any standard production strategy known to the skilled person.

If said catalyst molecule of interest for instance is a polypeptide of interest said standard production strategy may be a standard protocol for recombinant production of said polypeptide of interest, or if said catalyst molecule of interest for instance is an organic molecule of interest said standard production strategies may be a standard protocol for production of such an organic molecule.

EXAMPLES

Example 1
An Example of an Individual Unit Comprising the Features of the First Aspect of the Invention, Except the XY Exchange Pair.

In this example 1, the catalyst of interest is a Staphylococcal DNase (SNase); the substrate is a single stranded oligonucleotide (ssDNNA); and product is the ssDNA cleaved by a SNase of interest.

Further, a filamentous phage is used as a carrier system and an acid/base linker is used as a flexible linker.

Accordingly, the individual units in this example has following general structure:

SNase—fil. Phage—acid/base link.—ssDNA
Catalyst—Carrier system—flexible linker—substrate.
See FIG. 10 for an illustration.

In this example the "selection characteristic" of the product (i.e. cleaved ssDNA) is that said product does not bind to a matrix and the substrate (ssDNA) does bind to a matrix.

Accordingly, in this example a SNase molecule of interest is isolated by selecting for individual units which are released from said matrix. See FIG. 10 for an illustration.

MATERIALS AND METHODS

Synthesis of compounds. Fmoc-S-(2-nitro-4,5-dimethoxybenzyl)-L-cysteine 1 was synthesized by a variation of the method of Merrifield (6). Briefly, 605 mg L-cysteine (5 mmol) was suspended in 100 mL degassed ethanol/water (2:1), and 1.39 mL triethylamine (10 mmol) and 1.39 g 1-(bromomethyl)-2-nitro-4,5-dimethoxybenzene (5 mmol) were added. The mixture was stirred for 10 h at 23° C. in the dark under nitrogen and filtered. The filter cake was washed with ethanol and recrystallized from ethanol/water to provide 0.95 g S-(2-nitro-4,5-dimethoxybenzyl)-L-cysteine (3 mmol). The recrystallized product (0.8 g) was suspended in 20 ml water; 0.53 ml triethylamine (3.8 mmol) was added followed by a solution of 0.9 g 9-fluorenylmethoxycarbonyl succinate ester (2.7 mmol) in 12 mL acetonitrile and the mixture stirred for 10 h at 25° C. under nitrogen. The product precipitated upon acidification to pH 2–3 with 1 M HCl and evaporation of the acetonitrile. The precipitate was collected on a frit and washed with water and ethylacetate to remove excess HCl and reagent. The resulting crude product 1 (1.13 g) was extensively dried under vacuum, and used directly in the synthesis of the base-linker peptide $C(GGS)_4$ AQLKKKLQALKKKNAQLKWKLQALKK-KLAQGGC SEQ ID NO:9 (base sequence underlined, photoprotected cysteine in bold). Compounds 2, 3 and 4 were synthesized on an ABI DNA synthesizer on a 1 mmole scale with a 3'-biotin group (BiotinTEG CPG, Glen Research) and a 5'-thiol (5'-Thiol-Modifier C6, Glen Research) and purified by reverse phase HPLC following removal from the resin (Rainin Microsorb C18 column, flow 1 mL/min.; solvent A: 50 mM triethylammonium acetate (TEAA), pH 7, solvent B: acetonitrile, linear gradient from 5 to 50% solvent B over 40 min); the trityl protecting group on the thiol was removed according to the protocol of Glen Research. The products were lyophilized and dissolved in water (1.0 mM final concentration). The conjugate of 2 with the base-linker peptide was prepared as follows: 2 mg (415 nmole) base-linker peptide was reacted with a 20 fold molar excess of N,N'-bis(3-maleimidopropionyl)-2-hydroxy-1,3-propanediamine (3.2 mg) in 1 mL of 50 mM sodium phosphate buffer, pH 5.5, for 10 h under nitrogen at 4° C. Compound 5 was purified from the reaction mixture by reverse phase HPLC (Vydac RP-18 column, flow 2 mL/min; solvent A: 0.1% TFA in water, solvent B: 0.1% TFA in acetonitrile; linear gradient from 10 to 55% solvent B over 35 minutes), and the product fractions concentrated to approximately 0.3 mL ($OD_{280}$=6, compound 5 should not be concentrated to dryness). To 100 mL (138 nmoles) of this solution was added 75 ul water, 75 mL of aqueous 1 M aqueous sodium phosphate, pH 7, 30 mL of aqueous 5 M NaCl, and 22 mL (22 nmoles) of compound 2, and the reaction incubated for 10 h under nitrogen at 23° C. (to avoid precipitation the reagents should be added in this order). The product was purified by anion exchange FPLC (Mono Q HR 5/5 column (Pharmacia), flow 0.75 mL/min solvent A: 20 mM Tris-HCl, pH 7, solvent B: 20 mM Tris-HCl, pH 7, 2 M NaCl; linear gradient from 20 to 60% B in 7.5 min); on a 10% denaturing polyacrylamide gel the product ran as a single band. Fractions of $OD_{260}$=0.3–1 were used directly for the photo-deprotection step (vide infra). The conjugates of 3 and 4 with the base-linker-peptide were prepared as follows: approximately 200 nmoles of either 3 or 4, and a 20 fold excess of bismaleimide were incubated in 1 mL of aqueous 50 mM phosphate buffer, pH 5.5, at 4° C. for 15 hours. After purification by reverse phase HPLC and lyophilization, the identity of compounds 6 and 7 was verified by Maldi-ToF MS. Either 6 or 7 (150 nmoles) was then incubated with 100 nmoles base-linker-peptide in 100 mL of 10 mM TEAA, pH 6.5, 100 mM NaCl for 15 hours at 4° C. The products were purified by reverse phase HPLC (Vydac RP-18 column, conditions as described above), lyophilized and analyzed by Maldi-ToF MS (7). The 2-nitro-4,5-dimethoxybenzyl protecting group on the C-terminal cysteine of the three conjugates was removed by photolysis to afford compounds 8, 9 and 10 as follows: for compound 8, 100 mL of the FPLC purified fraction containing the protected conjugate (vide supra) was degassed thoroughly with argon for 15 min, and then exposed to a mercury lamp (450 W high pressure mercury lamp, Ace-Hanovia; Pyrex™ filter, cutoff$^2$ 300 nm) in a septum capped glass vial for 30 min (8). For compounds 9 and 10, 10 nmole of the conjugate was dissolved in 100 mL of 10 mM DTT, degassed and photolyzed as described above. After 30 min of irradiation no remaining starting material could be detected by MALDI-ToF MS. The reaction mixture was separated by HPLC (Vydac RP-18 column, conditions as described above) and the product fractions were lyophilized. The conjugates were stored frozen, and used within a week after photo-deprotection, to ensure efficient attachment to phage.

Construction of acid helper phage. A NarI restriction site was introduced between the third and fourth codon of mature pIII protein of M13K07 helper phage (Promega) by Kunkel mutagenesis (9) with the primer K07-NarI-prim (5'-ACAACTTTCAACGGCGCCAGTTTCAGCGG-3') SEQ ID NO:10 to give NarI-helper phage. DNA encoding the amino acids GA AQLEKELQALEKENAQLEWELQALEKELAQ-GGC PAGA SEQ ID NO:11 (acid peptide sequence underlined, GGC motif in bold) with a NarI restriction site at both ends, was produced by polymerase chain reaction (PCR) with the plasmid pCRII acid (Ellis L. Reinherz, Dana Farber Cancer Institute, Boston) with the primers NarIfwd (5'-ACTACAAATTGGCGCCGCTCAGCTCGAAAAAG AGC-3') SEQ ID NO:12 and NarIbck (5'AATTATAGGCG CCAGCCGGGCAACCGCCCTGAGCCAGTTCCTTT TCC-3') SEQ ID NO:13. The PCR product was digested with NarI and inserted into NarI digested NarI-helper phage to afford acid helper phage.

Construction of phagemids encoding the staphylococcal nuclease-pIII fusion and 39-A11 Fab-pIII fusions. To make the SNase-pIII fusion, PCR was performed on the plasmid pONF1 (10), carrying the gene encoding SNase, with primers 5'-CGCGAATTGGCCCAGCCGGCCATGGCCGCAACTTCAACTAAA-3' SEQ ID NO:14 (SfiI restriction site underlined) and 5'-GCGAATTGGTGCGGCCGCTTGACCTGA-ATCAGCGTTG-3' SEQ ID NO:15 (NotI restriction site underlined). The product was digested with SfiI and NotI and inserted into SfiI-NotI digested pFAB-5c.His, a derivative of plasmid pFAB-5c (11), to give phagemid pII78-6. As a negative control the phagemid pComb3H.DA was employed. This phagemid (12) carries the 39-All Fab antibody (13) fused to the pIII protein. The expression of both the SNase and control protein is driven by the lac promoter.

Production of phage particles. Phage particles were produced with minor modifications according to Ørum et al. (11). Briefly, E. coli XL1-blue was transformed with pII78-6 or pComb3H.DA, and shaken at 37° C. in 2×YT broth and 100 mg/mL ampicillin. At an $OD_{600}$ of 0.5, acid helper phage was added to a final concentration of $1.5 \times 10^8$ cfu/mL, and incubated at 37° C. for 20 min. The cells were pelleted and resuspended in 2×YT, 100 mM IPTG, 100 mg/mL ampicillin, 50 mg/mL kanamycin, and shaken for 14 hours at RT. Cells were pelleted and phage particles in the supernatant were PEG precipitated, followed by resuspension in TBS (25 mM Tris-HCl, pH 7.4, 140 mM NaCl, 2.5 mM KCl). Phage titrations were performed with E. coli XL1-blue using standard procedures (14).

Covalent attachment of base-linker-substrate conjugates to phage. Approximately $10^8$ phage particles were incubated in 40 mL buffer A (TBS, 10 mM EDTA, 0.1% BSA), supplemented with 1 mM mercaptoethylamine (MEA) and 1 nmole of either base-linker-oligodeoxynucleotide (8), base-linker-pTp (9) or base-linker-pTpTp (10), at 37° C. for 60 minutes, then PEG precipitated twice and resuspended in buffer A.

Phage immobilization and release from solid support. Approximately $10^8$ phage particles, covalently attached to the baselinker-substrate conjugates, were incubated with 50 mL magnetic streptavidin beads (Boehringer Mannheim, biotin binding capacity: 1.5 nmole/mL) in 1 mL buffer A for 15 minutes at 23° C.; eight 1 min washes were performed in buffer A with 0.1% Tween 20, followed by two 1 min washes in buffer A. The number of phage immobilized on the beads was determined by suspending the beads in buffer A, and then either directly infecting E. coli XL1-blue with the bead suspension and titering or alternatively, infecting after treatment of the beads with DNase 1 (1 unit/mL DNase 1, 10 mM $MgCl_2$, 20 mM Tris-HCl, pH 8, 23° C. for 15 min). Calcium-dependent release (cleavage) from solid support was examined by suspending beads in buffer B (TBS, 10 mM $CaCl_2$, 0.1% BSA), incubating at 23° C. for 5 min, and titering the supernatant. Calcium-independent release from the beads (leakage) was determined by resuspending the beads in buffer A, incubating for five minutes at 23° C., and titering the supernatant.

Enrichment of active enzymes from a library-like ensemble. Phage particles displaying SNase or 39-A11 Fab were mixed in a 1:100 ratio and the base-linker-oligodeoxynucleotide conjugate (8) was covalently attached. Phage were then immobilized on magnetic streptavidin beads, washed in buffer A, and incubated in buffer B as described above, E. coli XL1-blue were infected with the supernatant and the cells plated on a LA plate containing 100 mg/mL ampicillin. Randomly picked colonies were identified as SNase- or control clones by PCR or restriction enzyme digestion.

RESULTS & DISCUSSION

Selection scheme. To test the above strategy for directed-enzyme evolution in a phage-display format, it was first necessary to develop a general method for selectively attaching a given substrate to or near a phage-displayed enzyme. Importantly, the substrate must be attached so that it can bind productively in the active site of the conjugated enzyme. Moreover, the substrate should be covalently linked to the phage to ensure that there is no crossover of reaction product between members of the library. One possible strategy involves selective chemical modification of the enzyme or a nearby phage coat protein (e.g., pIII protein) with substrate by a disulfide exchange reaction. For example, a cysteine residue introduced near the active site of staphylococcal nuclease through site-directed mutagenesis has been used to selectively introduce unique chemical functionality by a disulfide exchange reaction (15). To apply this method to proteins expressed on filamentous phage, the three single cysteines of the pVI, pVII and pIX coat proteins were first mutagenized to alanine. The eight buried cysteine residues in the pIII protein were left unchanged, as they likely form structurally important disulfide bridges (16). Unfortunately, repeated attempts to selectively modify unique cysteine residues introduced near the active site of several enzymes displayed on phage, by either disulfide exchange, maleimide addition or alkylation reactions, resulted in significant nonspecific labelling of phage coat proteins. No conditions or reagents were found that made possible selective labelling of the pIII fusion protein containing the unique surface cysteine residue. It is likely that the thousands of proteins constituting the phage coat make the specificity requirement for a chemical reaction too great; also, the probability of cysteine misincorporation due to the intrinsic error rate in protein biosynthesis becomes significant for such a large ensemble of proteins. Alternatively, the cysteine residues in the pIII protein may be accessible to crosslinking reagents.

To circumvent these problems, a two step process was developed in which chemical crosslinking is preceded by the selective formation of a noncovalent complex at the site of modification (FIGS. 9 and 10). The complex is a heterodimeric coiled-coil consisting of a synthetic basic peptide B C(GGS)$_4$ AQLKKKLQALKKKNAQLKWKLQALKKKLAQGGC SEQ ID NO:9, to which substrate is covalently coupled before heterodimerization, and an acidic peptide A, GA AQLEKELQALEKENAQLEWELQALEKELAQGGCP AGA SEQ ID NO:11 that is expressed as an N-terminal fusion to the pIII coat protein of filamentous phage. The acid and base peptides (underlined) were chosen as dimerization domains because of their small size (thirty amino acids) and high tendency to form stable, parallel heterodimeric coiled-coil structures—the acid—acid and base—base homodimers form $10^5$ fold less efficiently than the heterodimer (17). Heterodimerization of the synthetic (B) and phage-encoded (A) peptides should bring the substrate into close proximity of the displayed enzyme, and lead to spontaneous disulfide bond formation between cysteines on each of the peptides (FIG. 10). The tripeptide Gly-Gly-Cys was added to the C-termini of the acid and base peptides to facilitate formation of a disulfide bridge between the two helices (17). The substrate is covalently linked to the basic peptide B through a flexible linker to facilitate productive binding of substrate to enzyme (FIG. 9). The acidic peptide A is fused to the pIII protein of the phage rather than to the displayed enzyme itself for the following reasons: (i) insertion of the acid peptide sequence into an enzyme might interfere with enzyme function; (ii) the flexible linker of the base-linker-peptide as well as hinges in the pIII protein and a peptide linker inserted between pIII and the displayed enzyme, should allow many possible orientations of the substrate relative to the enzyme active site; and (iii) it should be possible to use a single helper phage bearing the acid peptide extension to display many enzyme-substrate pairs, rather than having to engineer into each enzyme a functional conjugation site.

Generation of the Acid Helper Phage and Base-linker-substrate Conjugate.

To attach the base-linker-substrate conjugate to phage we introduced the acidic peptide A at the N-terminus of pIII protein in the M13K07 helper phage. The enzyme library is fused to the N-terminus of the pIII coat protein; this construct is carried in the phagemid. Upon superinfection by helper phage, phage particles are produced that contain the phagemid DNA but whose coat consists (with one exception) of proteins encoded by the helper phage genome. The one exception is the pIII protein, present in 4–5 copies at one tip of the phage. During packaging of the phage, both enzyme-pIII fusions and acid peptide A-pIII fusions are produced; the phage particles obtained from a typical preparation carry either one or zero enzyme-pIII fusions plus three to five copies of acid peptide A-pIII fusion.

To generate phages bearing an acid peptide-pIII fusion, DNA encoding the acidic peptide A with a C-terminal extension containing a cysteine residue, was introduced into the 5'-end of gene III of the M13K07 helper phage. The resulting acid helper phage particles were immobilized more than hundred fold more efficiently than M13K07 on an ELISA-plate coated with basic peptide B, indicating that the mutant helper phage carry accessible acid peptide extensions on their pIII proteins. Likewise, when *E. coli* containing a phagemid encoding a pIII fusion protein were superinfected with the acid helper phage, the resulting phage particles displayed modified pIII extensions in addition to the pIII fusion protein (FIG. 10). The insertion of the acid peptide did not appear to change the titer or rescue efficiency of the helper phage significantly.

The synthetic base-linker-peptide (B) to which substrate is attached consists of the twelve residue $(GlyGlySer)_4$ linker followed by the thirty amino acids constituting the base sequence (FIG. 9). The base-linker peptide also contains cysteine residues at the N-and C-termini that allow efficient, selective coupling of the peptide to substrates and disulfide bond formation to phage, respectively (FIGS. 9 and 10). The C-terminal cysteine of the synthetic peptide is initially protected with the photochemically removable 2-nitro-4,5-dimethoxybenzyl protecting group. This allows substrate to be selectively conjugated by a thiol specific reaction (e.g., by disulfide exchange, alkylation, or Michael addition reactions) to the free thiol group of the N-terminal cysteine. After substrate conjugation, the C-terminal cysteine is photochemically deprotected in high yield to generate a free thiol available for crosslinking to the acid peptide extension on phage. Because the chemical conjugation of substrate and base-linker peptide, and the crosslinking of this conjugate to phage are carried out separately, many different chemistries and reaction conditions can be used to couple the base-linker peptide and substrate. Moreover, the composition of the conjugate can be purified and characterized (e.g., by mass spectrometry) before it is crosslinked to phage.

Staphylococcal nuclease as a model system. The enzyme staphylococcal nuclease is a well-characterized enzyme consisting of a single polypeptide chain 149 amino acids in length (18). The enzyme preferentially hydrolyzes the phosphodiester bonds of single-stranded RNA (ssRNA), ssDNA, and duplex DNA at A,U- or A,T- rich regions to generate 3'-phosphate and 5'-hydroxyl termini (18). $Ca^{2+}$ is required for enzymatic activity, providing a mechanism for modulating enzyme action. In addition, SNase has successfully been displayed as a pIII fusion protein on phage (19).

Because no reagent, antibody or receptor is available that can easily distinguish between a single-stranded oligodeoxynucleotide substrate and its cleavage product (a complementary oligonucleotide would be degraded), a selection scheme was developed in which enzymatic cleavage of ssDNA substrate results in release of phage from solid support. In this scheme, one round of selection involves the following steps: i) attachment of phage displaying SNase to solid support through a single-stranded oligodeoxynucleotide (in the absence of $Ca^{2+}$ to inactivate SNase); ii) removal of unbound phage by washing; iii) initiation of the cleavage reaction by addition of $Ca^{2+}$, and iv) isolation of eluted phage. In later rounds of selection, elution can be done under increasingly stringent conditions, eg., shorter reaction time, lower temperature and altered pH. Attachment of phage to solid support is carried out by coiled-coil formation between 5'-biotinylated oligodeoxynucleotide-peptide B conjugates and acid peptide A extensions on phage, followed by disulfide crosslinking of the two peptides and immobilization on streptavidin beads (FIG. 9). This scheme, in which the phage is attached to solid support through the substrate, requires that the enzyme or substrate be maintained in an inactive state during attachment to phage, and then be activated by a change in reaction conditions. Such changes can include modulation of pH, addition of cofactors or co-substrates, and photochemical or chemical activation of the substrate. In the case of biomolecular condensation reactions in which bond formation results in phage immobilization on solid support, it is not necessary to initiate the reaction; the same is true if capture of active enzymes is by a product-specific reagent, antibody or receptor.

Covalent attachment of the substrate to phage. Phage displaying either SNase or a control protein (antibody 39-A11 Fab fragment) were prepared by superinfection with the acid helper phage. To evaluate the efficiency of the attachment of base-linker-substrate conjugates to phage, an excess of a control conjugate, "pTp"-peptide B (compound 9), was incubated with the phage. The base-linker-pTp conjugate consists of a biotin moiety, followed by deoxythymidine-3',5-diphosphate (pTp), the flexible peptide linker and base peptide sequence, and a C-terminal cysteine. The base-linker-pTp conjugate is not a substrate for wild-type SNase in solution (pTp is a potent inhibitor of SNase) (20). Phage and the substrate-peptide B conjugate were first incubated with the reducing agent mercaptoethylamine (MEA) to reduce disulfide bonds between cysteines on the phage acid peptide or the synthetic peptide. Then, MEA and free base-linker-pTp were removed by PEG precipitation, and magnetic streptavidin beads were added. After ten washes, the number of phage that were immobilized was determined by infection of *E. coli* XL1-blue with the beads, and titering phage. When measured this way, the efficiency of phage immobilization was approximately 10%, for both phage displaying SNase and 39-All Fab (FIG. 11).

Next it was determined whether an oligodeoxynucleotide substrate attached to phage displaying SNase would be stable in the absence of $Ca^{2+}$. The base-linker-oligodeoxynucleotide conjugate was attached to phage displaying SNase (in the presence of EDTA), and the immobilization efficiency determined as above. The efficiency of immobilization was again approximately 10% (FIG. 11), indicating that the tethered oligode-oxynucleotide substrate is not cleaved by SNase in the absence of $Ca^{2+}$. It is possible that the true immobilization efficiency is higher than observed if some of the phage are rendered non-infective when attached to the beads. This notion was tested by addition of DNase I, which should cleave the tethered oligodeoxynucleotide substrate and release the immobilized phage. As can be seen in FIG. 11, most of the immobilized phage are non-infective, but become infective upon addition of DNase I, indicating that the true immobilization efficiency is about 80% (FIG. 11). If the oligodeoxynucleotide-peptide B conjugate is not included, less than 0.01% of the phage become immobilized; if the wildtype M13K07 helper phage is used to superinfect, about 0.3% of phage are immobilized. It thus appears that the two-step protocol for attachment of substrate to phage pIII protein is efficient and highly site-specific.

Enzyme dependent cleavage of phage from solid support and enrichment. To determine whether phage-displayed SNase is capable of specifically cleaving the tethered oligodeoxynucleotide substate in an intramolecular reaction, $Ca^{2+}$ was added to the immobilized phage to activate the enzyme. Approximately 15% of the phage were released (FIG. 11), in contrast to release of only 0.2% of the control phage displaying Fab 39-A11 (FIG. 11). This experiment demonstrates that SNase cleaves and releases phage from the solid support much more efficiently than the control protein, as expected. However, it appears that a small but significant fraction of the phage leak off the support during the assay (this background leakage is observed without $Ca^{2+}$, for both the base-linker-oligodeoxynucleotide and base-linker-pTp conjugates, and for both displayed proteins, FIG. 11. Addition of $Ca^{2+}$ leads to an initial burst of phage release from support; however, the release of phage quickly declines to a level corresponding to the leakage observed without $Ca^{2+}$. This result demonstrates that phage released into solution by intramolecular cleavage events do not release other phage from support as a result of intermolecular cleavage reaction. Cross-reactivity therefore does not appear to be significant, even with a very active enzyme like SNase.

The above analysis suggests that it should be possible to enrich phage displaying SNase from a library-like ensemble of phage displaying catalytically inactive proteins. To test this, phage displaying SNase and the Fab 39A-11 control protein were mixed in a ratio of 1:100, crosslinked to the oligode-oxynucleotide-peptide B conjugate and immobilized. After incubation with $Ca^{2+}$, the ratio of recovered phage was 22:18, which corresponds to an enrichment factor slightly higher than 100. This degree of enrichment should be sufficient to isolate an active catalyst from a library of $10^{10}$ members after five rounds of selection and amplification.

The enrichment factor can likely be increased by minimizing background leakage of phage from support. This leakage may result from release of streptavidin from support, or alternatively, reduction or incorrect formation of the disulfide bridge between the synthetic and phage encoded peptides. We are currently exploring these possibilities. Alternatively, the enrichment factor can be increased by increasing the extent of the enzyme-catalyzed cleavage reaction. Under the conditions of phage production, the ratio of pIII expressed from the helper phage relative to the pIII fusion protein expressed from the phagemid is such that most of the phage carry only wildtype pIII proteins; only a minor fraction of the phage carry the protein-pIII fusion. The number of phage that can cleave themselves off can be increased simply by increasing the number of phage that display the enzyme. For the phagemid/helper phage combination described here, we estimate that only about 15% of the phage are monovalent. By appropriate vector design and phage preparation, it should be possible to increase the average display to about one protein per phage. This should increase the cleavage to leakage ratio 7 fold, and hence, increase the enrichment factor of active versus inactive enzymes from the present ~100 to about 700.

To examine whether the selection scheme described here can be used for reactions that involve small molecule substrates, a pTpTp-peptide B conjugate (compound 10) was attached to phage displaying SNase or the control protein. Phage were carried through the enrichment routine described above, and again SNase displaying phages were enriched. MALDI-ToF mass spectrometry was used to show that the pTpTp substrate was cleaved at the phosphodiester bond between the two thymidines; no side products were detected. It thus appears that the methodology is applicable to both macromolecular and small molecule substrates. We are currently exploring the possibilities for isolating novel catalysts from libraries of enzyme or antibody origin.

Most enzyme libraries displayed on phage require superinfection by a helper phage like M13K07. The selection protocol described here can therefore be applied directly to these libraries—one simply needs to prepare phage after superinfection of the phagemid encoded library with the acid peptide helper phage, and conjugate the substrate of choice to the basic peptide B. Likewise, this methodology can be applied to populations of structurally diverse proteins. The collection of proteins encoded by a genome is one such population. For example, it should be possible to isolate natural kinases with predefined substrate specificity from a genomic protein library using this selection scheme. This type of functional cloning in which a natural enzyme (and the gene that encodes it) is isolated on the basis of its catalytic activity should be applicable to many reactions catalyzed by natural enzymes.

References and Notes used in example 1

1. Schultz, P. G. & Lerner, R. A. (1995) *Science* 269, 1835–1842.
2. (a) Marks, J. D., Hoogenboom, H. R., Bonnert, T. P., McCafferty, J., Griffiths, A. D. & Winter, G. (1991) *J. Mol. Biol.* 222, 581–597. (b) Barbas, C. F., III, Bain, J. D., Hoekstra, D. M. & Lerner, R. A. (1992) *Proc. Natl. Acad. Sci. U.S.A.* 89, 4457–4461. (c) Griffiths, A. D., et al. (1994) *EMBO J.* 13, 3245–3260.
3. Janda, K. D., Lo, C-H. L., Li, T., Barbas, C. F., III, Wirsching, P. & Lerner, R. A. (1994) *Proc. Natl. Acad. Sci. U.S.A.* 91, 2532–2536.
4. (a) Soumillion, P., Jespers, L., Bouchet, M., Marchand-Brynaert, J., Winter, G. & Fastrez, J. (1994) *J. Mol. Biol.* 237, 415–422. (b) Janda, K. D., Lo, L-C., Lo, C-H. L., Sim, M. M., Wang, R., Wong, C-H. & Lerner, R. A. (1997) *Science* 275, 945.
5. Gao, C., Lin, C. H., Lo, C-H. L., Mao, S., Wirsching, P., Lerner, R. A. & Janda, K. D. (1997) *Proc. Natl. Acad. Sci. U.S.A.* 94, 11777–11782.
6. Erickson, B. W. & Merrifield, R. B. (1973) *J. Am. Chem. Soc.* 95, 3750–3756.
7. Piles, U., Zürcher, W., Schär, M. & Moser, H. E. (1993) *Nucl. Acids. Res.* 21, 3191–3196.
8. Marriott, G. & Heidecker, M. *Biochem.* (1994) 33, 9092–9097.

9. Kunkel, T. A., Roberts, J. D. & Zakour, R. A. (1987) Methods in Enzymology 154, 369.
10. Hibler, D. W., Barr, P. J., Gerlt, J. A. & Inouye, M. (1985) J. Biol. Chem. 260, 2670–2674.
11. Ørum, H., Andersen, P. S., Øster, A., Johansen, L. K., Ri-ise, E., Bjørnvad, M. Svendsen, I. & Engberg. J. (1993) Nucl. Acids Res. 21, 4491–4498.
12. Schultz, P. G. & Romesberg, F. E. unpublished results.
13. Romesberg, F. E., Spiller, B., Schultz, P. G. & Stevens, R. C. (1998) Science 279, 1929–1933.
14. Sambrook, J., Fritsch, E. F. & Maniatis, T. (1989) "Molecular Cloning: A Laboratory Manual," 2nd Ed. Cold Spring Harbor Lab., Cold Spring Harbor, N.Y.
15. Pei, D., Corey, D. R. & Schultz, P. G. (1990) Proc. Natl. Acad. Sci. 87, 9858–9862.
16. (a) Lubkowski, J., Hennecke, F., Pluckthun, A. & Wlodawer, A. (1998) Nature Structural Biology 5, 140–147. (b) Kremser, A. & Rasched, I. (1994) Biochemistry 33, 13954–13958.
17. (a) O'Shea, E. K., Rutkowski, R., Kim, P. S. (1989) Science 243, 538–542. (b) O'Shea, E. K., Rutkowski, R., Stafford, W. F. III & Kim, P. S. (1989) Science 245, 646–648. (c) O'Shea, E. K., Klemm, J. D., Kim, P. S. & Alber, T. (1991) Science 254, 539–544. (d) xZhou, N. E., Kay, C. M. & Hodges, R. S. (1993) Biochemistry 32, 3178–3187.
18. (a) Cotton, F. A., Hazen, E. E., Jr., & Legg, M. J. (1979) Proc. Natl. Acad. Sci. U.S.A. 76, 2551–2555. (b) Tucker, P. W., Hazen, E. E., & Cotton, F. A. (1978) Mol. Cell. Biochem. 22, 67–77. (c) Sondek, J. & Shortle, D. (1990) Proteins 7, 299–305. (d) Hale, S. P., Poole, L. B. & Gerlt, J. A. (1993) Biochemistry, 32, 7479–7487. (e) Hynes, T. R. & Fox, R. O. (1991) Proteins 10, 92–105. (f) Loll, P. J., Quirk, S., Lattman, E. E. & Gravito, R. M. (1995) Biochem. 34, 4316–4324. (g) Judice, K., Gamble, T. R., Murphy, E. C., de Vos, A. M. & Schultz, P. G. (1993) Science 261, 1578–1581.
19. Ku, J. & Schultz, P. G. (1994) Biomed. Chem. Lett. 2, 1413–1415.
20. Tucker, P. W., Hazen, E. E., Jr. & Cotton, F. A. (1979) Mol. & Cell. Biochem. 23, 3–16.

Example 2

Isolation of Lipase Variants, Using Phage-displayed Lipase as the Catalyst and DNA Oligos as the XY Exchange Pair This is an example of the selection scheme depicted in FIG. 8:

Phagemid Construction.

The PCR-product obtained by using the *Humicola lanuginosa* lipase gene (SP400) as template and the primers Fwd: GTCACAGATCCTCGCGAATTGGCCCAGC-CGGCCATGGCCGAGGTCTCGCAGGATCT-GTTTAACCAGTTC SEQ ID NO:9, and Rev: CAGTCA-CAGATCCTCGCGAATTGGTGCGGCCGCAAGACA TGTCCCAATTAACCCGAAGTACC SEQ ID NO:17, was digested with SfiI and NotI restriction enzymes and inserted into SfiI and NotI digested phagemid pFab5C (Ørum et al., 1993, NAR 21:4491–4498). The resulting phagemid, pFab-SP400, carries a gene fusion shown SEQ ID NO: 1 which comprises (reading from the N-terminal end) the pelB signal sequence (underlined), the gene encoding mature lipase, and the pIII gene from amino acid residue 198 (underlined). The pFab-SP400 lipase library comprises a number of such phagemid constructions, differing in the lipase amino acids sequence.

Production of Phage Particles.

Phage particles are produced with minor modifications according to Ørum et al. (see above). Briefly, *E. coli* Top10F' is transformed with the pFab-SP400 lipase library, and shaken at 37° C. in LB medium containing 100 μg/mL ampicillin. At an $OD_{600}$ of 0.5, acid helper phage (a M13K07 derivative, carrying a 30'meric acid peptide extension at the N-terminus of pIII, see Pedersen et al., PNAS (1998), in press) is added to a final concentration of $1.5 \times 10^8$ cfu/mL, and incubated at 37° C. for 20 min. The cells are pelleted and resuspended in LB, 5 μM IPTG, 100 μg/mL ampicillin, 50 μg/mL kanamycin, and shaken for 6–8 hours at 37° C. Cells are pelleted and phage particles in the supernatant PEG precipitated, followed by resuspension in TBS (25 mM Tris-HCl, pH 7.4, 140 mM NaCl, 2.5 mM HCl). PEG precipitation and resuspension is repeated, and finally the phage are sterile filtrated.

Synthesis of Base-linker-DNA Conjugate ("Base-linker-X"),

The photoprotected and F-moc protected compound, Fmoc-S-(2-nitro-4,5-dimethoxybenzyl)-L-cysteine 1 is synthesized. The resulting crude product is extensively dried under vacuum, and used directly in the synthesis of the base-linker peptide $C(GGS)_4$ AQLKKKLQALKKKNAQLKWKLQALKKK-LAQGGC (base sequence underlined, photoprotected cysteine in bold). A DNA oligo of approximate length and sequence 5'-SH-GGGAAGAACCC-3' is synthesized with a 5'-thiol (5'-Thiol-Modifier C6, Glen Research) and purified by reverse phase HPLC following removal from the resin; the trityl protecting group on the thiol is removed according to the protocol of Glen Research. The products are lyophilized, dissolved in water and conjugated to the base-linker peptide as follows: Base-linker peptide is reacted with a 20 fold molar excess of N,N'-bis(3-maleimidopropionyl)-2-hydroxy-1,3-propanediamine in sodium phosphate buffer, pH 5.5, for approximately 10 hours under nitrogen at 4° C. The resulting product is purified from the reaction mixture by reverse phase HPLC. The buffer is adjusted to sodium phosphate, pH 7, NaCl is added to avoid precipitation, and the DNA oligo described above is added, and the solution incubated at RT for approximately 10 h under nitrogen. The product is purified by anion exchange FPLC, and product fractions are used directly for the photo-deprotection step. In the photodeprotection step the 2-nitro-4,5-dimethoxybenzyl protecting group on the C-terminal cysteine is removed by photolysis as follows: The protected conjugate (vide supra) is degassed thoroughly with argon and then exposed to a mercury lamp in a septum capped glass vial for 30 min, to yield the deprotected base-linker-DNA conjugate.

The Y-substrate-column moiety to be used in this selection is prepared by coupling 5'-thiol-modified DNA oligos of approximate length and sequence 5'-SH-CCCTTCTT-3' and 5'SH-TTCTTGGG to a p-nitro-phenyl-butyrate ester or p-nitro-phenyl-palmitate ester, eg. by reaction of the thiolated DNA with a maleimide unit on the butyrate or palmitate. The product is then attached to the column matrix through either the ortho or meta position by specific reaction with a functional group on the matrix.

Covalent Attachment of Base-linker-DNA Conjugate to Phage.

Approximately $10^{10}$ phage particles are incubated in 4 mL TBS, 10 mM EDTA, 0.1% BSA, 1 mM mercaptoethylamine (MEA) and 100 nmole of base-linker-DNA, at 37° C. for 60 minutes, then PEG precipitated twice and resuspended in lipase buffer (50 mM Tris-HCl pH 7.5, 0.3 mM CaCl, 0.1 mM MgCl2, 0.1% Triton X-100).

Pre-sorting Phages to Which the Base-linker-DNA Conjugate has Been Attached.

To get rid of phages to which a base-linker-DNA conjugate has not been attached, phages that have gone through the covalent attachment procedure described above are loaded on an affinity-column carrying DNA oligos of a sequence complimentary to the DNA in the base-linker-DNA-conjugate (e.g., the sequence GGGMGAACCC). Phages that are retarded on the column are collected.

Isolation of the Most Active Lipases in the Library.

A column to which the "DNA-pnp butyrate" has been coupled to the matrix, is equilibrated in lipase buffer. Then the phage particles to which the base-linker-DNA conjugate has been attached (see above) are loaded on the column. A titer determination is performed on each fraction collected; the fastest moving fraction that contains a significant number of phage should contain the phage carrying the more active lipases.

Example 3

Isolation of RNA-cleaving Deoxy-ribozyme Variants, Using a PCR-amplifiable DNA Library and DNA Oligos as the XY Exchange Pair (the Y Exchange Unit Consists of Two Oligos, $Y_1$ and $Y_2$, That Have Overlapping Binding Sites on the X Oligo)

DNA Library Construction.

A PCR-reaction is performed with the primers "sense": 5'-GGAAGGGATGGTCACATGCA-3' SEQ ID NO:19 and "antisense": 5'-biotin-GTCAGTTGCCAAGCTTACCG-3' SEQ ID NO:20, on the template 5'-ggaagggatggtcacatgca CTAGTTAGGCTAGCTACAACGA TTTTTCCcggtaagcttggcaactgac-3' SEQ ID NO:21 (priming sites in lower case, deoxy-ribozyme catalytic motif italicized, substrate binding sequence underlined, X exchange moiety in bold). The PCR-product is immobilized by repeated passing through streptavidin affinity columns (Genosys, The Woodlands, Texas), washed with several column-volumes of wash buffer (1 M NaCl, 0.1 mM EDTA, 50 mM Tris-HCl pH 7.5), and the non-biotinylated strand eluted with 100 mM NaOH. The single-stranded DNA molecules are ethanol precipitated, and used in the column-based selection described below. The ssDNA molecules of the ("wild-type") sequence shown above cleave RNA molecules of sequence 5'-r(GGAAAAAGUAACUAG)-3' SEQ ID NO:22 in a $Mg^{++}$ dependent reaction. The deoxy-ribozyme library (see below) comprises a number of such ssDNA-molecules, differing in the sequence between the priming sites.

Preparation of Y-RNA Target-column Matrix.

An equimolar solution of two mixed DNA/RNA oligos of sequences 5'-biotin-d(TACACG)-r(GGAAAAAGUAACUAG) SEQ ID NO:22-d(TTAGTGTCTCACCATCAT-CC) SEQ ID NO: 23 3' and 5'-biotin-d(TACACG)-r(GGAAAAAGUAACUAG) SEQ ID NO:22-d(TTAGTGTCTCGTGAATCCCT)-3' SEQ ID NO:24 (Oligos Etc., USA) are immobilized by repeated passing through streptavidin affinity columns, and washed with several column-volumes of wash buffer (1 M NaCl, 0.1 mM EDTA, 50 mM Tris-HCl pH 7.5). The Y exchange moieties $Y_1$ and $Y_2$ are in bold.

Isolation of the Most Active RNA-cleaving Deoxy-ribozymes in a ssDNA Library.

A ssDNA library (see above) is loaded on a streptavidin column on which the "$Y_1$-RNA-biotin" and "$Y_2$-RNA-biotin" target substrates (see above) have been immobilized in wash buffer. After equilibration with several column-volumes of wash buffer, flow of a reaction buffer (10 mM MgCl2, 1 M NaCl, 50 mM TrisHCl pH 7.5) is maintained for a while. Fractions are collected, and the DNA content measured (eg., by UV detection). The fastest moving fraction that contains a significant amount of DNA should contain the DNA carrying the most active magnesium-dependent RNA-cleaving molecules.

Example 4

Optimization of an Enzyme That Catalyzes Aldol Formation. In This Example a Polyhistidine Loop and an Associated Metal Ion Comprise the X Unit; a Bidentate Ligand (Ethylenediamine) Constitutes the Y Unit A ketone substrate is coupled to an ethylenediamine (EDA) moiety, the enzyme carries a polyhistidine loop. When the ketone and enzymes are mixed in the presence of an appropriate metal ion (eg., Fe), the polyhistidine and the metal ion will form a kinetically and thermodynamically stable interaction. The EDA-ketones will compete for the remaining two coordination sites of the polyhistidine-bound metal. Enzymes with aldolase activity will promote the reaction of the ketone attached to the enzyme with an aldehyde in the column buffer, to form the aldol product. Typically, this aldol with some frequency undergoes dehydration, to form an an $\alpha,\beta$-unsaturated ketone. This conjugated olefin can undergo a Michael addition reaction with the free thiols on the column, thereby immobilizing the enzyme. However, EDA-ketone conjugates in the buffer will exchange with the immobilized enzyme, and release the enzyme in its original substrate bound form. In this set-up, the His*metal-EDA represents X-Y, and the product binding moiety is a nucleophile that traps the product after water elimination. The depicted selection scheme should thus select for enzymes that efficiently catalyze the aldol and dehydration reactions.

Example 5

Examples of XY-exchange Pairs Suitable to be Incorporated in a Phage-display System as Described in Example 1

XY "Embodiments" in the Phage Display System as Describe in Example 1:

Solution 1: Synthesize base-linker-X following the guidelines from example 1, except that now X is coupled to the base-linker peptide, not the substrate (see example 2 above). Crosslink the base-linker-X conjugate to acid extensions on pIII (on the helper phage), as described in example 1 above (see FIG. 12A). Couple Y to the substrate, and perform the selection (see example 2 above).

Solution 2: Insert four, five or six histidines at the N-terminus of pIII of the helper phage, or into an exposed loop of pIII (the $His_4$ and a metal ion comprise the X moiety). To substrate attach a metal ligand (eg., bidentate or tridentate) through a flexible linker (eg., a polyethylene glycol). Mix phage and metal ligand-substrate in the presence of a metal ion of choice, then perform selection (See FIG. 12B). Solution 3: Insert the acid or $His_4$ peptide sequence into the enzyme-pIII fusion on the phagemid, preferably in the linker connecting pIII and the enzyme. Proceed as described above.

XY "Embodiments" for Proteins in General

Solution 1: Insert the acid peptide or $His_4$ sequence into an exposed loop, or at the N- or C-terminal terminus of the enzyme. Proceed as described above.

Solution 2: Introduce (at the DNA level) a unique cysteine into the enzyme, couple the X-moiety by a thiol specific reaction (eg., disulfide bond formation, addition reaction to maleimide), and proceed as described above.

Example 6

Example of an Exchange Pair Especially Suitable to be Incorporated in a Plasmid-peptide, Polysome-peptide or mRNA-peptide System In the following it is described how the exchange pair-substrate may be attached to an enzyme in a plasmid—peptide system (Schatz et al., 1996, *Meth. Enzym.*, vol. 267, pp. 171–191), polysome—peptide system (Mattheakis et al., 1994, *Proc. Natl. Acad. Sci. USA*, vol. 91, pp. 9022–9026; He and Taussig, 1997, *Nucleic Acids Research*, vol. 25, pp. 5132–5134) or mRNA—peptide system (Roberts and Szostak, 1997, *Proc. Natl. Acad. Sci. USA*, vol. 94, pp. 12297–12302). Here exemplified with the mRNA-peptide fusion system.

Design the template DNA so as to make a portion of the mRNA in the mRNA-protein fusion become a X unit (eg. include the DNA sequence 5'-GCCGAAGCGCAATGAAGGGCAACCCG-3' SEQ ID NO:25 in the template DNA) See FIG. 13A. Attach the desired substrate to a DNA Y-unit (eg. attach substrate to a mix of the two oligos Y1: 3'-TTACTTCCCGTTGGGC-5' SEQ ID NO:26 and Y2: 3'-CGGCTTCGCGTTACTT-5') SEQ ID NO:27. Then after preparation of the mRNA-peptide fusion, mix the mRNA-peptide fusion (carrying the X unit) and the substrate conjugate (carrying the Y unit), and perform substrate reloading selection, for example by applying the mix to a product binding column (see FIG. 2).

Alternatively, the X unit can be part of the linker that connects the mRNA and the encoded peptide (eg. include the DNA sequence 5'-GCCGAAGCGCAATGAAGGGCAACCCG-3' SEQ ID NO:25 in the linker that connects the mRNA and peptide), see FIG. 13B. Then mix with the substrate conjugates and perform substrate reloading selection as described above.

Example 7

Enrichment of Cells Producing the More Active Proteases in a Background of Cells Producing Less Active Protease Variants In this example, the individual unit consists of a cell, a substrate attached to the surface of that cell through an XY exchange unit, and enzymes produced and secreted by the cell (FIG. 14). Free Y-substrate in the surrounding media continuously replace substrate attached to the cell surface. Consequently, as the local concentration of secreted enzyme is much higher near the substrate attached to the cell from which it was secreted than near any of the other cells' attached substrates, there will be more product attached on a cell secreting an active enzyme than on a cell secreting a less active enzyme.

The substrate can be attached to the cell surface in many ways. For example, phospholipids, fatty acids, sterols, cholesteryl esters may be derivatized with the substrate of the target reaction. When incubated with cells, these molecules readily localize in the membrane interior, and expose the substrate on the surface of the cell. Alternatively, the substrate may be derivatized with crosslinking reagents that react with the surface constituents. Finally, the substrate may be derivatized with structures (e.g. proteins, antibodies) that bind to membrane components such as polysaccharides or membrane proteins.

The principle is here examplified in the case where the individual unit consists of a cell (for example Bacillus), attached substrate (peptide), and secreted enzyme (protease). The His6-metal-IDA or His6-metal-NTA complex is used as XY exchange unit. The selection is performed in the column format. The column matrix is coated with peptides carrying a target sequence for the protease. The peptides are attached to the column matrix at one end, and carry a polyhistidine (His6) tag at the other.

The experiment is performed as follows. Bacillus cells, secreting the protease of interest (for example c-component from *Bacillus licheniformis* or the commercial Savinase protease), are harvested in the exponential growth phase, resuspended in apropriate buffer and incubated with a bi-functional molecule that will crosslink to cell surface components. The bi-functional molecule may be a N-hydroxysuccinimide (NHS) moiety, linked to an imino-diacetic acid (IDA) or nitrilotriacetic acid (NTA) moiety. NHS reacts with primary amines on the cell surface, which covalently anchors the IDA or NTA moiety to the cell surface.

A suitable column matrix for the separation of cells (for example Sepharose or Sephadex) is coated or derivatized with a peptide target for the protease of interest (for example, in the case of the c-component, the sequence IELSEPIGNTVCHHHHHH) SEQ ID NO:28. At one end the peptide carries a polyhistidine extension. At the other end it is attached to the column matrix (for example through reaction of the N-terminal amine with NHS-activated Sepharose, Pharmacia Biotech).

The IDA- or NTA-modified cells are loaded on the peptide-modified column, in appropriate buffer (for example 2xYT or LB medium, with added $Ni^{++}$, $Zn^{++}$, $Cu^{++}$, or $Co^{++}$; temperature 35–50° C.). The flow-rate is kept below 0.5 mL/min.

The complex His6-metal-IDA (or His6-metal-NTA) forms, and thus the protease substrate becomes attached to the cell. If the cell secretes active proteases, these cleave the target, and release the cell from the column matrix; also, the His6-metal-IDA (or His6-metal-NTA) complexes are in rapid equilibrium, resulting in continuous replacement of the substrate or product with new substrate. Consequently, the cells secreting the more efficient enzymes, or cells that secrete more of an active enzyme, elute first at the bottom of the column.

The principle is tested in the following way. Cells secreting a number of protease variants, or that secretes the same protease in varying amounts, are treated as described above, and the substrate reloading protocol performed as described. Cells secreting the more efficient protease, or secreting most of the protease, will elute first.

The stringency of the selection is controlled by the density of substrate immobilized on the column matrix, and on the IDA- (or NTA-) coupling density on the cell surface. Variants with improved expression or activity at different conditions, such as salt concentration, pH or temperature may be isolated by this method.

Example 8

Isolation of Hammerhead Ribozymes, Using a DNA/RNA Hybrid Duplex as the XY Exchange Pair, and Part of the Y-unit as the Target Substrate The hammerhead is a naturally occurring ribozyme that cleaves at a specific phosphodiester to produce 3'-cyclic phosphate and 5'-hydroxyl termini with a rate ($k_{cat}$) approaching 1 min$^{-1}$ (Stage-Zimmermann et al., 1998, RNA vol. 4, pp. 875–89). The specificity is mediated by simple Watson-Crick base pairring between the ribozyme and the target and because the only requirement in the target sequence for cleavage is a U followed by A,U or C, the hammerhead can be designed to cleave virtually any RNA molecule. However, for therapeutic use the hammerhead suffers from one major drawback. When the two duplexes are extended to increase the specificity, the off-rate decreases significantly and the ribozyme fails to turn over. To search for hammerhead variants exhibiting increased cleavage rates others have performed in vitro selections from a RNA pool containing stretches of randomised sequence e.g. (Vaish et al., 1997, Biochemistry, vol. 36, pp. 6495–501). However the selection protocol has in all reported studies been based on a single round of cleavage. Using the substrate reloading strategy the ribozyme must release itself multiple times from an immobilised matrix to be eluted from the column. The salt concentration, temperature and duplex length in the experiment described below is optimized in order for the ribozyme to rapidly liberate the substrate after cleavage. The liberated ribozyme quickly binds a new target stabilised by two coaxial stacked 5 bp helices. This rapid X-Y exchange is accomplished by the fact that Y is cleaved into half by the ribozyme, thereby destabilizing the X-Y interaction (see FIG. 3A). When applying a continues flow of buffer through the column the faster cleaving ribozyme elutes first.

To eliminate the potential selection of RNA molecules, that due to competing internal structures or misfolding, exhibits a slow substrate binding (and therefore a rapid elution profile), a pre-selection for molecules that efficiently will interact with an uncleavable DNA-substrate oligo, can optionally be performed (See FIG. 15B).

To demonstrate the principle we have chosen to randomise 7 positions within the conserved core of the ribozyme (See FIG. 15). This corresponds to 16384 different molecules, one of which corresponds to the wild type hammerhead exhibiting a cleavage rate of approximately 1 min$^{-1}$ (Stage-Zimmermann et al., 1998, RNA, vol. 4, pp. 875–89). Since our library in the experiment described below contains more than $10^{13}$ RNA molecules we expect to isolate the wild type ribozyme or a ribozyme with at least the rate of the wild type.

Outline of the Experiment

Materials:
1. RNA library (approximately 100 µg) as shown in FIG. 15 is produced by conventional techniques (in vitro transcription by T7 RNA polymerase using a randomised synthetic DNA oligo as template). The library is purified by PAGE and redissolved in column buffer and stored in 10 µg aliquots at −80° C.
2. NHS activated Sepharose for coupling of the substrate oligo (through 2-amino-1-(2-pyrridyldithio)-ethane) and a siliconized glass column (0.2 cm×10 cm)
3. Substrate RNA oligo (FIG. 15) is synthesised by conventional chemistry and HPLC purified. A 5'-thiophosphate-HEG-spacer is incorporated at the 5'-end. (5'-thiophosphate-HEGspacer-AGCUGUCACUCC-3') SEQ ID NO:29.
4. Counter selection DNA oligo (FIG. 15B) based on deoxynucleotides is synthesised by conventional chemistry (5'-thiophosphate-HEGspacer-AGCTGTCACTCC-3') SEQ ID NO:30.
5. Column buffer (10 mM MgCl$_2$, 50 mM Tris/HCl pH 7.5)

Experimental Procedure
(The DNAcounter Selection—step 2–4—is optional)
1. 100 nmol of RNA substrate oligo or 100 nmol of counter selection DNA oligo is loaded on a 1 ml bed volume NHS activated Sepharose, derivatized with the activated disulfide, in a 0.2 cm diameter, 10 cm long siliconized glass column and equilibrated with 5 volumes of column buffer immediately before use.
2. The RNA library is loaded onto the DNA oligo column and washed with 10 volumes of column buffer at 20° C. and a flow speed of 1 ml/min.
3. The column temperature is adjusted to 60° C. and the RNA is eluted in two column volumes of H$_2$O.
4. The buffer is adjusted to 0.25 M NaOH pH 6.0 and the RNA is precipitated with 2.5 Vol EtOH and redisolved in 20 ml of column buffer.
5. This sample is incubated at 37° C. for 5 mins to renature the RNA and carefully loaded on the RNA column. The temperature should be adjusted in the range 25–50° C. for optimisation of the subsequent selection. The flow rate should be kept below 0.5 ml/min to allow substrate reloading of the ribozymes.
6. Samples are collected from the bottom of the column and tested individually for ribozyme activity by standard methods (Vaish et al., 1997, Biochemistry, vol. 36, pp. 6495–501).
7. Ribozymes from the earliest collected pools exhibiting ribozyme activity is reverse transcribed using a 3' end complimentary primer and PCR amplified using up- and downstream matching primers. A T7 promoter is included in the upstream primer which enables subsequent transcription. The DNA pool is cloned in a plasmid and individual clones are analysed by sequencing. Ribozymes from individual clones are produced by T7 transcription and tested.

Example 9

Pre-enrichment of Phages Displaying His-tagged Proteins

Certain proteins are difficult to display on filamentous phage. In particular, large proteins or proteins which have a toxic or growth inhibiting effect on E. coli often have low display efficiency, i.e. the majority of phage particles produced carry no pIII-fusion on the surface. Display efficiencies as low as one out of a thousand phages displaying the fusion protein have been reported (Jestin et al., 1999, Angew. Chemi. Int. Ed., vol. 38, pp. 1124–1127; Demartis et al., 1999, JMB, vol. 286, pp. 617–633). In such cases, a high non-specific background is expected, because of the large excess of phage particles carrying the DNA encoding the pIII fusion, but not displaying the fusion on the surface. To circumvent this potential problem, we inserted a histidine tag between the pIII coat protein and the enzyme, allowing the purification of phages displaying His-tagged protein by Ni-NTA column chromatography.

Other tags that could have been used in a similar manner as described below for the Histidine tag include the intein-chitin binding domain fusion (Chong et al., 1997, Gene, vol. 192, pp 271–281), FLAG peptide (Slootstra et al., 1997, Molecular Diversity, vol. 2, pp. 156–164), and the maltose binding protein (Pryor and Leiting, 1997, Protein expression and Purification, vol. 10, pp. 309–319).
Ni-NTA Column Purification of Phages Displaying the Lipase-His6-pIII or Cellulase-His6-pIII Fusion Protein.

A Ni-NTA spin column (Qiagen Spin Kit) was equilibrated with 600 µL "50 mM sodium-phosphate buffer pH 8, 300 mM NaCl, 1 mM Imidazole, 0.05% BSA" (centrifuged 2 minutes at 700 G). To 400 µl phage preparation (see example 10 and 11) (approximately $10^{12}$ phage particles) was added 100 µL "250 mM sodium-phosphate buffer pH 8, 1.5 M NaCl, 0.25% BSA" and 4 µL 100 mM Imidazole, the solution loaded onto the pre-equilibrated column, and centrifuged for 4 minutes at 200 G. The column was washed twice with 600 µL "50 mM sodium-phosphate buffer pH 8, 300 mM NaCl, 20 mM Imidazole, 0.05% BSA" (centrifugation 200 G for 4 minutes and 700 G for 2 minutes, respectively). Then the phages were eluted with 3×333 µL "50 mM sodium-phosphate buffer pH 8, 300 mM NaCl, 250 mM Imidazole, 0.05% BSA" (700 G, 2 minutes), and the 999 µL eluate PEG precipitated and resuspended in 400 µL "50 mM sodium-phosphate buffer pH 8, 300 mM NaCl, 1 mM Imidazole, 0.05% BSA". The solution was loaded on a fresh spin column, and the procedure repeated, except that the final PEG precipitate was dissolved in 50 µL TE buffer pH 8. This procedure enriches approximately 500 fold for phage displaying His-tagged protein.

Example 10

Enrichment of Wildtype Lipase in a Background of Excess, Less Active Lipase Variants, Using Phage-displayed Lipase and DNA Oligos as the XY Exchange Pair This is an example of the selection scheme depicted in FIG. 10B.
Phagemid Construction.

Phagemid ph8 (wildtype Lipase) and ph18 (Lipase S146A mutant): DNA oligos "Not-His6-sense" (5'-GGCCGCACCAGGAGGAGGATCACATCACCATCAC CATCACTC-3') SEQ ID NO: 31 and "Not-His6-antisense" (5'-GGCCGAGTGATGGTGATGGTGATGTGATCCTCC TGGTGC-3') SEQ ID NO:32 were annealed, and the double-stranded product ligated into NotI-digested pFab-SP400 (described above) and pFab-SP400-S146A (identical top Fab-SP400, except that it carries a serine to alanine mutation at position 146, lowering its activity at least 100-fold). The resulting phagemids, ph8 (wildtype Lipase) and ph18 (Lipase S146A mutant), carry the amino acids sequence shown in SEQ ID NO 2 (wildtype shown) The resulting gene fusion comprises (reading from the N-terminal end) the pelB signal sequence (underlined), the gene encoding mature lipase (wt or S146A mutant), the insert (italics) with the six histidines (bold), and the pIII gene from amino acid residue 198 (underlined).
Production of Phage Particles.

Phage particles were produced with minor modifications according to Ørum et al. (see example 2). Briefly, *E. coli* XL1blue were transformed with either the phagemid ph8 (Lipase wt) or phagemid ph18 (Lipase S146A mutant), or ph13 (a negative control; carries a His-tagged cellulase instead of Lipase, but is otherwise identical to the ph8 and ph18 constructs). The transformed cells were shaken at 37° C. in 2×YT medium containing 100 µg/mL ampicillin, 5 µg/mL tetracyclin and 2% glucose. At an $OD_{600}$ of 0.5, acid helper phage (a M13K07 derivative, carrying a 30'meric acid peptide extension at the N-terminus of pIII, see Pedersen et al., PNAS (1998), 95, pp. 10523–10528) was added to a final concentration of 1.5×108 cfu/mL, and incubated at 37° C. for 20 min. The cells were pelleted and resuspended in 2×YT, 5 µM IPTG (100 mM IPTG for ph13), 100 µg/mL ampicillin, 50 µg/mL kanamycin, and shaken for 3 hours at 30° C. Cells were pelleted and phage particles in the supernatant PEG precipitated three times and resuspended in 400 µL TE buffer (10 mM Tris-HCl pH 8; 1 mM EDTA).

Before covalent coupling of base-linker-X to phage (see below), a pre-enrichment step for the phages displaying the Lipase variant was performed, following the protocol of example 9. The procedure generally led to a recovery of 0.04–0.2% of the input phage; we estimate that more than 90% of the recovered phage display lipase.
Active, Histidine-tagged Lipase is Displayed on Phage.

In order to verify that the prepared phages display the Lipa sepIII fusion proteins, separate wells of a microtiter plate were coated with antibodies against the histidine tag (Penta-His antibody, Qiagen), antibodies against the Lipase protein, or, as a negative control, an antibody against an unrelated amylase enzyme. Approximately $10^9$ phages displaying non-His-tagged wildtype Lipase (ph3), His-tagged wildtype Lipase (ph8) or His-tagged Lipase S146A mutant (ph18) were added to separate wells. The results shown in FIG. 16 show that ph8 and ph18 both display the His tag as expected; the non-His-tagged wildtype Lipase is not significantly bound to the anti-His antibody. Both mutant and wildtype Lipase are immobilized on anti-Lipase antibody, as expected. Finally, none of the Lipase variants are immobilized on the unrelated antibody. It is therefore concluded that the ph8 and ph18 phagemids encode Lipase-Histidine tag-pIII fusions that are folded properly on the surface of phage. The His-tagged phages (ph8 and ph18), were taken through the Ni-NTA column purification step described in example 9. The enrichment step is expected to yield a phage population almost entirely consisting of phages displaying the His-tagged protein. The procedure involves two consecutive Ni-NTA column purifications; the first run reproducibly recovered 0.2–0.3% of the input, the second run recovered 10–20% of the input. These numbers are taken as an indication that the resulting phage population have been enriched dramatically with regard to displayed protein, and that the final phage population consists of phages that nearly all display the protein. Finally, in a Brilliant Green plate assay, cells containing the wildtype LipaseHis-pIII fusion but not cells containing the Lipase S146A-pIII fusion, exhibited Lipase activity. It is therefore tentatively concluded that ph8 display active, properly folded wildtype Lipase; the ph18-phages display properly folded Lipase S146A mutant with decreased Lipase activity.
Synthesis of Base-linker-DNA Conjugate ("Base-linker-X").

The base-linker peptide $C(GGS)_4$ AQLKKKLQALKKKNAQLKWKLQALKKKLAQGGC SEQ ID NO:9 was conjugated to the 5'-thiol of the DNA oligos "X-26mer" (HS-5'-ATTAAATT AGCGCAATGAAGGGCAAC-3') SEQ ID NO:33 and photodeprotected, following the protocol described in Pedersen et al., PNAS (1998), 95, 10523–10528. The underlined sequence constitutes the X moiety. The resulting conjugate is called "base-X-26mer".
Synthesis of Y-substrate-biotin Conjugates.

The heterofunctional molecule (39) (see FIG. 17) containing a maleimide moiety at one end, a biotin at the other, and an ester that serves as a substrate for the Lipase in the middle, was prepared. ω-Aminododecanoic acid was first protected as its methyl ester (40) which was coupled with biotin-NHS followed by hydrolysis to give biotin-acid (41). Convergently, Maleimide alcohol (42) was prepared by reacting maleimide-NHS with 6-hydroxyhexylamine. Esterification between (41) and (42) afforded the target substrate (39). Finally, compound (39) was conjugated to either Y1 DNA oligo (5'-SH-AATAAATAAACGGG TGCCCTTCATT-3') SEQ ID NO:34 or Y2 DNA oligo (5'-TTCATTGCGCTTCGGCAAATAAATAA-SH-3') SEQ ID NO:35. The underlined sequences constitute the Y1 and Y2 exchange moieties.

Covalent Attachment of Base-linker-DNA Conjugate to Phage.

The X-26mer conjugate (see above) is covalently attached to the Ni-NTA purified phages (see above), for example by following the guidelines in example 1 above. The phages from the coupling reaction may optionally be taken through another purification step, in order to assure a high degree of coupling. This involves annealing of the phages to streptavidin coated beads, to which a biotinylated oligo, complementary to the X-26mer, has been immobilized. Following several washes to remove phages that have not been covalently attached to the X-26mer, the temperature is increased to melt the DNA duplexes and release the coupled phages.

Isolation of the More Active Lipase.

The Y1-substrate-biotin and Y2-substrate-biotin conjugates are mixed with a streptavidin-derivatized matrix (for example streptavidin immobilized on 4% agarose, Sigma), at a concentration of 1–10 µM, and incubated at room temperature 1–2 hours. The column is washed, and phages to which the X-26mer conjugate has been coupled (see above) are added in a buffer that allows Lipase activity as well as efficient annealing (contains $MgCl_2$ and $CaCl_2$) at 20–35° C. Alternatively, the coupling step is performed directly on the column. The X-26mer DNA coupled to phage will anneal to the Y1- or Y2-substrate-biotin molecules and become immobilized on the matrix through the substrate. Phages displaying catalytically active Lipase will cleave the substrate and continue the migration through the column; upon interaction with another Y1- or Y2-substrate, an exchange reaction may take place, which will immobilize the phage again. A less catalytic Lipase will spend more time bound to a given substrate. Therefore, the catalytically more active phages will migrate faster than the less active phages, and can therefore be collected first at the bottom of the column.

Example 11

Enrichment of Wildtype Cellulase C6B, Displayed on Filamentous Phage, in a Background of Less Active Mutant Cellulases, Using the Cellulose Binding Domain (CBD) of the Cellulase as the X Unit, and Avicel (Cellulose) Matrix as Both Substrate and Y-unit Phagemid Construction.

Phagemid ph7 (cloning vector):

The DNA oligos "Not-His6-sense" (see above) and "Not-His6-antisense" (see above) were annealed, and the double stranded product ligated into NotI digested pFab5c.His (Ørum et al., 1993, Nucleic Acids Research, vol. 21, pp. 4491–4498), to form the phagemid ph7. Basically, this results in the addition of the amino acids sequence APGGS HHHHHHS SEQ ID NO:36 to the N-terminal end of the pIII coat protein (the His-tag is underlined).

Phagemid ph13 (cellulase wt):

A PCR reaction was performed on a synthetic DNA construct encoding wildtype cellulase C6B of Humicola insolens, using the primers:

NcoI-Cellulase-fwd:
5'-CGACATGCCATGGCGCAGTCCGGCAATCCG TTCTC SEQ ID NO:37.

NotI-Cellulase-bck:
5'-CCTTTAGAGCCTGCGGCCGCGCCTCCTGGG AGGCACTGGCTGTACCAC SEQ ID NO:38.

The product was digested with NcoI and NotI, and inserted into NcoI- and NotI-digested ph7 (see above), to give ph13.

Phagemid ph14 (cellulase D316A):

Construction as for ph13, except that a DNA molecule with the mutation D316A was used as template.

Phagemid 16 (cellulase D139A, D316A):

Two PCR reactions were first performed. In one, the template containing the mutation D316A (see above) was employed with the primers:

D139A-fwd:
5'-GCTGTGATTCTGGAACCCGCGGCCATC-GGCAACATGGTGAC SEQ ID NO:39.

NotI-Cellulase-bck:
5'-CCTTTAGAGCCTGCGGCCGCGCCTCCTGG GAGGCACTGGCTGTACCAC SEQ ID NO:40.

In another PCR, the same template but the primers:

NcoI-Cellulase-fwd: (see above)

D139A-bck: 5'-GTCACCATGTTGCCGAT-GGCCGCGGGTTCCAGAATCACAGC SEQ ID NO:41, was used. The two PCR products were purified on an agarose gel, and used as template for a PCR reaction using the primers "NcoI-Cellulase-fwd" (see above) and "NotI-Cellulase-bck" (see above). The resulting PCR product was digested with NcoI and NotI and inserted into NcoI- and NotI digested ph7 (see above). The resulting gene fusions have the sequence shown in SEQ ID NO 3 (wildtype shown; starting with the first codon of pelB and ending with the STOP codon of pIII). This corresponds to the following protein fusion (reading from the N-terminus): PelB peptide, Cellulase C6B, Histidine linker, pIII coat protein.

Phagemid ph17 (cellulose binding domain, CBD): A PCR reaction was performed using a synthetic DNA encoding wildtype Cellulase C6B from Humicola insolens (see above) and the primers "NcoI-CBD-fwd" (5'-CGA CATGCCATGGCGGCGAGAGGCGCTGCCGGTTC-3') SEQ ID NO:42 and "NotI-Cellulase-bck" (see above). The product was digested with NcoI and NotI, and inserted into NcoI- and NotI-digested ph7 (see above), to give ph17. The resulting protein fusion has the sequence shown in SEQ ID NO 4. This corresponds to the following protein fusion (reading from the N-terminal: pelB leader peptide, CBD domain, Histidine tag, pIII coat protein.

Preparation of Phage Particles.

Phages were prepared as described in example 10, except that 100 µM IPTG was added after super-infection with Helper Phage.

Active, Histidine-tagged Cellulase is Displayed on Phage.

In order to verify that the prepared phages display the Cellulase-pIII or CBD-pIII fusion proteins, separate wells of a microtiter plate was coated with antibodies against the histidine tag, antibodies against the Cellulase C6B protein, or, as a negative control, an antibody against an unrelated lipase enzyme (SP400, see example 2). Approximately $10^8$ phages displaying Cellulase wt (ph13), Cellulase D316A (ph14), Cellulase D316A,D139A (ph16), CBD (ph17) or an unrelated Lipase enzyme (ph3) were added to each well. The results shown in FIG. 18 show that ph13, ph14, ph16, and ph17 all display the His tag. The full-length cellulases (ph13, ph14, ph16) bind the anti-cellulase antibody, the CBD domain does not bind this antibody. As expected, the negative control (ph3) does not bind the anti-His or anti-cellulase antibodies. Also as expected, the cellulase and CBD displaying phages do not bind the anti-lipase antibody; the lipase-displaying phage (ph3) does, as expected. It is therefore concluded that the ph13, ph14 and ph16 phagemids encode cellulase-Histidine tag-pIII fusions, and that these most likely are folded properly on the surface of phage. The His-tagged phages (ph13, ph14, ph16, and ph17), were taken through the Ni-NTA column purification step described in example 9. The enrichment step is expected to yield a phage population almost entirely consisting of phages displaying the His-tagged protein. The procedure involves two consecutive Ni-NTA column purifications; the first run reproducibly recovered less than 0.1% of the input, the second run recovered approximately 20% of the input. These numbers are taken as an indication that the resulting phage population have been enriched dramatically with regard to displayed protein, and that the final phage population consists of phages that nearly all display the protein. Finally, in a liquid CMC-Congo Red cellulase activity assay it was further verified that cell extracts of XL1 blue carrying phagemid expressing wildtype Cellulase, but not cells expressing mutant D316A Cellulase, exhibited cellulase activity (data not shown). It is therefore proposed that ph13-phages displays active, properly folded wildtype Cellulase; the ph14- and ph16-phages display properly folded cellulase mutants with decreased cellulase activity.

The Principle of Substrate Reloading in the Context of the Phage-displayed Cellulase.

The Cellulase C6B from Humicola insolens consists of two domains, a core domain with catalytic activity and a cellulose binding domain, CBD, connected to the core via a linker of approximately 25 amino acids. We therefore reasoned that conditions might exist where the affinity of CBD for cellulose was appropriately weak that a reasonable exchange of CBD for different sites on cellulose could be achieved, and it might be possible to set up a column-based selection based on this exchange. Under such conditions, the CBD would bind a site on the cellulose, and thereby hold the core enzyme in the vicinity of this binding site (FIG. 19). An active enzyme might cleave the cellulose string to which its CBD domain was attached, and hence release itself. Whereas a less active enzyme would be immobilized on the cellulose until the CBD associated from its binding site. At one extreme, if the binding of CBD to cellulose was extremely strong, the cellulase would release itself from the column by cleavage, and elute from the column as a CBD-cellulose string complex. In this case, only one turn-over of substrate would be required, and hence, there would be a small selective pressure for the better cellulase. At the other extreme, the CBD-cellulose interaction would be so weak that the half-life of the CBD-cellulose complex, rather than the turn-over rate of the enzyme, would determine the time spent immobilized on the column. In this case there would therefore be little selective pressure for the more active enzyme.

CBD of Cellulase C6B has high affinity for acid-treated Avicel™ (microcrystalline cellulose, Merck) at neutral pH, and low affinity at high pH. Cellulase can be eluted from Avicel™ at pH above 11.6. We therefore set out to define conditions where the Cellulase would be active and the CBD binding appropriately low to obtain a multiple turn-over system that would distinguish between cellulases of different specific activity.

The CBD Domain of the Displayed Cellulase Binds the Avicel™ Column Material.

We wanted to use the CBD-cellulose interaction as a simple model for a XY-exchange unit. Therefore, the ability of the CBD domain to reversibly bind phosphoric acid swollen Avicel™ was examined. Approximately 1 mg acid-swollen Avicel™ was mixed with Sephacryl to obtain a column bed volume of approximately 2 mL. Ni-NTA purified ph17-phage (see above) were loaded on the gel in Naphosphate buffer pH 7.5, and washed with several column volumes at increasing pH (same conditions as below). Control phages displaying an unrelated lipase enzyme were collected from the first fractions; the ph17-phages were not eluted until after several column volumes of Naphosphate buffer pH 11.6 (data not shown). Therefore, the CBD domain displayed on phage binds acid-swollen Avicel at neutral pH; at pH 11.6 the affinity is decreased and CBD is eluted.

Active Cellulase is Enriched Over Less Active Cellulase.

Next, we loaded an approximately 1:1 mix of Ni-NTA purified phages displaying wt cellulase (ph13) or D139A, D316A mutant cellulase (ph16) on an Avicel™/Sephacryl™ column, prepared as described above. In this experiment the temperature was 50° C. Again, the loading buffer was 20 mM Na-phosphate buffer pH 7.5, 0.05% BSA, 0.05% Tween. After washing with 1 volume 20 mM Na-phosphate buffer pH 7.5, 0.05% BSA, 0.05% Tween, 500 mM NaCl and 1 volume 20 mM Tris-HCl pH 8.5, 0.05% BSA, 0.05% Tween, 200 mM NaCl, the pH was increased to pH 10.6 for the next 6 column volumes. Finally, the pH was increased to 11.6.

Fractions were collected and the phage titer in each fraction determined. Also, the ratio of ph13:ph16 was determined by PCR reaction followed by PstI digestion and agarose gel analysis. The D316A mutation introduces a PstI site, wherefore PstI digestion gives rise to two, smaller fragments. The intensity ratio of the upper and middle band on an agarose gel therefore correlates with the relative number of wildtype cellulase (ph13) to mutant cellulase phage (ph16) in a given fraction. The ratio of ph13:ph16 in the input was approximately 0.7. In fractions 1–2 (corresponding to pH 7.5) and fractions 4–11 (corresponding to pH 10.6/11.6) the pH16 phage was in 1–10 fold excess, as estimated from the gel. In fraction 3, the ratio of pH13:pH16 was approximately 1.5. Therefore, an approximately 2-fold enrichment of the more active (wildtype, ph13) cellulase in a background of less active (double-mutant, ph16) cellulase had been achieved. It should be noted that 52% of the output phage was recovered in fractions 2–4, 17% in fractions 1 and 7–11, and 31% of the phage remained immobilized on the column after 30 column volumes wash at pH 11.6.

In similar experiments we have not been able to enrich the wildtype cellulase in a background of the pH14 single-mutant. We have reproducibly observed the two phases of the selection (i.e., in the first fractions ph16 is recovered in excess, then ph13 is recovered in excess over one or two fractions, and then ph16 is recovered in excess in the remaining fractions). The fact that there are these two phases corroborate the proposal that at least two events take place as the phage displaying the cellulase migrates through the column: binding of the CBD domain to cellulose, and cleavage of the cellulose.

In the experiment the CBD-Avicel interaction represents an XY-exchange unit. It was expected that this very simple XY unit would be sub-optimal: Firstly, most macromolecular interactions are described by slow kinetics, which would lead to slow substrate reloading in this example. Secondly, the binding of CBD and cellulose with respect to on- and off-rates was sought optimized through appropriate choice of pH. As the pH also affects the catalytic activity of the cellulase this is not ideal. Possibly, the binding may be adjusted by other means that do not interfere significantly with cellulase activity, for example salt concentration or the inclusion of high concentrations of detergents. If the affinity and/or the kinetics of the CBD-cellulose interaction can be optimized further this way, this should increase the stringency of the selection, and thus allow a separation of enzymes with only slightly different levels of activity (represented in the experiment above by the wildtype and single-mutant cellulase).

Alternatively, the approach of example 10 may be applied to the phage-displayed Cellulase: [i]Rescue the phages (ph13, ph14, ph16, ph17 etc.) with the acid helper phage, [ii]Ni-NTA purify phages displaying cellulase variants, [iii]couple the base-X-26mer conjugate to phages, [iv]immobilize Y-substrate conjugates on a column (substrate here denotes cellulose, for example 2 or 6 glucose units linked by β-1,4 bonds), [v]perform the substrate reloading protocol. This might increase the rate of substrate reloading, and allow separation of slightly different cellulase activities.

We conclude that even with this simple CBD-cellulose exchange unit it was possible to enrich for the more active cellulase (ph13) in a background of less active cellulases (ph16).

Example 12

Enrichment of Wildtype RNaseA Peptide on Beads, in a Background of Excess, Less Active RNase A Peptide Variants, Using a Polyhistidine Tag as the X Unit, and Iminodiacetic Acid as the Y Unit In order to test the substrate reloading principle in the field of synthetic combinatorial libraries, we have designed a simple experiment involving the RNase A peptide. Two C-terminally biotinylated peptides, Peptide1 and Peptide2, are synthesized, for example as outlined in (Gutte et al., 1971, Journal of Biological Chemistry, vol. 246, pp. 1922–1941). Peptide1 carries wildtype RNase A sequence, except that six histidines have been added to the N-terminus. Peptide 2 has the same sequence as Peptide1, except that mutation(s) have been introduced that fully or partly eliminates the ribonuclease activity of the peptide (for example by replacing one or both of the two active site histidines, H12 and H119, with Alanine). After deprotection, cleavage from synthesis support, and refolding as described in (Gutte et al., 1971, Journal of Biological Chemistry, vol. 246, pp. 1922–1941) the peptides are immobilized through the C-terminal biotin moiety to streptavidin coated beads of approximate diameter 10–100 nm. Such beads may be prepared by immobilizing streptavidin to N-hydroxy-succinimide-activated Latex beads (Polysciences Inc.). A column (eg. Sepharose or Sephadex) is prepared, carrying RNA molecules immobilized at one end to the matrix, and at the other end coupled to iminodiacetic acid (IDA) or nitrilotriacetic acid (NTA). This may be done by synthesis of an RNA oligo (for example 20 nt long), functionalized with a thiol at one end, and biotin at the other end (Oligos Etc., Inc.). Then the thiol is used to specifically couple the RNA and iminodiacetic acid (or nitrilotriacetic acid), by standard protocols.

A substrate reloading experiment is now performed as follows (FIG. 20). The beads carrying either Peptide1 or Peptide2 are mixed in a buffer that allows RNase A activity (for example Tris-HCl pH 7 or 8) containing metal ions (for example $Zn^{++}$ or $Ni^{++}$), and loaded on the column described above. The column is washed with the same buffer, and fractions collected. During their migration through the column, the Peptide beads become immobilized to the column matrix through the interaction of the six N-terminal histidines, $Zn^{++}$ or $Ni^{++}$, and the IDA coupled to the RNA molecule. Thus, a His6-metal-IDA complex is formed, which in effect attaches the bead carrying the peptides to the RNA, the substrate of RNase A. The active RNase A (Peptide1) will cleave the attached RNA and release itself, and thus continue its migration through the column. Peptide2, however, is catalytically less active than Peptide1, and will stay immobilized for a longer period of time, and hence, after a number of turn-overs the Peptide1 beads will have separated from the Peptide2 beads as a result of their differential catalytic activity towards the RNA substrate. The beads carrying the more active RNase A variant can therefore be collected first at the bottom of the column.

Using unnatural amino acids the catalytic machinery of RNase A may be examined, and potentially, new improved variants of RNase A evolved (Jackson et al., 1994, Science, vol. 266, pp. 243–247), using the substrate reloading selection outlined above. Alternatively, totally random peptide libraries may be searched for novel catalysts. The sequence of the peptides on the recovered beads can be determined by Edamn degradation or mass spectrometry.

Example 13

Enrichment of the More Active Staphyloccoal Nuclease (SNase) Variants in a Background of Less Active Snase Variants. This Selection Employs Electrophoresis to Isolate the More Active Enzymes A His6-tag is introduced either into the linker connecting SNase and pIII coat protein in the phagemid pII78-6 (Pedersen et al., 1998, Proc. Natl. Acad. Sci. USA, vol. 95, pp. 10523–10528), or alternatively, the His6-tag is cloned at the N-terminal end of gpIII gene of the M13K07 Helper Phage (following the cloning procedure outlined for the cloning of the acid extension into M13K07, described in Pedersen et al., 199872991, Proc. Natl. Acad. Sci. USA, vol. 95, pp. 10523–10528). Phage particles are produced, using regular M13K07 Helper Phage and the His6-tagged SNase phagemid, or using the pII78-6 phagemid and the His6-tagged Helper Phage. Both methods yield phages displaying SNase and a His6-tag on their surface.

A DNA oligo of approximately 20 nucleotides is derivatized at the 5'-end with iminodiacetic acid (IDA) or nitrilotriacetic acid (NTA), using standard procedures. For example, the oligo may be synthesized with a 5'-thiol, which is then derivatized with a bifunctional IDA-maleimide moiety. The derivatized oligo is now used for PCR, together with another primer, and a template that gives rise to a PCR product of 100–1000 base pairs.

The DNA fragment, derivatized with IDA or NTA at one end, is incubated with phages produced above, and loaded on a gel for electrophoresis, for example an 0.5–0.7% agarose gel in a suitable buffer. The buffer (Tris-HCl pH 5–8) contains $Ca^{++}$ (for SNase activity) and $Zn^{++}$, $Ni^{++}$, $Co^{++}$, or $Cu^{++}$ (for coordination to His6 and the IDA or NTA moiety), and a high concentration of the IDA- or NTA-derivatized DNA fragment described above.

The His6-tag, displayed on phage, binds DNA through formation of the complex His6-metal-IDA (or His6-metal-NTA). If the SNase displayed on the same phage is active, it cleaves the associated DNA. At the same time, a rapid exchange between different DNA fragments results in the constant reloading of full-length fragment on phage. Therefore, the phage displaying the more active SNase will on average be associated with smaller fragments of DNA, and therefore migrates differently than phages displaying inactive SNase. The experiment is performed by mixing phages displaying a number of different SNase variants, and isolating the more active variants by electrophoresis as described above.

Example 14

DNA Oligos as XY Exchange Units: Measurement of Exchange Rates by Fluorescense Polarization Spectroscopy A fundamental feature of the indirect substrate reloading protocol is the XY exchange unit that links the substrate and enzyme. Ideally, the XY unit should provide a means for the dynamic, fast and efficient substrate reloading on the enzyme. We wanted to design nucleic acids that would fulfill (at least partly) the requirements of the ideal XY unit: fast exchange, yet intrinsically stable XY complexes. Therefore, two sets of oligos, Set#1 and Set#2, were designed. The XY complexes of the two sets have expected melting temperatures around 60 and 40° C., respectively. To provide a dynamic exchange, the DNA oligos were designed so that the two DNA oligos, Y1 and Y2, bound to different but overlapping targets on X (see Materials and Methods). With the expectation that the overlap would provide a faster exchange between the X-Y1 and X-Y2 complexes.

The exchange rates of the two sets of oligos were analyzed by fluorescense polarization spectroscopy at various temperatures. The dynamic range (the temperature range at which the oligos exchange relatively fast yet where X is complexed) was slightly lower than the predicted melting temperature of the XY duplexes. The time required to obtain a 90% exchange of free Y for complex bound Y ("$t_{(exchange)}$") varied between 30 and 500 seconds. It is expected that with other designs of oligos and optimized conditions (in particular $Mg^{++}$ concentration and temperature), it should be possible to obtain exchange rates for nucleic acids faster than one per second, possibly 10–100 per second.

Materials and Methods
DNA Oligo Sequences.
  Set #I:
  X#1: 3'-TGCTAGCATGGCCCAACGGGAAGTAACGC GAAGCCGATGCTAGCATGC-5' SEQ ID NO:43
  Y1-Fl#1: 5'-Fam-CGGGTTGCCCC<u>TTCATT</u>-3' SEQ ID NO:44
  Y1#1: 5'-CGGGTTGCC<u>TTCATT</u>-3' SEQ ID NO:45
  Y2#1: 5'-<u>TTCATT</u>GCGCTTCGGC-3' SEQ ID NO:46
  Set#II:
  X#2: 3'-ACGGGAAGTAACGCGA-5' SEQ ID NO:47
  Y1-Fl#2: 5'-Fam-TGCCC<u>TTCATT</u>-3' SEQ ID NO:48
  Y1#2: 5'-TGCCC<u>TTCATT</u>-3' SEQ ID NO:48
  Y2#2: 5'-<u>TTCATT</u>GCGCT-3' SEQ ID NO:49
Sequences that are complementary in X and Y are in bold; the region of Y1 and Y2 that overlap is underlined. FAM denotes the fluorescent moiety.
Flourescense Polarization Spectroscopy.

The measurements were done on a Perkin Elmer LS50 spectrophotometer. Excitation was at 485 nm, emission was recorded at 525 nm. All measurements were done in Buffer A (10 mM Tris-HCl pH 9, 100 mM NaCl, and 1 mM $MgCl_2$ unless noted otherwise). A thin tubing was connected to the sample cuvette; therefore, it was not necessary to open the lid during addition of extra material. With this set-up, it is not possible to measure rates of reactions that proceed to near-completion within 30 seconds.

Results
Design of XY Exchange Units Based on Nucleic Acids.

For the final application, the XY exchange unit in the enzyme-linker XY linker-substrate structure should be in rapid equilibrium with an excess of Y-substrate molecules in the buffer, thus facilitating a rapid exchange of product (or substrate) "attached" to the enzyme, through an exchange of Y-product (or Y-substrate) with Y-substrate in the buffer.

In order to accomplish this rapid equilibrium, we designed two oligos, Y1 and Y2, with overlapping (but not identical) binding sites on the X oligo (see materials and methods). Thus, Y2 would be able to transiently interact with X in the X:Y1 complex through the portion of X that does not anneal to Y1, and vice versa. When annealing to the full complementary sequence on X, Y1 and Y2 form the same number of AT and GC base pairs, and are therefore expected to have near-identical affinity for X, and presumably similar on- and off-rates. Therefore, Y1 should replace Y2 from the X:Y2 complex as fast as Y2 replaces Y1.

We designed two sets of oligos, with different length of annealing site and different relative length of annealing and overlapping regions. The sequence of the overlapping region (5'-TTCATT-3') was chosen so as to avoid triplex formation; moreover, in the experiments (and in example 10) very low concentrations of X and Y are used. Therefore, triplex formation is highly unlikely.
Exchange of Y2 With Y1 of the X-Y1 Complex.

Fluorescense polarization was used to analyze the exchange rates of each of the two sets of oligos. Fluorescense polarization of a fluorescently labelled molecule in solution is proportional to the molecule's rotational relaxation time. If viscosity and temperature is held constant, the fluorescense polarization value is directly proportional to the molecular volume. Changes in molecular volume may result from binding or dissociation of two molecules, as used in this study.

First oligo Set#1 was analyzed. Fluorescein-labelled Y1 oligo (Y1-Fl#1, see Materials and Methods) at a concentration of 5 nM and temperature 46° C. gives a fluorescense polarization value of 0.028 (see FIG. 21, upper panel). Upon addition of a 200-fold excess (1 μM) of oligo X#1 at time t=660 sec, the polarization rapidly increases to a plateau at about 0.037, indicating the formation of the X:Y1-Fl#1 complex. When Y2#1 is added in a 20-fold excess to X (20 μM) at t=2400, the polarization rapidly drops, indicating the release of Y1-Fl#1 from the X:Y1-Fl#1 complex. Most likely, the X:Y2#1 complex is formed, displacing Y1-Fl#1 from X#1.

The displacement of Y1-Fl#1 from X#1 by Y2#1 is a relatively fast process; within 30 seconds, 90% equilibrium is observed. Formation of the X#1:Y1-Fl#1 complex is a slower process (approximately 600 seconds for 90% equilibrium to be obtained). However, this is explained by the fact that the concentration of the oligo in excess is 20 fold lower.

Next, the same binding reactions were analyzed at 50° C. Less time (300 sec) is required for formation of the X:Y1 complex; on the other hand, the exchange goes to 90% completion a little slower (40 sec, see table 1).

We wanted to challenge the idea that overlapping targets can speed up the exchange rate. Therefore, the X#1:Y-Fl#1 complex was formed under identical conditions (46° C.), but now oligo Y1#1 (instead of Y2#1) was added in a twenty-fold excess to X#1. As can be seen from (FIG. 21, lower panel) and (table 1), the displacement of Y1-Fl#1 by un-labelled Y1#1 is slow. About 500 seconds are now required to obtain 90% equilibrium. We conclude that the principle of overlapping targets for Y1 and Y2 on X in this case accelerates the exchange by a factor of approximately 17.

Oligo Set#2 was analyzed in the same way (see table 1). At reference conditions of 24° C. and 1 mM $MgCl_2$, the exchange reaction goes to 90% completion within 200 seconds. Increasing the temperature to 30° C. speeds up the exchange 4-fold; likewise, increasing the Mg++ concentration to 10 mM increases the exchange 4-fold. The present set-up has a response time of about 30 seconds. Therefore, we did not attempt to measure the exchange rate at 10 MM $MgCl_2$ and 30° C.

Finally, the principle of overlapping targets was again challenged. Under less than optimal conditions (24° C., 1 mM $MgCl_2$), the exchange of Y1 for Y1-Fl complexed to X goes to 90% completion within 500 seconds; this is 2.5-fold slower than for the exchange of Y2 for Y1. Therefore, it is advantageous to include two rather than one "Y-unit", even though under these conditions it speeds up the exchange only 2.5-fold.

In FIG. 21, lower panel, the fluorescense polarization signal does not come down to the base line (the signal level for free Y1-Fl). This observation was done several times, for both Set#1 and Set#2 oligos, for exchange of Y1 for Y1 and Y2 for Y1, as well as with different $MgCl_2$ concentrations. We have no explanation for this phenomenon; however, it did not seem to influence the measured exchange rates. Addition of a large excess of Y2 to free Y1-Fl in the absence of X has no effect on the fluorescense polarization signal.

Discussion

The exchange rates of both sets of oligos showed a strong dependence on the temperature; the temperature at which the selection experiment is performed should be held within a relatively narrow window of about +/−5° C. around the optimal temperature, in order for the exchange to be efficient.

The $MgCl_2$ concentration had a strong effect on the exchange rate. A similar effect may have been observed by (Shimayama et al., (1995), FEBS Letters 368, 304–306), for a so-called "DNA-armed hammerhead ribozyme". They found that the catalytic activity of the hammerhead ribozyme, in which the hybridizing arms had been replaced with deoxyribonucleotides, depended strongly on the $Mg^{++}$ concentration, even at high magnesium concentrations where the active site (requiring $Mg^{++}$ for activity) is believed to be saturated with $Mg^{++}$. Their results might therefore be interpreted in terms of high $Mg^{++}$ concentrations speeding up the exchange of the nucleic acids arms on the RNA target.

Design of XY exchange units based on nucleic acids should be a very general way to produce fast and efficient exchange units. Appropriate choice of length and composition of annealing sites and conditions under which the selection is performed, should allow the use of DNA oligos as XY exchange units under different conditions of pH, salt, temperature, pressure etc. In the present study it was shown that optimization of either $Mg^{++}$ concentration or temperature could bring the exchange rate down to the limit of the apparatus (tens of seconds). A combination of these conditions, potentially combined with optimization of other conditions, should bring the exchange rate down to approximately 1 per second. Finally, tuning of the relative length and composition of the annealing sites and overlapping regions of the Y1 and Y2 oligos should provide further improvements.

The design of Y1 and Y2 oligos with overlapping binding sites on the X oligo accelerated the exchange rate. Presumably the overlapping targets mediate active displacement of one oligo by the other. More sophisticated designs of XY exchange units, based on this concept and on the structural and mechanistic features of antisense RNA, should improve the dynamics of the system even more.

TABLE 1

Time of 90% complex formation and 90% exchange, at various conditions of temperature and $MgCl_2$.

| exchange | $Mg^{++}$ (mM) | temp. (° C.) | t (complex formation) (sec) | t (exchange) (sec) |
|---|---|---|---|---|
| Set#1 | | | | |
| Y1 / Y2 | 1 | 46 | 600 | 30 |
| Y1 / Y2 | 1 | 50 | 300 | 40 |
| Y1 / Y1 | 1 | 46 | 800 | 500 |
| Set#2 | | | | |
| Y1 / Y2 | 1 | 24 | 80 | 200 |
| Y1 / Y2 | 1 | 27 | 300 | 100 |
| Y1 / Y2 | 1 | 30 | 100 | 50 |
| Y1 / Y2 | 1 | 33 | 80 | 200 |
| Y1 / Y2 | 5 | 24 | 70 | 70 |
| Y1 / Y2 | 10 | 24 | 90 | 50 |
| Y1 / Y2 | 500 | 24 | 400 | 70 |
| Y1 / Y1 | 1 | 24 | 200 | 500 |

First oligo (Y1-Fl) was added to 5 nM; second oligo (X) was added to 1 μM; third oligo (Y2 or Y1) was added to 20 μM.

What is claimed is:

1. A method for selecting a catalyst from a library of catalysts, comprising:
   a. providing a composition, said composition comprising
      (i) a library of catalysts comprising at least two different catalysts present in the library as individual units having the structure catalyst-linker-substrate, wherein the substrate and the catalyst are positioned in the unit in a configuration that allows a catalytic reaction to occur between the catalyst and the substrate so as to form at least one product that remains a part of the unit, thereby generating a unit having the structure catalyst-linker-product, and
      (ii) free substrate; wherein under suitable conditions the linker exchanges the product of the catalyst-linker-product unit with free substrate so as to regenerate the catalyst-linker-substrate unit;
   b. providing conditions suitable for catalysts in the library to catalyze the reaction of the substrate to form the at least one product, wherein at least one product of the catalytic reaction remains part of the unit and forms the catalyst-linker-product units;
   c. providing conditions suitable for an exchange to occur between the free substrate and a product in the structure catalyst-linker-product so as to regenerate the catalyst-linker-substrate units;
   d. repeating steps b and c at least once; and
   e. selecting a catalyst of interest.

2. The method of claim 1, wherein said unit is biologically amplifiable.

3. The method of claim 1, wherein said catalyst and said substrate are attached on the surface of a biologically amplifiable unit.

4. The method of claim 1, wherein said linker is a flexible linker.

5. The method of claim 1, wherein said method further comprises using a carrier system to select a catalyst from a library of catalysts.

6. The method of claim 5, wherein said carrier system is a phage.

7. The method of claim 5, wherein said carrier system is a bead particle.

8. The method of claim 1, wherein the catalyst of interest is selected based on the ability to catalyze the reaction of a substrate to a product faster than other catalysts in the library of catalysts under the conditions employed.

9. The method of claim 1, wherein the catalyst of interest is selected based on the ability to perform more catalytic reactions than other catalysts in the library of catalysts over a period of time under the conditions employed.

* * * * *